(12) United States Patent
Hewitt et al.

(10) Patent No.: US 11,237,169 B2
(45) Date of Patent: Feb. 1, 2022

(54) RATIO BASED BIOMARKERS AND METHODS OF USE THEREOF

(71) Applicant: The United States of America, as represented by the Secretary, Dept. of Health and Human Services, Bethesda, MD (US)

(72) Inventors: Stephen M. Hewitt, Potomac, MD (US); Joon-Yong Chung, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/217,540

(22) Filed: Dec. 12, 2018

(65) Prior Publication Data

US 2019/0113517 A1 Apr. 18, 2019

Related U.S. Application Data

(63) Continuation of application No. 15/349,991, filed on Nov. 11, 2016, now abandoned, which is a continuation of application No. 13/144,474, filed as application No. PCT/US2010/020944 on Jan. 13, 2010, now abandoned.

(60) Provisional application No. 61/144,501, filed on Jan. 14, 2009.

(51) Int. Cl.
| | |
|---|---|
| *G16H 50/20* | (2018.01) |
| *G01N 33/574* | (2006.01) |
| *G16B 99/00* | (2019.01) |
| *G16Z 99/00* | (2019.01) |
| *G16B 25/10* | (2019.01) |
| *G01N 33/58* | (2006.01) |

(52) U.S. Cl.
CPC ..... *G01N 33/57484* (2013.01); *G01N 33/582* (2013.01); *G16B 25/10* (2019.02); *G16B 99/00* (2019.02); *G16H 50/20* (2018.01); *G16Z 99/00* (2019.02); *G01N 2800/60* (2013.01)

(58) Field of Classification Search
CPC .................................................. G01N 33/57484
USPC ............................................................ 506/7
See application file for complete search history.

(56) References Cited

U.S. PATENT DOCUMENTS

| 6,969,615 B2 | 11/2005 | Knezevic et al. |
|---|---|---|
| 7,419,777 B2 | 9/2008 | Bacus |
| 2007/0031902 A1 | 2/2007 | Pestano et al. |
| 2007/0065859 A1 | 3/2007 | Wang et al. |
| 2007/0207489 A1 | 9/2007 | Pestano et al. |
| 2007/0253953 A1 | 11/2007 | Chen et al. |
| 2008/0108091 A1 | 5/2008 | Hennessy et al. |
| 2011/0105341 A1 | 5/2011 | Semizarov et al. |
| 2012/0052508 A1 | 3/2012 | Bilal et al. |
| 2013/0210648 A1 | 8/2013 | Stephen et al. |

FOREIGN PATENT DOCUMENTS

| EP | 2 228 655 A1 | 9/2010 |
|---|---|---|
| JP | 2008-538817 | 11/2008 |
| WO | WO 2006/086772 A2 | 8/2006 |
| WO | WO 2006/119980 A1 | 11/2006 |
| WO | WO 2006/133460 | 12/2006 |
| WO | WO 2007/130677 A2 | 11/2007 |
| WO | WO 2008/057305 A2 | 5/2008 |
| WO | WO 2008/109440 | 9/2008 |
| WO | WO 2010/083252 A2 | 7/2010 |

OTHER PUBLICATIONS

Gannot et al (Journal of Molecular Diagnostics, 2007, 9(3): 297-304).*
Lin et al. (Annals of Clinical & Laboratory Science, 2006, 36(3): 283-293).*
Sin et al (Blood, 2007, 109(5): 2165-2173).*
Takikita et al (Current Opinion in Biotechnology, 2007, 18: 318-325).*
Traicoff et al (Journal of Biomedical Sciences, 2007, 14: 395-405).*
Feldman et al (Cancer Research, 2004, 64: 4481-4486).*
Akihiko et al., "Clinical significance of the AKT pathway in small cell lung cancer and other neuroendocrine tumors," *Journal of Thoracic Oncology*, vol. 2, No. 8, Suppl. 4, pp. S809, 2007 (Abstract p. 1-181).
Ayala et al., "High levels of phosphorylated form of AKT-1 in prostrate cancer and non-neoplastic prostate tissues are strong predictors of biochemical recurrence," *Clin Canc Res.*, 10:6572-6578, 2004.

(Continued)

*Primary Examiner* — Sean E Aeder
(74) *Attorney, Agent, or Firm* — Klarquist Sparkman, LLP

(57) ABSTRACT

Compositions, methods and kits are described for identifying biomolecules (e.g., proteins and nucleic acids) expressed in a biological sample that are associated with the presence, development, or progression of a disease (such as cancer), or more generally determination of the etiology or risk factors associated with a disease. Sample types analyzed by the disclosed methods include but are not limited to archival tissue blocks that have been preserved in a fixative, tissue biopsy samples, tissue microarrays, and so forth. The methods disclosed herein correlate expression profiles of biomolecules with various disease types, and allow for the determination of relative survival rates; in some embodiments, the methods permit determination of survival rates for a subject with cancer. In other embodiments, the disclosure relates to methods for evaluating therapeutic regimes for the treatment, such as treatment of cancer.

12 Claims, 15 Drawing Sheets

(56) References Cited

OTHER PUBLICATIONS

Balsara et al., "Frequent activation of AKT in non-small cell lung carcinomas and preneoplastic bronchial lesions," Carcinogenesis, vol. 25, No. 11, pp. 2053-2059, 2004.
Becker et al., "Markers and Tissue Resources for Melanoma: Meeting Report," Cancer Res., 66(22):10652-10657, 2006.
Birner, et al., "Overexpression of Hypoxia-inducible Factor 1α is a Marker for an Unfavorable Prognosis in Early-Stage Invasive Cervical Cancer," Cancer Res., 60(17):4693-4696, 2000.
Braunschweig et al., "Tissue microarrays: bridging the gap between research and the clinic," Expert Rev Proteomics, 2(3):325-336, 2005.
Brennan et al., "Altered cytoplasmic-to-nuclear ratio of surviving is a prognostic indicator in breast cancer," Clin Canc Res., 2681-2689, 2008.
Burri, et al., "Significant correlation of hypoxia-inducible factor-1α with treatment outcome in cervical cancer treated with radical radiotherapy," Int. J. Radiation Oncology Biol. Phys., 56(2):494-501, 2003.
Camp et al., "Automated subcellular localization and quantification of protein expression in tissue microarrays," Nature Medicine, 8(11):1323-1327, 2002.
Campbell et al., "Combined expression of caveolin-1 and an activated AKT/mTOR pathway predicts reduced disease-free survival in clinically confined renal cell carcinoma," Br J Cancer, 98:931-940, 2008.
Carracedo et al., "Inhibition of mTORC1 leads to MAPK pathway activation through a PI3K-dependent feedback loop in human cancer," J Clin Invest., 118:3065-3074, 2008.
Chen et al., "Involvement of PI3K/PTEN/AKT/mTOR pathway in invasion and metastasis in hepatocellular carcinoma: Association with MMP-9," Hepatology Research, 39:177-186, 2009.
Chow et al., "Expression Profiles of ErbB Family Receptors and Prognosis in Primary Transitional Cell Carcinoma of the Urinary Bladder," Clin Cancer Res., 7:1957-1962, 2001.
Chung et al., "A multiplex tissue immunoblotting assay for proteomic profiling: a pilot study of the normal to tumor transition of esophageal squamous cell carcinoma," Cancer Epidemol Biomarkers Prev., 15:1403-1408, 2006.
Chung et al., "The Expression of Phospho-AKT, Phospho-mTOR, and PTEN in Extrahepatic Cholangiocarcinoma," Clin Cancer Res, 15(2):660-667, 2009.
Chung et al., "Tissue microarrays as a platform for proteomic investigation," J. Mol Hist, 38(2):123-128, 2007.
Chung et al., "Transfer and multiplex immunoblotting of a paraffin embedded tissue," Proteomics, 6:767-774, 2006.
De La Torre et al., "Expression of DNA damage checkpoint protein Hus1 in epithelial ovarian tumors correlates with prognostic markers," Int. J. Gynecol Pathol., 27:24-32, 2008.
Drab-Esfahani et al., "Phospho-mTOR and phosphor-4EBP1 in endometrial adenocarcinoma: association with stage and grade in vivo and linked with response to rapamycin treatment in vivo," J Cancer Res Clin Oncol., 10.1007/s00432-008-0529-5, 2008.
Evans et al., "C35 (C!&orf37) is a novel tumor biomarker abundantly expressed in breast cancer," Mol Cancer Ther., 5(1):2919-2930, 2006.
Fujimoto, et al., "Plausible linkage of hypoxia inducible factor-1α in uterine cervical cancer," Cancer Sci., 97(9):861-867, 2006.
Futreal et al., "A census of human cancer genes," Nat Rev Cancer., 4:177-183, 2004.
Gould Rothberg et al., "Melanoma Prognostic Model Using Tissue Microarrays and Genetic Algorithms," J Clin Oncology, 27(34):5772-5780, 2009.
Gould Rothberg et al., "Nuclear to non-nuclear Pmel17/gp100 expression (HMB45 staining) as a discriminator between benign and malignant melanocytic lesions," Modern Pathology, 21:1121-1129, 2008.
Gulmann et al., "Proteomic Analysis of Apoptotic Pathways Reveals Prognostic Factors in Follicular Lymphoma," Clin. Cancer Res., 15: 5847-5855, 2005.
Hayashi et al., "High Expression of HER3 is Associated with a Decreased Survival in Gastric Cancer," Clin Cancer Res., 14(23):7843-7849, 2008.
Horie et al., "Hepatocyte-specific Pten deficiency results in steatohepatitis and hepatocellular carcinomas," J. Clin. Invest., 113:1774-1783, 2004.
Isidoro et al., "Breast carcinomas fulfill the Warburg hypothesis and provide metabolic markers of cancer prognosis," Carcinogenesis., 26:2095-2104, 2005.
Kudoh et al., "Preoperative Determination of Several Seram Tumor Markers in Patients with Primary Epithelial Ovarian Carcinoma," Gynecol Ohstet Invest 47:52-57, 1999.
Lee et al., "Correlation between human epidermal growth factor receptor family (EGFR, HER2, HER3, HER4), phosphorylated Akt (P-Akt), and clinical outcomes after radiation therapy in carcinoma of the cervix," Gynecologic Oncology, 99:415-421, 2005.
McManus et al., "Biomarkers of esophageal adenocarcinoma and Barrett's esophagus," Cancer Res., 64:1561-1569, 2004.
Merseburger et al., "Activation of the PKB/Akt pathway in histological benign prostatic tissue adjacent to the primary malignant lesions," Oncol. Rep., 16:79-83, 2006.
Mukohara et al., "Expression of epidermal growth factor receptor (EGFR) and downstream-activated peptides in surgically excised non-small-cell lung cancer (NSCLC)," Lung Cancer, 41:123-130, 2003.
Qiao et al., "Gastrin-Releasing Peptide-Induced Down-Regulation of Tumor Suppressor Protein PTEN (Phosphatase and Tensin Homolog Deleted on Chromosome Ten) in Neuroblastomas," Annals of Surgery, 241(5): 684-692, 2005.
Ray et al., "Genomic and expression analysis of the 8p11-12 amplicon in human breast cancer cell lines," Cancer Res., 64:40-47, 2004.
Reimer et al., "FasL:Fas Ratio—A Prognostic Factor in Breast Carcinomas," Cancer Res. 60:822-828, 2000.
Rhodes et al., "Multiplex biomarker approach for determining risk of prostate-specific antigen defined recurrence of prostate cancer," J. Natl. Cancer Inst., 95:661-668, 2003.
Rojo et al., "4E-Binding protein 1, a cell signaling hallmark in breast cancer that correlates with pathologic grade and prognosis," Clin. Cancer Res., 13:81-89, 2007.
Roth et al., β-Catenin Splice Variants and Downstream Targets as Markers for Neoplastic Progression of Esophageal Cancer, Genes Chromosomes and Cancer 44(4):423-428, 2005.
Saxena et al., "Mcl-1 and Bcl-2/Bax Ratio Are Associated With Treatment Response but Not With Rai Stage in B-Cell Chronic Lymphocytic Leukemia," American Journal of Hematology 75:22-33, 2004.
Schneider et al., "Epidermal Growth Factor Receptor-Related Tumor Markers and Clinical Outcomes with Erlotinib in Non-small Cell Lung Cancer: An Analysis of Patients from German Centers in the TRUST Study", Journal of Thoracic Oncology, 3(12):1446-1453, 2008.
Sheilds et al., "Lack of Extracellular Signal-Regulated Kinase Mitogen-Activated Protein Kinase Signaling Shows a New Type of Melanoma," Cancer Res., 67(4):1502-1512, 2007.
Slesak et al., "Expression of epidermal growth factor receptor family proteins (EGFR, c-erbB-2 and c-erbB-3) in gastric cancer and chronic gastritis," Anticancer Research, vol. 18, No. 4A, pp. 2727-2732, 1998 (Abstract).
Tan et al., Evaluation of Biologic End Points and Pharmacokinetics in Patients with Metastatic Breast Cancer After Treatment With Erlotinib, an Epidermal Growth Factor Receptor Tyrosine Kinase Inhibitor, J Clin Oncology, 22(15):3080-3090, 2004.
Terakawa et al., "Loss of PTEN expression followed by Akt phosphorylation is a poor prognostic factor for patients with endometrial cancer," Endocrine-Related Cancer, 10:203-208, 2003.
Tockman et al., "Considerations in Bringing a Cancer Biomarker to Clinical Application," Cancer Res., 52(9 Suppl):2711s-2718s, 1992.
Xia et al., "Combination of EGFR, HER-2/neu, and HER-3 is a Stronger Predictor for the Outcome of Oral Squamous Cell Carci-

(56) References Cited

OTHER PUBLICATIONS noma Than Any Individual Family Members", *Clinical Cancer Research*, 5(12):4164-4174, 1999.

Xu et al., "Pharmacogenomic profiling of the PI3K/PTEN-AKT-mTOR pathway in common human tumors," *Int J Oncol.*, 24:893-900, 2004.

Xu et al., "The Outcome of Heregulin-induced Activation of Ovarian Cancer Cells Depends on the Relative Levels of HER-2 and HER-3 Expression," *Clin Cancer Res.*, 5:3653-3660, 1999.

Yanagisawa et al., "A 25-signal proteomic signature and outcome for patients with resected non-small-cell lung cancer," *J Natl Cancer Inst*, 99:858-867, 2007.

Yoshizawa et al., "Overexpression of Phospho-eIF4E is Associated with Survival through AKT Pathway in Non-Small Cell Lung Cancer," *Clin Cancer Res.*, 16(1):240-248, 2010.

Zeng, et al., "Expression of PTEN and P-Akt protein and their relationship with clinical features of epithelial ovarian cancer," *Journal—Shanxi Medical University*, 39(1):75, 2008 (Abstract Only).

\* cited by examiner

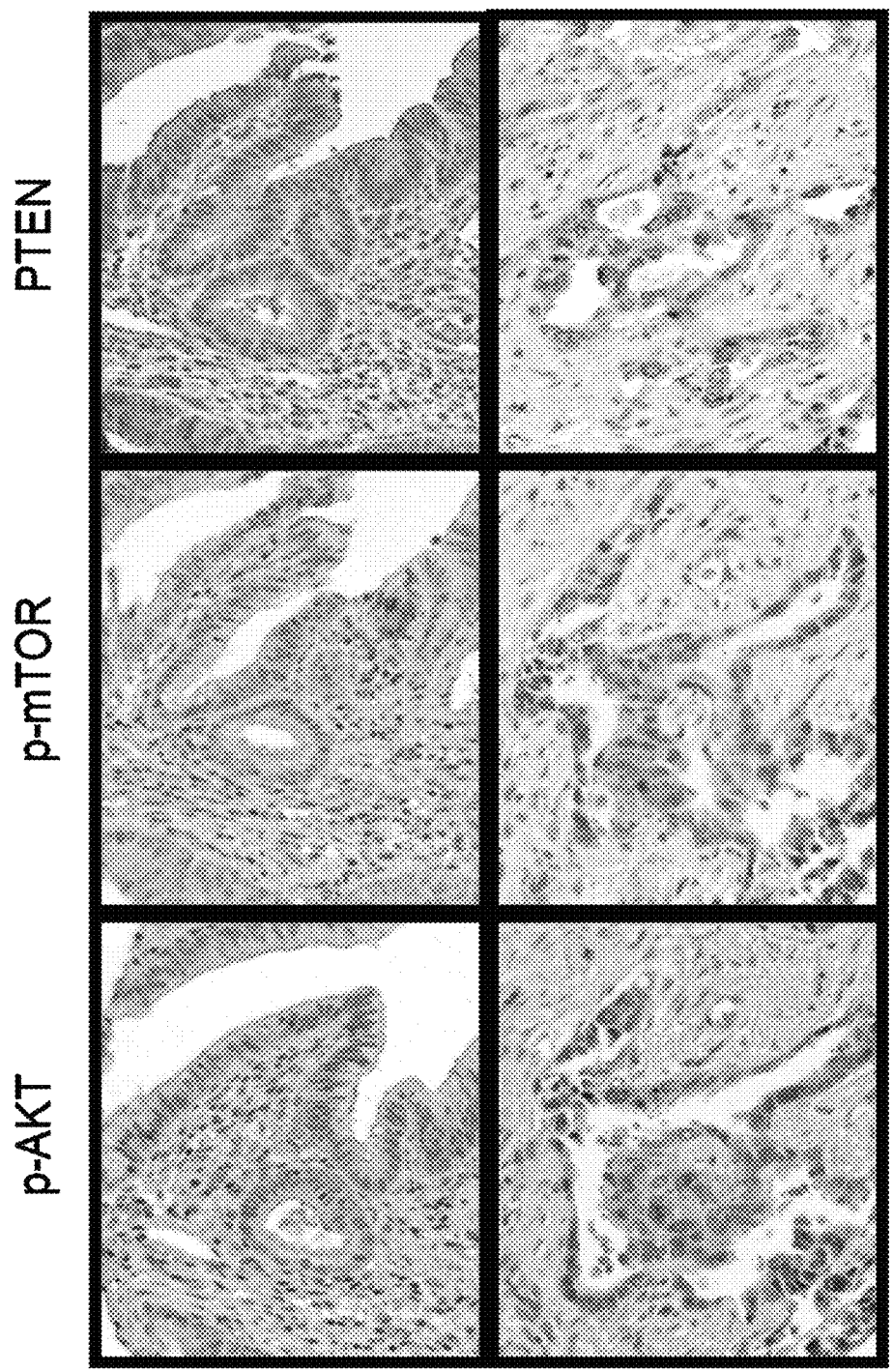

pAKT

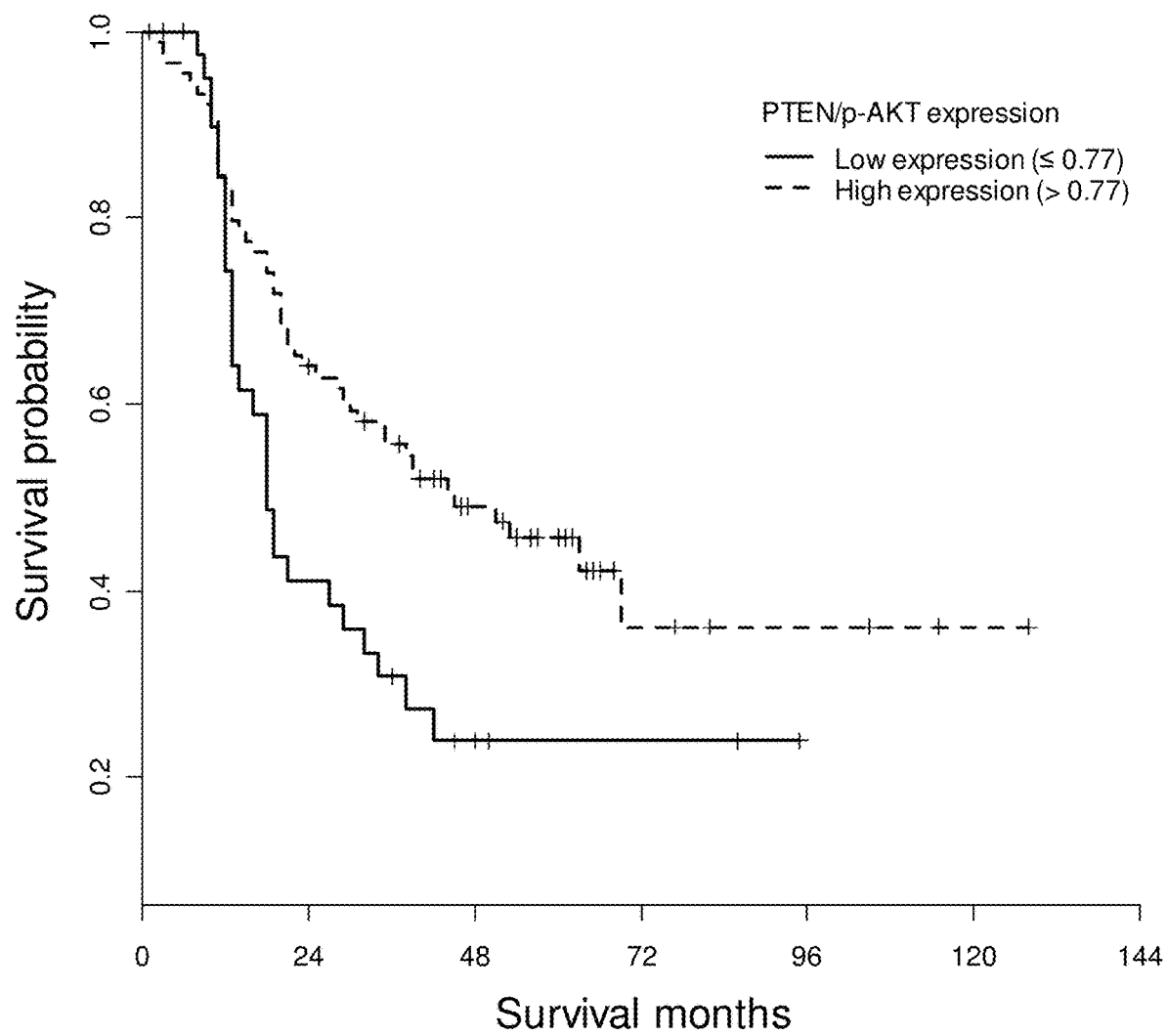

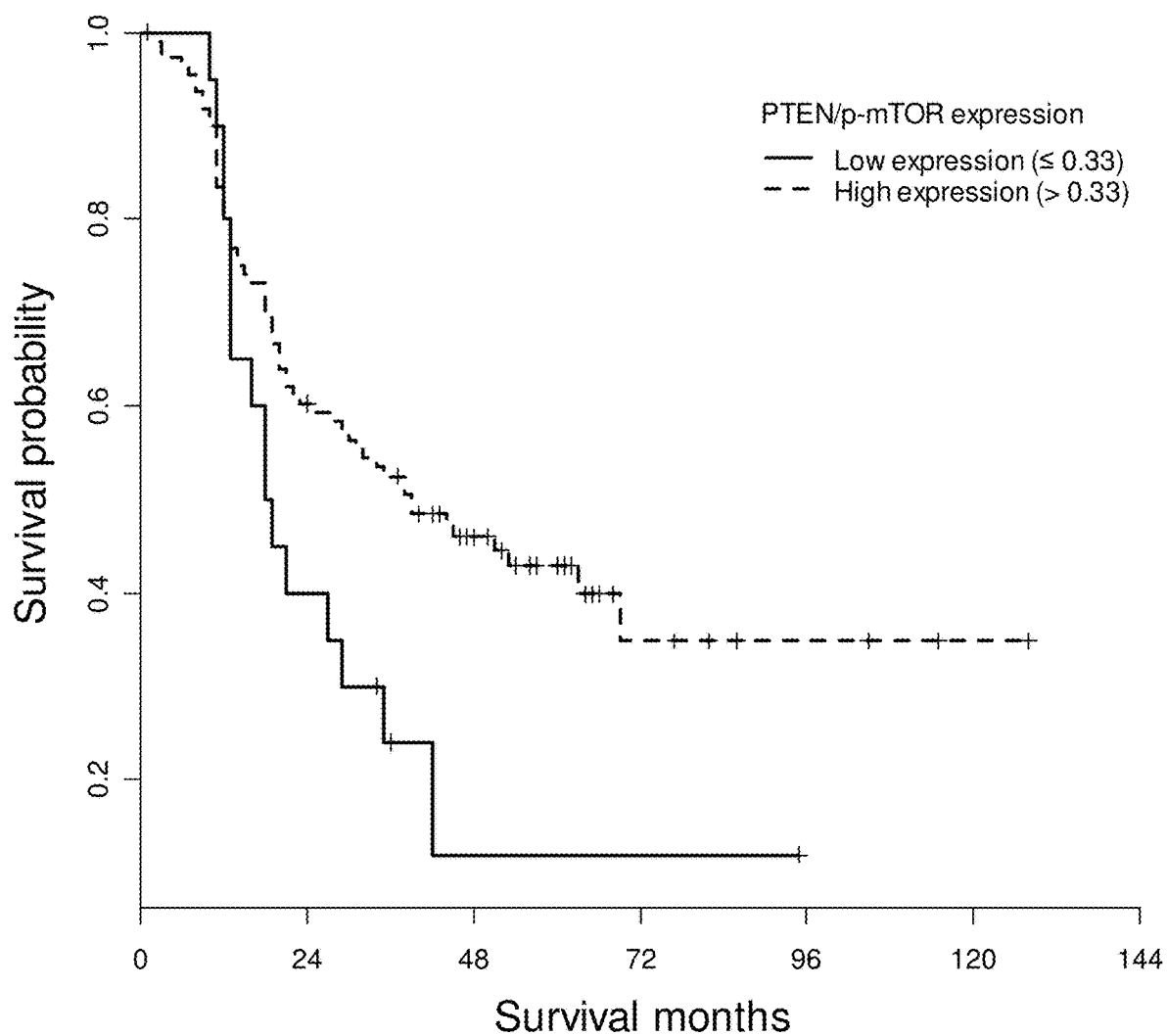

FIG. 6
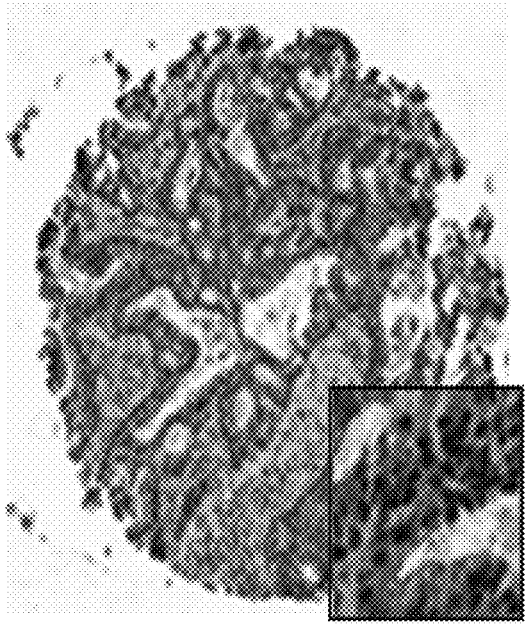
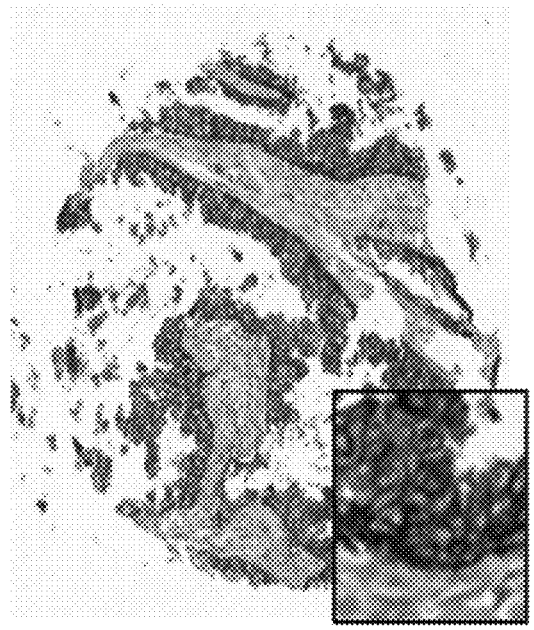

FIG. 8A
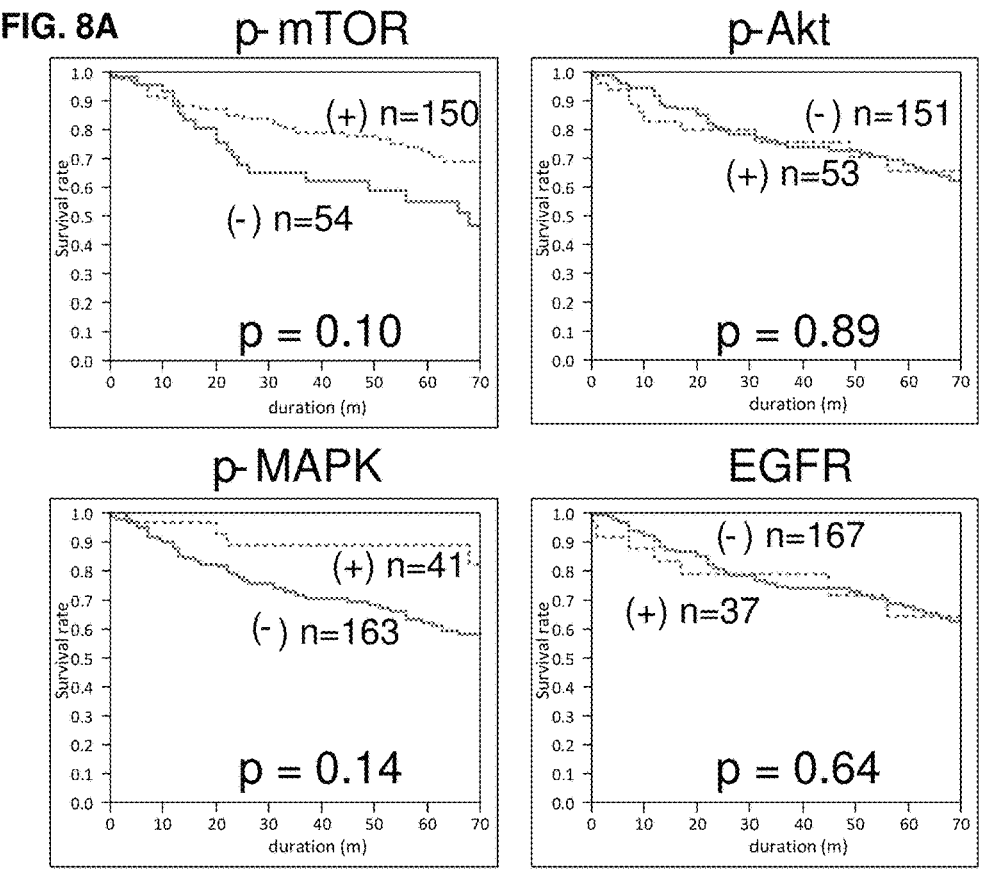
FIG. 8B
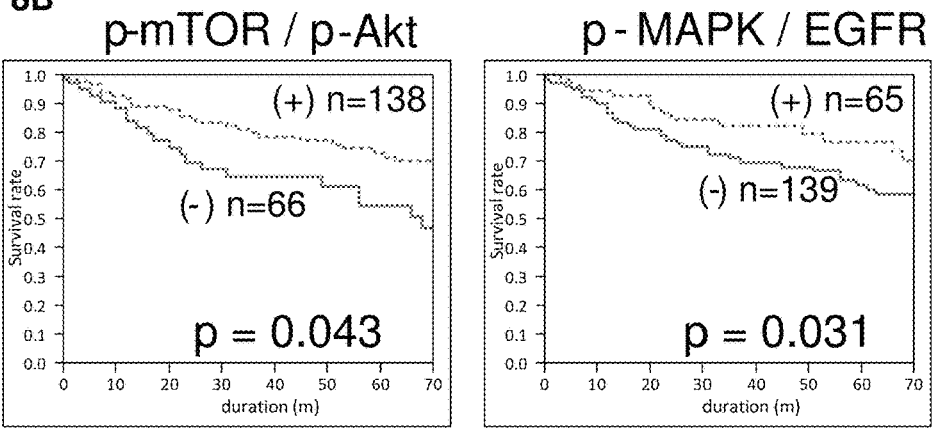
FIG. 8C +/+ , +/- , -/-
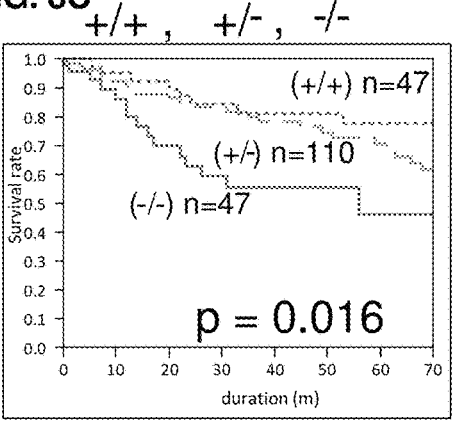
FIG. 8D Double Ratio
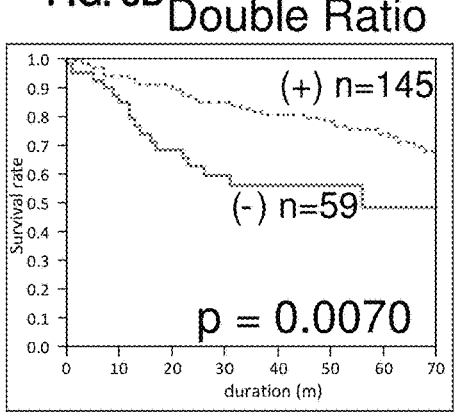

RATIO BASED BIOMARKERS AND METHODS OF USE THEREOF

REFERENCE TO RELATED APPLICATIONS

This is a continuation of co-pending U.S. application Ser. No. 15/349,991, filed Nov. 11, 2016, which is a continuation of U.S. application Ser. No. 13/144,474, filed Jul. 13, 2011, now abandoned, which is the U.S. National Stage of International Application No. PCT/ US2010/020944, filed Jan. 13, 2010, which was published in English under PCT Article 21(2); which in turn claims the benefit of U.S. Provisional Application No. 61/144,501, filed Jan. 14, 2009. The entire content of each of the listed prior applications is incorporated herein in its entirety.

FIELD OF THE DISCLOSURE

This disclosure relates to identification of ratio-based biomarkers for the detection, progression and prognosis of disease, such as cancer, in a subject. Also provided are similar methods for determination of the etiology or risk associated with a disease or condition. This disclosure also relates to methods of predicting survival probabilities and prognosis for a subject, and to methods of stratifying patient therapeutic regimes.

BACKGROUND

Tumors are characterized by their extensive heterogeneity and histopathologic variability. Currently, more than 250 malignant tumors and thousands of subtypes and histologic variants have been described in humans. Nevertheless, the classic pathologic criteria, such as tumor size, grade of malignancy, and metastatic dissemination, are generally the most relevant prognostic factors in cancer. In addition to the variability of histopathologic subtypes, molecular study of tumors is even more complex. In malignant tumors, at least six genetic alterations are believed to affect the main mechanisms of cellular transformation, including growth factor and cell signaling pathways, the cell cycle, apoptosis, and mechanisms implicated in cellular invasiveness, and angiogenesis (Hanahan and Weinberg, *Cell.* 100(1):57-70, 2000). Overall, more than 350 genes associated with tumors have been identified, representing more than 1% of the human genome (Futreal et al., *Nat Rev Cancer.* 4(3):177-83, 2004).

The aberrant behavior of cancer in part reflects an up-regulation of certain oncogenic signaling pathways that promote proliferation, inhibit apoptosis and enable the cancer to spread and evoke angiogenesis. Theoretically, it should be feasible to decrease the activity of these cancer-related signaling pathways, or increase the pathways that oppose them, with non-cytotoxic agents. However in practice, rates of success for the treatment of tumors or responsiveness of tumors after administration with such non-cytotoxic agents have been erratic. Several molecular targets have been identified as potential therapeutic targets for the treatment of solid tumors. Several of these molecular targets are proteins, found in cell signaling or growth factor pathways that are associated with the occurrence of cancer. Consequently, understanding the mechanisms of carcinogenesis and identifying biomarkers of increased risk would be of particularly great benefit in the early diagnosis and treatment of cancer. Identification of molecular targets in cell signaling and growth factor pathways associated with solid tumors, and the subsequent inhibition of the molecular target, is therefore a major treatment strategy for some cancers.

Currently, there is no simple answer to the question of which cellular proteins or signaling pathways are responsible for making a cell cancerous. For example, the Wnt signaling pathway, which normally plays a pivotal part in development, is often deregulated by mutation in cancer cells. Mutations in the gene for the retinoblastoma tumor suppresser protein, which is part of another signaling pathway, are also frequently associated with cancer. Given the complexity of the molecular networks that mediate cancer, with new entanglements being revealed, there is a compelling case for the generation of a comprehensive "circuitry" map of genetic interactions in the human genome.

In order to study expression profiles of proteins of interest, researchers have developed techniques such as Tissue Microarray (TMA) analysis and Laser Capture Microdissection (LCM). Generally, TMA analysis allows for the study of proteomics at the tissue level. For example, TMAs can be constructed from normal or diseased tissue, with a tissue section from each, being used to evaluate one or more proteins, such as the presence of absence or a disease marker protein, by immunochemical staining. Typically, TMA analysis requires a solid tissue sample, and antibodies that bind to formalin-fixed, paraffin embedded samples. One potential advantage of TMA analysis over other tissue-based proteomic profiling techniques is that multiple antigens can be assayed from a single tissue section simultaneously, and that the TMA retains the pathological structure of the tissue section from which it was derived. This information is particularly important when comparing or contrasting TMA expression profile results with pathology results of the same tissue section. Another commonly used technique to profile protein expression profiles is LCM. While LCM does provide the capacity to perform a directed western blot on a tissue section, the methodology is time consuming and does not provide a global expression view of a targeted protein. Immunohistochemistry while providing excellent localization, lacks quantification without sophisticated equipment such as high resolution tandem mass spectrometry, and lacks a normalization component.

Other "grind and bind" techniques for protein expression profiling provide quantification, but fail to provide a histomorphological perspective of protein expression. Given that pathology results are still often considered the "gold standard" for clinical diagnosis it remains preferable to develop techniques that work in conjunction with histomorphologic data. To overcome these disadvantages, a number of protein-based arrays have been developed and evaluated. Although these techniques are generally superior in expression profiling and quantification of protein changes associated with disease states, each has significant limitations. Therefore, there remains a need for methods for quantifying protein expression levels in normal and transformed or disease state samples, such as formalin-fixed, paraffin-embedded tissue sections, which also correlate with histomorphologic observations. Additionally, there remains a need for methods for detecting the presence of cancer in a sample, which methods can monitor progression of a cancerous disease and/or determine survival probabilities for a subject with cancer.

SUMMARY OF THE DISCLOSURE

Aspects of the present disclosure are directed to compositions, methods and apparatus for determining prognosis for a disease or condition, by identifying at least two proteins the expression (or loss of expression) of which is associated with the disease or condition in a sample from a subject with the disease or condition (or suspected to have or be susceptible to the disease or condition); quantifying the at least two disease/condition associated proteins in the sample; normalizing each associated protein; comparing the normalized value of the first disease/condition associated protein with the normalized value of the second disease/condition associated protein to obtain a biomarker indicator and; correlating the biomarker indicator with the prognosis of the subject. One specific example of this embodiment provides compositions, methods and apparatus for determining cancer prognosis (e.g., survival probability) of a subject with a cancer (e.g., a solid tumor, carcinoma or other classes of tumor) by identifying at least two cancer associated proteins in a sample from the subject; quantifying the at least two cancer associated proteins in the sample; normalizing each cancer associated protein; comparing the normalized value of the first cancer associated protein with the normalized value of the second cancer associated protein to obtain a biomarker indicator and; correlating the biomarker indicator with survival probability of the subject.

In further embodiments, compositions, methods and devices used for determining cancer survival probability of a subject are adapted for use with other diseases or conditions, as well as for examining the diagnosis, prognosis and/or prediction of response and determination of etiology or risk, of such other diseases or conditions. In many instances, embodiments are illustrated using cancer but it is understood that these are not to be viewed as restricted to cancer.

The present disclosure is further directed to methods for identifying cancer (or other disease or condition) associated proteins expressed in tissue samples, and for correlating the expression profile of the associated proteins with, for instance, various cancers, prognosis, or responses to therapies.

The present disclosure is further directed to methods for detecting the presence of cancer in a subject by determining levels of a first cancer associated protein and a second cancer associated protein from a biological sample from the subject; normalizing the first and second cancer associated protein contents against total cellular protein content from the biological sample; and comparing the normalized levels of the first and second cancer associated proteins with levels of the first and second cancer associated proteins in cells, tissues or bodily fluids measured in a normal control subject, wherein a change in the normalized levels of the first and second cancer associated proteins in the subject versus levels of the first and second cancer associated proteins measured in a normal control subject is associated with the presence of cancer in the subject.

In another embodiment, the disclosure provides a method for detecting the presence of a cancer in a subject by detecting in a biological sample from the subject the level of a first cancer associated protein, wherein the first cancer associated protein comprises PTEN, p-AKT, p-mTOR, p-MAPK, EGFR, HER2, HER3, or a combination of two or more thereof; and comparing the level of expression of the first cancer associated protein detected in the biological sample from the subject to a predetermined statistically significant cut-off value, wherein a change (e.g., decrease or increase) in the level of expression of the first cancer associated protein in the biological sample compared to a non-cancerous (e.g., non-transformed) sample is indicative of the presence of the cancer in the subject.

In a further embodiment the disclosure provides a method for detecting the presence of a cancer in a subject by calculating the level of p-AKT or p-mTOR expression in a sample from the subject; normalizing the level of p-AKT or p-mTOR expression against total cellular protein content from the sample; and comparing levels of normalized expression of p-AKT or p-mTOR expression in a control non-cancerous sample (for instance, a sample from a subject without cancer, or a sample from non-cancerous tissue in the same subject, etc.), wherein a statistically significant change in the level of p-AKT or p-mTOR expression in the subject's sample as compared to the normal non-cancerous sample is an indication of the presence of cancer in the subject. Similar methods are provided, wherein the cancer biomarkers involve measurement of p-MAPK, EGFR, HER2, and/or HER3.

Also provided is a method for identifying a survival-based cancer biomarker indicator, wherein the biomarker indicator comprises at least two cancer associated proteins from a cell signaling pathway associated with the cancer, and wherein the at least two cancer associated proteins are used to obtain the survival-based cancer biomarker indicator by calculating the content (level) of the first cancer associated protein in a sample, calculating the content (level) of the second cancer associated protein in the sample, normalizing the first cancer associated protein content against the total cellular protein content in the sample, and normalizing the second cancer associated protein content against the total cellular protein content in the sample, to obtain the survival-based cancer biomarker indicator.

In a further embodiment, the disclosure provides a method of determining relative cancer survival rates (or more generally prognosis) for a subject with a solid tumor by obtaining a biomarker indicator, the biomarker indicator being obtained by acquiring a solid tumor sample from the subject, extracting a first cancer associated protein from the solid tumor to produce a fraction comprising the first cancer associated protein, calculating the content of the first cancer associated protein in the fraction, normalizing the first cancer associated protein content against total cellular content in the fraction, extracting a second cancer associated protein from the solid tumor sample, calculating the content of the second cancer associated protein in the fraction, normalizing the second cancer associated protein content against total cellular protein content in the fraction, and correlating the normalized first cancer associated protein content against the normalized second cancer associated protein content to obtain a biomarker indicator, and comparing the biomarker indicator with relative survival rates, thereby determining the relative cancer survival rate for the subject with the solid tumor.

The present disclosure is further directed to methods for predicting relative cancer survival rates for a subject with a solid tumor by detecting the presence of an antibody to a tumor antigen in the solid tumor, wherein the tumor antigen involves increased expression of p-AKT and p-mTOR or decreased expression of PTEN as compared to a normal non-cancerous sample, thereby detecting the cancer in the subject, and correlating decreased expression of the tumor antigen in the subject as compared to a normal non-cancerous sample with a lower survival rate in the subject with the solid tumor. In another embodiment, the calculated tumor antigen involves increased HER2 relative to and/or along with decreased HER3 expression. Thus, the absolute value of the level of individual tumor (or other disease/condition) antigen is not necessarily determinative—rather, it is the relative amount compared to one or more other antigens that provides the predictive biomarker described herein.

In another embodiment, the disclosure provides a kit comprising a membrane array and detector molecules for the detection of cancer associated proteins in a sample, the array comprises a plurality of membranes, wherein each of the plurality of membranes has substantially a same affinity for the cancer associated proteins and containers comprise detector molecules for detecting the cancer associated proteins captured on each membrane, wherein the cancer associated proteins are selected from a group of cancers consisting of solid tumors, leukemia, multiple myeloma or lymphoma.

The instant disclosure identifies disease or condition associated biomolecules (such as proteins and nucleic acids) that can be used to detect, diagnose, identify subjects suitable for particular treatment regimes and provides prognosis information for such subjects. Optionally, the subject has cancer and the biomolecules are cancer associated biomolecules.

The instant disclosure also identifies a method for characterizing protein expression profiles in a sample and correlating the protein expression profiles with a survival-based cancer biomarker indicator for developing cancer, confirmation of the presence of a cancer, or the relative survival rates for a subject affected by the cancer.

The foregoing and other features and advantages will become more apparent from the following detailed description of a several embodiments which proceeds with reference to the accompanying figures.

BRIEF DESCRIPTION OF THE FIGURES

FIG. 1B is photograph of images showing immunohistochemical staining of p-AKT, p-mTOR, and PTEN protein in dysplasia and extrahepatic cholangiocarcinoma (EHCC) samples.

FIG. 2A shows EHCC cases had significantly higher expression of p-AKT than normal and dysplastic epithelia cases. FIG. 2B shows that EHCC cases had significantly higher expression of p-mTOR than normal and dysplastic epithelia cases.

FIG. 3A shows that cases with T1 classification had a significantly higher relative PTEN expression than those cases with other classifications. FIG. 3B is a box plot of relative expression of PTEN and its association with patients with duodenal invasion. FIG. 3B shows that patients with duodenal invasion had significantly less PTEN expression than those without duodenal invasion. FIG. 3C is a box plot of relative expression of PTEN and its association with patients with higher stage grouping. FIG. 3C shows that patients with higher stage grouping had significantly less PTEN expression than those with lower stage grouping. FIG. 3D is a box plot of relative expression of PTEN and its association with depth of tumor invasion. FIG. 3D shows that patients with less tumor cell invasion had a statistically greater PTEN expression than cases with deeper tumor cell invasion, but no statistical difference with those with depth of invasion between 0.5 cm and 1.2 cm.

FIG. 4 shows that patients with low PTEN expression have a lower relative survival rate than patients with high PTEN expression.

FIG. 5A-5B is a Kaplan-Meier survival analysis of EHCC cases according to PTEN/p-AKT or PTEN/p-mTOR expression. FIG. 5A shows a Kaplan-Meier survival analysis of EHCC cases according to PTEN/pAKT expression. FIG. 5A shows that low expressers of PTEN/pAKT have a significantly worse rate of survival than high expressers of PTEN/p-AKT expression. FIG. 5B is a Kaplan-Meier survival analysis of EHCC cases according to PTEN/p-mTOR expression. FIG. 5B shows that low expressers of PTEN/p-mTOR have a significantly worse rate of survival than high expressers of PTEN/p-mTOR expression.

FIG. 6 is a series of photographic images showing immunohistochemical staining of phosphorylated mammalian target of rapamycin (p-mTOR), phosphorylated protein kinase B (p-AKT; T308), phosphorylated mitogen-activated protein kinase (p-MAPK), and epidermal growth factor receptor (EGFR). EGFR showed membrane staining, whereas p-AKT, p-mTOR and p-MAPK showed cytoplasmic staining. Magnification: ×40; insets, ×100.

FIG. 8A-8D shows Kaplan-Meier survival analysis of non-small cell lung cancer patients. FIG. 8A illustrates the correlation of single each antibody expression with patients' outcome. FIG. 8B illustrates the correlation of the ratio p-mTOR to p-AKT (p-mTOR/p-AKT) and the ratio of p-MAPK to EGFR (p-MAPK/EGFR) with patients' outcome. FIG. 8C illustrates t correlation of three groups; both of the ratios were high (+/+), either of them were high (+/−), both of them were low (−/−). FIG. 8D illustrates the correlation of Double ratio with patients' outcome.

DETAILED DESCRIPTION

Figure 1A:
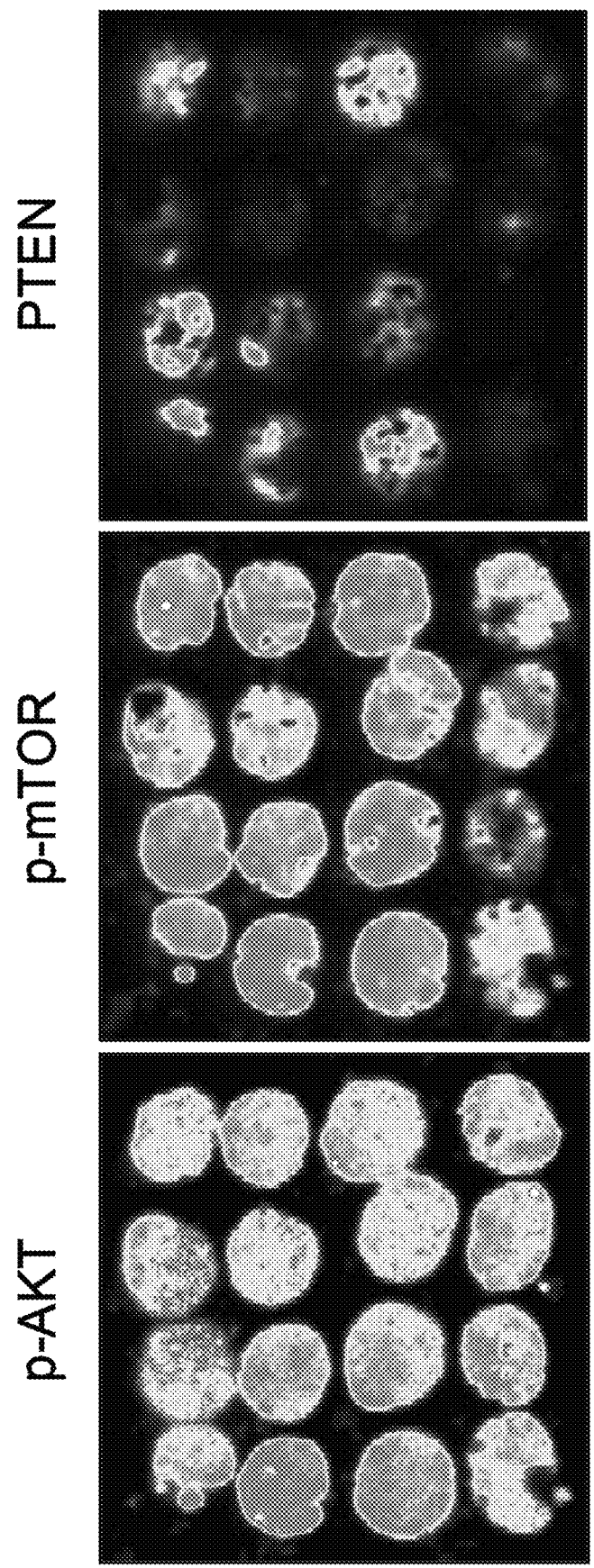
FIG. 1A is a photograph of images showing phospho-AKT (p-AKT), phospho-mTOR (p-mTOR), and PTEN expression by multiplex tissue immunoblotting (MTI).

I. Abbreviations
   eIF4E: eukaryotic initiation factor 4E
   AKT: protein kinase B
   BIRC5: survivin protein
   CEA: carcinoembryonic antigen
   CK: pan-cytokeratin
   COX2: cyclooygenase-2
   EGFR: epidermal growth factor receptor
   EHCC: extrahepatic cholangiocarcinoma
   FFPE: formalin-fixed, paraffin-embedded
   HER: human epidermal growth factor receptor
   HSP: heat shock protein
   IC: immunohistochemistry
   LCM: laser capture microdissection
   MAPK: mitogen-activated protein kinase
   MTI: multiplex tissue immunoblotting
   mTOR: mammalian target of rapamycin
   mTORC: mammalian target of rapamycin complex
   p-AKT: phosphorylated AKT
   p-EGFR: phosphorylated EGFR
   PI3K: phosphatidyl inositol 3 kinase
   pMAPK: phosphorylated mitogen-activated protein kinase p-mTOR: phosphorylated mTOR
PSA: prostate specific antigen
PTEN: phosphatase and tensin homolog deleted on chromosome 10
S6: ribosomal protein kinase S6
TG2: transglutaminase 2
TMA: tissue micro array(s)

II. Explanation of Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Array: An arrangement of molecules, particularly biological macromolecules (such as proteins or polypeptides) or biological samples (such as cells or tissue sections), in addressable locations on or in a substrate. The array may be regular (arranged in uniform rows and columns, for instance) or irregular (such as a tissue section). The number of addressable locations on the array can vary, for example from a few (such as two) to more than 50, 100, 200, 500, 1000, 10,000, or more. A "microarray" is an array that is miniaturized so as to require or be aided by microscopic examination for evaluation or analysis.

Within an array, each arrayed sample ("feature") is addressable, in that its location can be reliably and consistently determined within the at least two dimensions of the array. Thus, in ordered arrays the location of each sample/feature within the array is assigned to the sample at the time when it is applied to the array, and a key may be provided in order to correlate each location with the appropriate target or feature position. Often, ordered arrays are arranged in a symmetrical grid pattern, but samples could be arranged in other patterns (e.g., in radially distributed lines, spiral lines, or ordered clusters). Addressable arrays usually are computer readable, in that a computer can be programmed to correlate a particular address on the array with information about the sample at that position (e.g., hybridization or binding data, including for instance signal intensity). In some examples of computer readable formats, the individual features in the array are arranged regularly, for instance in a Cartesian grid pattern, which can be correlated to address information by a computer.

Feature(s) within an array may assume many different shapes. Thus, though the term "spot" is used herein, it refers generally to a localized placement of molecules or cells, and is not limited to a round or substantially round region. For instance, substantially square regions of application can be used with arrays encompassed herein, as can be regions that are, for example substantially rectangular, triangular, oval, irregular, or another shape.

In certain example arrays, one or more features will occur on the array a plurality of times (e.g., twice, though more are also contemplated) to provide internal controls.

In other examples, the array will replicate the position of features in a sample, for example, the location of markers of interest in a tissue section. In which case, the array markers of interest will be transferred from the tissue section to another medium, such as a membrane, for example a nitrocellulose membrane, wherein the features are evaluated.

Binding or interaction: An association between two substances or molecules. The arrays are used to detect hybridization/binding or other interaction of a labeled molecule (termed a "probe" herein) with an immobilized target molecule in the array. A probe "binds" to a target molecule in a feature on an array if, after incubation of the probe (usually in solution or suspension) with or on the array (or a slice of the array) for a period of time (usually 5 minutes or more, for instance 10 minutes, 20 minutes, 30 minutes, 60 minutes, 90 minutes, 120 minutes or more), a detectable amount of the probe associates with a feature of the array to such an extent that it is not removed when the array is washed with a relatively low stringency buffer. Appropriate buffers for washing TMAs will depend on the constituents of the features of the array, and thus may be those used in washing nucleic acid hybridization systems (e.g., higher salt (such as 3× or higher saline-sodium citrate (SSC) buffer) room temperature washes), protein interaction systems (e.g., 100 mM KCl), and so forth.

Washing can be carried out, for instance, at room temperature, but other temperatures (either higher or lower) can also be used. Probes will bind target molecules to different extents, and the term "bind" encompasses both relatively weak and relatively strong interactions. Thus, some binding will persist after the array is washed in a way that is appropriate to remove the probe molecule. For instance in a lower salt buffer (such as about 0.5 to about 1.5×SSC), 55-65° C. washes can be used for nucleic acid probes, or a higher salt buffer (e.g., 500 mM or 1000 mM KCl, tris-buffered saline with Tween® 20 (TBST)) for protein probes, and so forth.

Where the probe and target molecules are nucleic acids, binding of the probe to a target can be discussed in terms of the specific complementarity between base sequences of the probe and the target nucleic acid. Where either the probe or the target is a protein, specificity of binding and binding affinity can be discussed.

The term "binding characteristics of an array for a particular probe" refers to the specific binding pattern (and optionally the specific relative signal intensities) that forms between the probe and the array after excess (unbound or not specifically bound) probe is washed away. This pattern (which may contain no positive signals, some or all positive signals, and will likely have signals of differing intensity) conveys information about the binding affinity of that probe for molecules within the spots or tissue sections of the array, and can be decoded by reference to the key of the array (which lists the addresses of the spots on the array surface or identifies the probe's potential binding partner). The relative intensity of the binding signal from individual features in many instances is indicative of the relative level in a particular feature on the array of the target that binds to or interacts with the probe. Quantification of the binding pattern of an array/probe combination (under particular probing conditions) can be carried out using any of several existing techniques, including scanning the signals' intensities into a computer for calculation of relative density of each spot.

Biomarker Indicator: A molecular-biology based diagnostic and/or prognostic indication that disease may be present, may develop, and the like. In embodiments of the instant disclosure, the biomarker indicator is a prognostic and/or diagnostic indicator of the development of a disease such as cancer, and associated rate of survival (or other prognosis) for a subject with the cancer. Biomarker indicators are determined by calculating the content/level of at least two disease/cancer associated proteins in a sample, and normalizing the content of the two or more associated proteins relative to total cellular protein content in the sample.

Optionally, in various embodiments the biomarker indicator includes the ratio (quotient) of the level of one protein to another, the ratio of two proteins to one or more protein to two, the sum of the levels of two proteins, or the sum of the two or more ratios of protein levels, the difference between the levels of two (or more) proteins or the ratios of proteins, the mathematical product (that is, result of multiplying together) of the levels or two or more proteins or ratios thereof, and so forth.

Cancer Associated Protein: A substance produced in tumor cells that trigger an immune response in the host. As used herein, the term Cancer Associated Protein is used interchangeably with Tumor Antigen. The substance may be broadly categorized based on the substance's expression pattern and/or location of expression. For example, Tumor-Specific Antigens are present only in tumor cells and are not found in normal/healthy cells. Tumor-Associated Antigens are present on some tumor cells and also present on some normal/healthy cells. The above definition also encompasses the terms "Cancer-Specific Markers" and "Tissue-Specific Markers". Cancer-Specific markers are related to the presence of a certain cancerous tissue. One example of a Cancer-Specific Marker is carcinoembryonic antigen (CEA), a blood-borne protein first noted to be produced by tumors of the gastrointestinal system. Tissue-Specific Markers are related to specific tissues which have developed cancer. Generally speaking, these substances are not specifically related to the tumor, and may be present at elevated levels when no cancer is present. Unlike Cancer-Specific markers, elevated levels of Tissue-Specific Markers point to a specific tissue being at fault. For example, highly elevated levels of PSA (Prostate Specific Antigen) are often associated with the development of prostate cancer.

Freezing: The term "freezing" and "frozen" as they are used herein refers to the solidification of a liquid sample, to a point of solidity (rigidity) sufficient that it can be sectioned or sliced. Freezing usually occurs at a temperature at or below the freezing temperature of water, but where the sample contains constituents other than water, the "freezing" (solidification) point may be substantially different from 0° C. In some embodiments of the instant disclosure a liquid biological sample such as sera, may be frozen in an embedding compound so that the sample can be sectioned, sliced, stained and evaluated.

Fluorophore: A chemical compound, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540$\lambda$. Red fluorophores, for example Texas Red, Cy5 and tetramethylrhodamine, are characterized by their emission at wavelengths generally in the range of 590-690$\lambda$.

Examples of specific fluorophores are provided in U.S. Pat. No. 5,866,366 to Nazarenko et al., and include for instance: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron .RTM. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include GFP (green fluorescent protein) and variants and derivatives thereof, Lissamine™, diethylaminocoumarin, fluorescein chlorotriazinyl, naphthofluorescein, 4,7-dichlororhodamine and xanthene and derivatives thereof. Other fluorophores known to those skilled in the art may also be used in the methods described herein.

High-throughput genomics or proteomics: Application of genetic data such as genes or proteins with various techniques such as microarrays or other genomic technologies to rapidly identify large numbers of genes or proteins, or distinguish their structure, expression or function from normal or abnormal cells or tissues.

Isolated: An "isolated" biological component (such as a nucleic acid molecule, protein or organelle) has been substantially separated or purified away from other biological components in the cell of the organism in which the component naturally occurs, i.e., other chromosomal and extrachromosomal DNA and RNA, proteins and organelles, or from other components in the reaction mixture used to generate the molecule (if it is synthesized in vitro). Nucleic acids and proteins that have been "isolated" include nucleic acids and proteins purified by standard purification methods. The term embraces nucleic acids and proteins prepared by recombinant expression in a host cell as well as chemically synthesized molecules.

Label: Detectable marker or reporter molecules, which can be attached to nucleic acids or proteins, for example probe molecules. Typical labels include fluorophores, radioactive isotopes, ligands, chemiluminescent agents, metal sols and colloids, and enzymes. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987).

Malignant: A term describing cells that have the properties of dysplasia, anaplasia, invasion and metastasis.

Membrane: a term describing a thin sheet of natural or synthetic material that is porous or otherwise at least partially permeable to biomolecules.

Neoplasia: Abnormal growth of cells, including benign and malignant neoplasms.

Probe: A molecule that may bind to or interact with one or more targets (e.g., biological macromolecules or cells). A probe, as the term is used herein, can be any molecule that is used to challenge ("probe," "assay," "interrogate" or "screen") a TMA, MTI, LCM, or other assay, in order to determine the binding, activity, or interaction characteristics of the arrayed target(s) with that probe molecule. In specific embodiments, probes may be from different and varied molecular classes. Such classes are, for instance, nucleic acids (such as single or double stranded DNA or RNA), oligo- or polypeptides (such as proteins, for instance antibodies, protein fragments including domains or sub-domains, and mutants or variants of naturally occurring proteins), or various types of other potential polypeptide-binding molecules. Such other molecules are referred to herein generally as ligands (such as drugs, toxins, venoms, hormones, co-factors, substrates or reaction products of enzymatic reactions or analogs thereof, transition state analogs, minerals, salts, and so forth).

The term probe, as used herein, also encompasses substrates and/or assays systems used to assess the activity of a target within a feature of the array. Thus, it is contemplated that TMA sections can be assayed for the activity of a protein in one or more features using a probe that is a substrate of that protein (which substrate may contain a label, as discussed herein), or a probe that is a reporter system that interacts with the target protein to produce a detectable signal.

Usually, a probe molecule for use in probing a TMA is detectable or produces a detectable product. Probes can be detectable based on their inherent characteristics (e.g., immunogenicity, color, fluorescence) or can be rendered detectable by being labeled with an independently detectable tag or label. The tag may be any recognizable feature that is, for example, microscopically distinguishable in shape, size, color, optical density, etc.; differently absorbing or emitting of light; chemically reactive; magnetically or electronically encoded; or in some other way detectable. Specific examples of tags are fluorescent or luminescent molecules that are attached to the probe, or radioactive monomers or molecules that can be added during or after synthesis of the probe molecule. Other tags may be immunogenic sequences (such as epitope tags) or molecules of known binding pairs (such as members of the strept/avidin:biotin system). Additional tags and detection systems are known to those of skill in the art, and can be used in the disclosed methods.

Though in many embodiments a single type of probe molecule (for instance one protein) at a time will be used to assay the array, in some embodiments, mixtures of probes will be used, for example, mixtures of two proteins or two nucleic acid molecules. Such co-applied probes may be labeled with different tags, such that they can be simultaneously detected as different signals (e.g., two fluorophores that emit at different wavelengths or two gold particles of different sizes).

In specific embodiments, one of these co-applied probes will be a control probe (or probe standard), which is designed to hybridize to a known and expected sequence in one or more of the spots on the array.

In some provided examples of TMA and methods of probing them, the probe is a heterogeneous mixture, for instance a heterogeneous mixture of nucleic acid molecules or proteins. For example, a probe may be a pool of proteins (for instance, a protein preparation from a cell sample) that can be used as a probe to assay a TMA that contains known proteins (e.g., known antibodies or other proteins), and a signal at a locus on the array interpreted as an indication that the pool contains one or more proteins that interact with the target in that locus (e.g., contains an antigen the target antibody at that locus has affinity for).

Probe standard: A probe molecule for use as a control in analyzing an array. Positive probe standards include any probes that are known to interact with at least one of the targets of the array. Negative probe standards include any probes that are known not to specifically interact with at least one target of the array. Probe standards that may be used in any one system include molecules of the same class as the test probe that will be used to assay the array. For instance, if the array will be used to examine the interaction of a protein with polypeptides in the array, the probe standard can be a protein or oligo- or polypeptide.

In some examples of TMA, for instance certain arrays that contain mixtures of nucleic acids or proteins in the features, a control probe sequence can be designed to hybridize with a so-called "housekeeping" gene. For instance, the housekeeping gene is one which is known or suspected to maintain a relatively constant expression level (or at least known to be positively expressed) in a plurality of cells, tissues, or conditions. Many of such "housekeeping" genes are well known in the art; specific examples include histones, β-actin, or ribosomal subunits (either mRNA encoding for ribosomal proteins or rRNAs). Housekeeping genes can be specific for the cell type being assayed, or the species or Kingdom from which the sample being tested in the array has been produced.

In some instances, as in certain embodiments of the kits that are provided herein, a probe standard will be supplied that is unlabeled. Such unlabeled probe standards can be used in a labeling reaction as a standard for comparing labeling efficiency of the test probe that is being studied. In some embodiments, labeled probe standards will be provided in the kits.

Probing: As used herein, the term "probing" refers to incubating an array with a probe molecule (usually in solution) in order to determine whether the probe molecule will bind to, hybridize or otherwise interact with molecules immobilized on the array. Synonyms include "interrogating," "challenging," "screening" and "assaying" an array. Thus, a TMA is said to be "probed" or "assayed" or "challenged" when it is incubated with a probe molecule (such as a labeled or otherwise detectable polypeptide, nucleic acid molecule, or ligand, or a positive, single-stranded and detectable nucleic acid molecule that corresponds to a feature of interest).

Protein/Polypeptide: A biological molecule expressed by a gene or other encoding nucleic acid, and comprised of amino acids. More generally, a polypeptide is any linear chain of amino acids, usually about 50 or more amino acid residues in length, regardless of post-translational modification (e.g., glycosylation or phosphorylation).

Examples of TMA include a plurality of polypeptide samples (targets) placed at addressable locations within an array substrate (e.g., a block of embedding material). The polypeptide at each location can be referred to as a target polypeptide, or target polypeptide sample.

In certain embodiments, polypeptides are deposited into the array in a substantially native configuration, such that at least a portion of the individual polypeptides within the locus is in a native configuration. Such native configuration-polypeptides are capable of binding to or interacting with molecules in solution that are applied to the surface of the array section in a manner that approximates natural intra- or intermolecular interactions. Thus, binding of a molecule in solution (for instance, a probe) to a target polypeptide immobilized in an array will be indicative of the likelihood of such interactions in the natural situation (i.e., within a cell). In some embodiments the polypeptides in features of a Tissue Micro Array retain function and therefore can be assayed for an activity.

One of the benefits of the provided system of protein analysis using TMA is maintaining samples, particularly protein samples, at or below freezing during the preparation of the block or tissue section. Additionally, another benefit of the TMA as a substrate is that the block or section, such as formalin fixed, paraffin embedded tissue, can be analyzed for features, and that the features can be quantified as a direct replicate of the block or section. By retaining the histomorphological structure of the section the TMA can be directly compared to, or confirmed by pathology.

Protein purification: Polypeptides for use in the present disclosure can be purified by any of the means known in the art. See, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982.

Proteomics: Global, whole-cell analysis of gene expression at the protein level, yielding a protein profile for a given cell or tissue. The comparison of two protein profiles (proteomes) from cells that have been differently treated (or that are otherwise different, for instance genetically) provides information on the effects the treatment or condition (or other difference) has on protein expression and modification. Subproteomics is analysis of the protein profile of a portion a cell, for instance of an organelle or a protein complex. Thus, a mitochondrial proteome is the profile of the protein expression content of a mitochondrion under certain conditions. Proteomic analysis is increasingly being performed using peptide and protein arrays; such arrays are reviewed in Emili and Cagney (*Nat. Biotech.* 18:393-397, 2000).

Purified: The term purified does not require absolute purity; rather, it is intended as a relative term. Thus, for example, a purified nucleic acid preparation is one in which the specified nucleic acid is more enriched than the nucleic acid is in its generative environment, for instance within a cell or in a biochemical reaction chamber. A preparation of substantially pure nucleic acid may be purified such that the desired nucleic acid represents at least 50% of the total nucleic acid content of the preparation. In certain embodiments, a substantially pure nucleic acid will represent at least 60%, at least 70%, at least 80%, at least 85%, at least 90%, or at least 95% or more of the total nucleic acid content of the preparation. Similarly, a preparation of substantially pure protein may be purified such that the desired protein represents at least 50% of the total protein content of the preparation. In certain embodiments, a substantially pure protein will represent at least 60%, at least 70%, at least 80%, at least 85%, at least 90%, or at least 95% or more of the total protein content of the preparation.

Stripping: Bound probe molecules can be stripped from an array, for instance a protein Tissue Micro Array, in order to use the same array for another probe interaction analysis (e.g., to determine the level of a different protein in the arrayed samples, particularly where the arrayed samples contain mixtures of proteins). Any process that will remove substantially all of the first probe molecule from the array, without also significantly removing the immobilized nucleic acid mixtures of the array, can be used. By way of example only, one method for stripping a protein array is by washing it in stripping buffer (e.g., 1 M $(NH_4)_2SO_4$ and 1 M urea), for instance at room temperature for about 30-60 minutes. By way of example only, one method for stripping an array containing nucleic acids is by boiling it in stripping buffer (e.g., very low or no salt with 0.1% SDS), for instance for about an hour or more. Usually, the stripped array will be equilibrated, for instance in a low stringency wash buffer, prior to incubation with another probe molecule.

Sample: A sample, such as a biological sample, is a sample obtained for example, from a subject. As used herein, biological samples include all clinical samples useful for detection of cancer in subjects, including, but not limited to, cells, tissues, and bodily fluids, such as: blood; derivatives and fractions of blood, such as serum; biopsied or surgically removed tissue, including tissues that are, for example, unfixed, frozen, fixed in formalin and/or embedded in paraffin; swabs; skin scrapes; urine; sputum; cerebrospinal fluid; prostate fluid; pus; or bone marrow aspirates. In a particular example, a sample includes a solid tumor biopsy obtained from a human subject, such as an EHCC biopsy. In another particular example, a sample includes cells, for example a group of cells collected or archived as part of a tissue section.

Samples may come from human or non-human animals, as well as in vitro grown cell lines or xenografts.

Subject: Living, multicellular vertebrate organisms, a group that includes both human and veterinary subjects, for example, mammals, birds, and primates.

Target: As used herein, individual molecules, cells, tissue sections or mixtures that are placed onto a TMA, TMI, LCM, or other platform for analysis, are referred to as targets. Targets on a single array can be derived from one to several thousand different samples, such as cell or tissue types (more generally, from a plurality of specimens). In certain embodiments of the arrays and methods described herein, the target feature on the array contains a heterogeneous mixture of molecules that proportionately reflects the levels of the starting (source) material from which the molecules are derived; such arrays can be used to comparatively examine the level of constituents in an array feature. Thus, in specific examples, the features of the array contain mRNA or mRNA-derived molecules (e.g., aRNA, cRNA or cDNA) that are present in proportionate amounts to the nucleic acids they represent in the starting sample (e.g., tissue) from which the mRNA was extracted to generate the feature. Similarly, some arrays will include features that contain heterogeneous mixtures of proteins that reflect the levels (e.g., proportionate levels) of those proteins in a starting material, such as a tissue sample.

In general, a target on the array is discrete, in that signals from that target can be distinguished from signals of neighboring targets, either by the naked eye (macroarrays) or by scanning or reading by a piece of equipment or with the assistance of a microscope (microarrays).

Tissue Microarrays (TMA): An array of samples, such as biological samples, placed into a block of substrate (such as embedding compound), which loaded block is then sliced (sectioned) to produce a cross-section of the biological sample, each containing a portion of the sample in the block. The samples "freeze" into the block of substrate, such that the loaded block can be sectioned and will maintain the portions of sample in addressable locations that correlate to the locations of the samples in the loaded block. Examples of TMA include protein Tissue Micro Arrays (in which the samples contain one or more known or unknown proteins), and nucleic acid Tissue Micro Arrays (in which the samples contain one or more known or unknown nucleic acids). Additional examples of Tissue Microarrays are discussed herein.

In some embodiments, Tissue Microarrays are constructed as a block containing substantially columnar samples contained in wells in the block. Once one or more samples are loaded into wells in the block, it can be sliced (sectioned) to provide a plurality of identical or substantially identical individual arrays. The individual arrays can be used for parallel analysis of the same set of features, for instance with different probes or under different conditions. In order to maintain substantially similar feature size and placement on sequential sections from a single block, the wells in the block may be formed perpendicular to the surface from which sections are removed. However other configurations of the array are possible. For example, the columns may be non-parallel but will vary in a predictable relationship to one another, such that the position at which each column intersects a section can be predicted.

The shape of the Tissue Micro Array substrate itself is essentially immaterial, though it is usually substantially flat on at least one side and may be rectangular or square in general shape.

In other embodiments, Tissue Micro Arrays are constructed as blocks that contain a biological sample, for example a tissue sample, in which the biological sample in the block is transferred to a stack of replicate membranes, which can be probed using standard immunohistochemistry techniques. In this instance, the block provides a level of histomorphological correlation with the original biological sample in the block.

Tumor: A neoplasm that may be either malignant or non-malignant. "Tumors of the same tissue type" refers to primary tumors originating in a particular organ (such as breast, prostate, bladder or lung). Tumors of the same tissue type may be divided into tumors of different sub-types (a classic example being bronchogenic carcinomas (lung tumors), which can be an adenocarcinoma, small cell, squamous cell, or large cell tumor). Recurrent and metastatic tumors are also contemplated.

Tumor Classification: The TNM Classification of Malignant Tumors (TNM) is a cancer staging system that describes the extent of cancer in a subject's body. T describes the size of the tumor and whether it has invaded nearby tissue, N describes regional lymph nodes that are involved, and M describes distant metastasis. TNM was developed and is maintained by the International Union Against Cancer (UICC) to achieve consensus on one globally recognized standard for classifying the extent of spread of cancer. In 1987, the UICC and the American Joint Committee on Cancer (AJCC) staging systems were unified into a single staging system.

Watchful-Waiting Protocol: A watchful-waiting protocol is a wait-and-see clinical approach for the treatment of disease, for example, prostate cancer. The subject may get better (or not get worse) without treatment; if the condition worsens, the physician managing the subjects' health will decide what to do next, for example a radical prostatectomy.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise, and the term "comprising" means "including." Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Ratio Based Biomarkers and Methods of Use Thereof

Generally, the methods disclosed herein require the detection of at least one cancer associated protein. In other embodiments, the methods disclosed herein require the detection of at least two, three, four, five, or more, cancer associated proteins. In particular embodiments, the cancer associated protein comprises a cell signaling or growth factor pathway protein, or another cancer associated molecule such as a cytokeratin, a protein associated with cytoskelatin or a protein associated with localization of another protein (such as adaptors and so forth), have utility in cancer as well. In several embodiments, the methods include detecting the presence of at least one cancer associated protein in a biological sample, such a tissue section or biopsy. In some embodiments, identifying the presence of the at least one cancer associated proteins in a sample determines if a particular therapeutic regime is successful as a means to increase the relative survival rate (and more generally, improve the prognosis) of a subject with a cancer.

In a further embodiment, identifying the presence of at least one cancer associated protein associated with a cell signaling pathway or growth factor pathway in a sample can determine if a particular therapeutic regime is successful as a means to increase the prognosis or relative survival rate of a subject with a cancer. Thus, the methods disclosed herein can be used to determine if preventative treatment should be administered to a subject at risk for developing cancer, or if a treatment should be administered to a subject to prevent the progression of existing pathological structures, such as from early stage to a more advanced stage of cancer. The methods disclosed herein can also be used to confirm a diagnosis of cancer in the subject.

Methods for determining cancer survival probability of a subject with cancer are provided herein. In particular, methods for predicting relative survival rate for a subject with a solid tumor, such as a carcinoma, as well as methods for predicting relative survival rate for a subject with EHCC are disclosed. The methods disclosed can also be used to detection cancer in a subject such as, but not limited to, solid tumors, such as carcinomas of breast, lung, prostate, colon, gastric, liver, thyroid, kidney, bile duct and renal tissue. In particular embodiments, the methods of the instant disclosure can be used to detect the presence of EHCC in a subject. In a further embodiment, the methods disclosed herein can be used to detect the presence of a hematopoietic cancer such as lymphoma, leukemia or multiple myeloma in a biological sample. In another embodiment, disclosed herein are methods for determining relative survival rates for a subject with a hematopoietic cancer such as lymphoma, leukemia or multiple myeloma.

In another embodiment, the methods disclosed can also be used to determine the risk of developing cancer, such as, but not limited to carcinoma. The methods are also useful as a prognostic tool to evaluate subjects with cancer prior to treatment and as a means for determining a therapeutic regimen for a subject that is anticipated to increase the relative survival rate of the subject with cancer.

In one embodiment, the methods are useful not only in determining risk, but for pathological confirmation of cancer associated proteins. For example, in embodiments that utilize tissue blocks as the sample source, the detection of cancer associated proteins can be correlated with a histo-morphological structure in the original tissue block sample. The methods disclosed herein can also be used to detect a cancer or determine the risk of developing a cancer based on the protein expression profile of the biological sample tested.

In a general embodiment, the methods include obtaining a sample from a subject, identifying at least two cancer associated proteins in the sample; quantifying the content of the two cancer associated proteins; normalizing the content of the two cancer associated proteins to obtain a normalized value for each cancer associated protein and comparing the normalized value of the first cancer associated protein with the normalized value of the second cancer associated protein to obtain a biomarker indicator, and correlating the biomarker indicator with survival probability of the subject with the cancer.

In another embodiment, the instant disclosure identifies a survival-based cancer biomarker comprising at least two cancer associated proteins, wherein the at least two cancer associated proteins are proteins from a cell signaling pathway associated with the cancer, and wherein the two cancer associated proteins are used to obtain a biomarker indicator that can be used to determine relative survival rates of a subject with cancer.

In a further embodiment, the instant application discloses a method of detecting the presence of a cancer in a subject, the methods generally comprise determining the level of a first and second cancer associated protein and normalizing the presence of the cancer associate protein to obtain a biomarker indicator that correlates with the present of cancer.

The methods as disclosed herein include selecting a subject in need of detecting the presence of the cancer associated protein, and obtaining a sample including the cancer associated protein from this subject. For example, a subject can be selected who is suspected to have a cancer, such as breast, colon, stomach (gastric), cervical, brain, head and neck, prostate, biliary tract or lung cancer. In another example, a subject can be selected that is symptomatic with a cancer. In a further example, the subject can be a subject who has been diagnosed with a carcinoma, such as, but not limited to bile duct carcinoma, EHCC, lung cancer (such as non-small cell lung cancer; NSCLC), and gastric cancer. Accordingly using the methods of the instant disclosure, the subject's risk for progressing to another stage of cancer can be determined. In yet another example, a subject with cancer can also be evaluated to determine if a therapeutic regimen is appropriate for the subject using methods disclosed herein. A subject of interest can also be selected to determine if preventative treatment such as, watchful-waiting protocols, should be undertaken.

In a general embodiment, this disclosure provides a method of determining survival probability for a subject with cancer. In particular embodiments, the method is directed to calculating the survival probability for a subject with a solid tumor, using whole tissue sections, tissue microarrays, and arrays of minute tissue sections. In another embodiment, the method is directed to determining survival probability for a subject using solidified cell samples, such as leukemia cells frozen for example, in an embedding compound.

Also described herein is the identification of predictive biomarkers for lung cancer, such as non-small cell lung cancer. Using a cohort of lung cancer patients for whom survival data is available, "old fashion" immunohistochemistry and automated image analyses were applied to generate a continuous variable to reflect the staining for the analyte of interest. As illustrated in FIG. 8, four selected individual analytes (p-mTOR, p-Akt, p-MAPK, and EGFR) do not demonstrate a statistically significant survival advantages based on a binary analysis of "positive" or "negative". In FIG. 8B, the ratio-metric approach was applied, wherein the denominator analyte is downstream of the numerator analyte in the pathway. Both ratios P-mTOR/P-Akt and p-MAPK/EGFR demonstrate survival differences by Kaplan Meier analysis. Surprisingly, combining the ratios two by simple addition (FIG. 8D) resulted in an even more statistically significant biomarker indicator. Multivariate analysis has been performed, and this double-ratio metric ([P-mTOR/P-Akt]+[p-MAPK/EGFR]) remains significant. Preliminary data on a second cohort of specimens suggest this metric is independent of EGFR mutational status.

Taking this approach further, we have been examining gastric (stomach) cancers in a very large cohort of 946 patients for which detailed clinico-pathologic data is available. Numerous markers were interrogated, including mucin genes, p53, e-cadherin, beta-catenin and others—including Her2 and Her3, which were examined further. "Manual" interpretation by a pathologist resulted in non-continuous, qualitative data (with a value range rather than binary). In a multivariate analysis with hazards ratios (HRs), HER2 expression was a negative prognostic factor (HR 1.37), and HER3 was a positive prognostic factor (HR 0.94). Different ratio-based metrics have been applied, demonstrating an HR of 0.61. (Each of these HRs is statistically significant; the greater deviation from 1.0, the greater the significance).

Representative biomarkers described herein are predictive/diagnostic/prognostic because one (or more) of the component antigens increases or decreases. However, provided biomarkers illustrate that the relative amounts of the component antigens are what is most relevant (and significant), in that one or another of the component antigens can be altered (up or down) without the other antigen(s) altering, and the data still reflects that the biomarker is predictive. As clearly illustrated herein with the HER2/HER3 system, the balance of the components in the calculated biomarker is key. In this example, either an increase in HER2 or a decrease in HER3 alters the biological status /disease state/prognosis of the subject with the same outcome. Thus, the stoichiometry of the component antigens strongly influences the calculated biomarker—and the biological outcome. This system can be viewed as a flow moving through or in a pathway—it is important both that the elements of the pathway are present and also that there is sufficient signaling capacity within the entire pathway for the signal (the biological effect) to be felt. One signal in excess in the pathway may not matter, where the pathway is at or beyond capacity.

It will be understood that the methods and other embodiments provided herein, though exemplified in the context of various cancers, are applicable to other diseases and conditions. The illustrated cancer approach can be applied to any tissue-based disease where a cell/tissue-based analysis is feasible. Although the analysis does not require a cell-by-cell analysis, in many embodiments it is applied to a cell-type, within a tissue. Examples of measurements of non-malignant (that is, not linked to cancer) processes include cirrhosis of the liver, renal disease (glomerular or tubular) and other processes that will be recognizable by one of ordinary skill.

IV. Cancer Associated Proteins

It is contemplated within the present disclosure that a cancer associated protein is a protein known to be associated with cancer or a protein that can be determined (via methods known or routinely developed in the art) to be associated with a specific type or form of cancer. For example, high levels of expression (upregulation) of CA 125 in ovarian tissue samples are commonly associated with an increased risk for the development of ovarian cancer. It will be apparent to one of ordinary skill in the art that "cancer-specific markers" or "tissue-specific markers" are often linked with a specific form of cancer, or location of cancer, and are therefore considered cancer associated proteins as defined herein. Additionally, the term "tumor antigen" as known in the art refers to a substance (e.g., a protein) produced by a tumor cell that is not typically produced (and therefore associated) with a normal, non-cancerous cell. More distantly "associated" proteins are also considered, including for instance cytokeratins, other structural proteins, proteins that interact therewith, and so forth. The success of ratio based markers, as illustrated herein, is detection of aberrant expression of normally expressed proteins.

In another example of the instant disclosure, proteins that were not previously characterized with a cancer may be detected through various techniques known or developed in the art, to be associated with a specific type or form of cancer, these types of cancer associated proteins are often termed "tumor associated antigens" and include mutated or aberrant proteins that are produced as a result of the presence of the cancer. In another embodiment of the instant disclosure, a previously characterized cellular protein may be found to be directly (or indirectly) impacted by a cell signaling pathway that in turn, activates or positively influences the development or progression of cancer, such as proteins found in cellular survival, apoptosis and growth factor pathways (e.g., 4E-BP1) and is therefore a cancer associated protein as defined herein. Specific examples of cancer associated proteins are discussed in more detail below.

In one embodiment of the instant disclosure, two or more cancer associated proteins are identified and the relative contents (protein expression levels) are compared to provide a biomarker indicator of disease. For example, overexpression of HER2 in normal breast tissue may be considered a risk factor for the development of breast cancer. In addition, upregulation of a second protein in the same breast tissue sample, such as survivin (BIRC5), a protein associated with inhibition of apoptosis, may provide significant accumulative evidence in conjunction with the first cancer associated protein to indicate that there is an elevated risk for uncontrolled cellular proliferation and the development of a malignant neoplasm in the sample. The identification and quantitation of two or more cancer associated proteins in a sample using the methods disclosed herein can be used to determine the presence of cancer in a subject and, additionally, the relative survival rate of a subject with cancer.

It is contemplated by the methods disclosed herein that the two or more cancer associated proteins may or may not be directly linked to one another, for example, by protein structure or function. For example, the first cancer associated protein may be a protein from a growth factor pathway, and the second cancer associated protein may be directed to the expression of a gene product related to nutrient metabolism. In another embodiment, the two or more cancer associated proteins may be directly linked to one another. For example, the first cancer associated protein may be related to overexpression of a cell signaling protein, such as mTOR, while the second cancer associated protein may be a protein from the same cell signaling pathway, such as AKT. In a further embodiment, the two or more cancer associated proteins may be indirectly linked to one another. For example, the first cancer associated protein may be a cell signaling protein, such as AKT, while the second cancer associated protein is a cellular proliferation marker, such as Ki-67.

In one embodiment of the instant disclosure, the first cancer associated protein may be remotely upstream or remotely downstream from the second cancer associated protein. In another embodiment, the first cancer associated protein may be directly upstream or directly downstream from the second cancer associated protein.

In another example, the two or more cancer associated proteins may be related in terms of protein function. For example, the first cancer associated protein may be directed to the expression of a phosphorylated (activated) protein, while the second cancer associated protein is also directed to expression of a phosphorylated protein, such as pERK1/2.

In a particular embodiment, the two or more cancer associated proteins are proteins that are known, or can be determined by methods known to one of ordinary skill in the art, to be inter-connected. For example, in a specific embodiment, the two or more cancer associated proteins are found within the same cell signaling or growth factor pathway. In another embodiment, the two or more cancer associated proteins are known or can be determined by one of ordinary skill in the art to "cross-talk". For the purposes of this disclosure, the term "cross-talk" refers to the phenomenon that signal components in signal transduction can be shared between different signal pathways and responses to a signal inducing condition (e.g., stress) can activate multiple responses in a cell, tissue or organism. In a specific embodiment, the term "cross-talk" refers to the mechanism by which activated signal molecules in a primary signal transduction pathway can regulate or influence signaling molecules in another primary signal transduction pathway.

It will be appreciated by one of ordinary skill in the art that multiple cellular pathways exist which can overlap in the development of a cancer. For example, it is known that simultaneous inhibition of two signaling pathways can result in a substantially enhanced antitumor effect (Carracedo et al., *J. Clin. Invest.*, 2008; 118 3065-3074). Specifically, Carracedo et al. demonstrated that inhibition of the MAPK signaling pathway enhanced the anti-tumoral effect of inhibition of the mTOR signaling pathway in mouse models of both prostate and breast cancer.

In a general embodiment of the disclosure, the cancer associated protein comprises a tumor antigen or tumor associated antigen. In a broad embodiment, the cancer associated protein is present in a solid tumor. In a further embodiment, the cancer associated protein is present in a carcinoma selected from the group consisting of breast, lung, prostate, colon, liver, thyroid, kidney, and bile duct carcinoma. In one embodiment, the cancer associated protein is observed in a group of cancers consisting of, but not limited to adrenal tumor, bile duct cancer, bladder cancer, bone cancer, brain tumor, breast cancer, cardiac sarcoma, cervical cancer, colorectal cancer, endometrial cancer, esophageal cancer, germ cell cancer, gynecologic cancer, head and neck cancer, hepatoblastoma, renal cancer, laryngeal cancer, leukemia, liver cancer, lung cancer; lymphoma, melanoma, multiple myeloma, neuroblastoma, oral cancer, ovarian cancer, pancreatic cancer, parathyroid cancer, pituitary tumor, prostate cancer, retinoblastoma, rhabdomyosarcoma, skin cancer (non-melanoma), small bowel cancer, stomach (gastric) cancer, testicular cancer, thyroid cancer, uterine cancer, vaginal cancer, vulvar cancer, and Wilms' tumor. In another embodiment, the cancer associated protein is present in a blood-borne cancer, such as leukemia, multiple myeloma or lymphoma.

In one embodiment, the cancer associated protein is used to determine cancer survival probability for a subject with a cancer by identifying at least two cancer associated proteins in a sample, quantifying the at least two cancer associate proteins in the sample, normalizing the content of the two cancer associated proteins and comparing the normalized levels of the first and second cancer associated proteins to obtain a biomarker indicator and correlating the biomarker indicator with survival probability of the subject with the cancer.

In another embodiment, the cancer associated protein is used to detect the presence of a cancer in a subject by determining the levels of at least two cancer associated proteins in a sample, normalizing the content of the two cancer associated proteins and comparing the normalized levels of the first and second cancer associated proteins with the level of the first and second cancer associated proteins in a normal non-cancerous subject, in order to identify the presence of the cancer in the subject. In one embodiment, the cancer associated proteins can be used to detect the presence of a solid tumor, such as a carcinoma in a subject. In a further embodiment, the two cancer associated proteins can be used to detect the presence of a carcinoma in a subject, such as a carcinoma selected from the group consisting of, but not limited to, breast, lung, prostate, colon, stomach (gastric), ovarian, cervical, brain, skin, esophageal, biliary tract, and extrahepatic cholangiocarcinoma (EHCC). In a further embodiment, the two or more cancer associated proteins are directly associated with the detection of EHCC.

In another embodiment, the two or more cancer associated proteins are correlated with the presence of a blood-borne cancer. In a further embodiment, the two or more cancer associated proteins are specific for the detection of leukemia, multiple myeloma or lymphoma. In a particular embodiment, the two or more cancer associated proteins are specific for the identification or detection of leukemia in a subject.

In one embodiment, the two or more cancer associated proteins are tumor antigens selected from the group consisting of, but not limited to, AKT; p-AKT; Blood Group Tn Antigen, CA150; CA19-9; CA50; CAB39L; CD22; CD24; CD63; CD66a+CD66c+CD66d+CD66e; CTAG1B; CTAG2; Carcino Embryonic Antigen (CEA); EBAG9; EGFR; FLJ14868; FMNL1; GAGE1; GPA33; Ganglioside OAcGD3; Heparanase 1; HER2; HER3; JAKMIP2; LRIG3; Lung carcinoma Cluster 2; M2A Oncofetal Antigen, MAGE 1; MAGEA10; MAGEA11; MAGEA12; MAGEA2; MAGEA4; MAGEB1; MAGEB2; MAGEB3; MAGEB4; MAGEB 6; MAGEC1; MAGEE1; MAGEH1; MAGEL2; MGEA5; MOK protein kinase; MAPK; p-MAPK; mTOR; p-mTOR; MUC16; MUC4; Melanoma Associated Antigen; Mesothelin; Mucin 5AC; Neuroblastoma; OCIAD1; OIP5; Ovarian Carcinoma-associated Antigen; PAGE4; PCNA; PRAME; Plastin L; Prostate Mucin Antigen (PMA); Prostate Specific Antigen (PSA); PTEN; RASD2; ROPN1; SART2; SART3; SBEM; SDCCAG10; SDCCAG8; SPANX; SPANXB1; SSX5; STEAP4; STK31; TAG72; TEM1; XAGE2; Wilms' Tumor Protein, alpha 1 Fetoprotein; and tumor antigens of epithelial origin.

In another embodiment, the cancer associated proteins are tumor associated antigens selected from the group consisting of, but not limited to, 5T4; AKT; p-AKT; ACRBP; Blood Group Tn Antigen; CD164; CD20; CTHRC1; ErbB 2; FATE1; HER2; HER3; GPNMB; Galectin 8; HORMAD1; LYK5; MAGEA6; MAGEA8; MAGEA9; MAGEB18; MAGED2; MAPK; p-MAPK; mTOR; p-mTOR; MUC1; MUC2; MelanA; Melanoma gp100; NYS48; PARP9; PATE; Prostein; PTEN; SDCCAG8; SEPT1; SLC45A2; TBC1D2; TRP1; XAGE1; and tumor associated antigens of epithelial origin.

In another embodiment, the two or more cancer associated proteins comprise two or more proteins from the PI3K, AKT or ERK1/2 signaling pathway. In a particular embodiment the two or more cancer associated proteins are selected from the group consisting of, but not limited to, 4E-BP1, phosphorylated 4e-BP1 (p-4E-BP1), eIF-4E, phosphorylated eIF-4E (p-eIF-4E), AKT, phosphorylated AKT (pAKT), Erk1/2, Hsp27, Hsp 90, Tcl1, Grb10, Ft1, Jip1, Posh, mTOR, phosphorylated mTOR(p-mTOR), periostin, and PTEN.

In another embodiment, the cancer associated protein as defined herein refers to a tumor antigen or a tumor associated antigen. In a one embodiment, the tumor antigen or tumor associated antigen is specific for the identification or detection of a carcinoma selected from the group consisting of, but not limited to, breast, lung, prostate, colon, ovarian, cervical, brain, skin, esophageal, biliary tract and extrahepatic cholangiocarcinomas. In a particular embodiment, the cancer associated protein is specific for the detection or identification of EHCC. In a specific embodiment, the cancer associated protein is p-AKT, p-mTOR p-MAPK, EGFR, Her2, Her3 or PTEN.

In one embodiment, the cancer associated protein comprises a cell signaling or growth factor pathway protein. In a particular embodiment, the cancer associated protein is selected from the group of signaling pathways consisting of, but not limited to, PI3K, AKT, PTEN, ERK1/2, Wnt, and TGF-β, as well documented in the art, see for example, Strimpakos et al., *Cancer Treat Rev*; Nov. 13, 2008; or Katoh and Katoh, *Int J Mol Med.* 2008; 14:4042-5.

In another embodiment, the cancer associated protein comprises a protein of the p53 pathway. In a further embodiment, the cancer associated protein of the p53 pathway includes but is not limited to, 53BP1, ALDH11, BRCC45, BNIP3L, CDKN2A, DRAM, DBC1, DDB2, ING1, JAB, MDM2, OVCA1, PARC, PBK, PIG3, PRMT4, and protein products of p21, p53, p63 and p73.

In a particular embodiment, the cancer associated protein comprises a growth factor or growth factor receptor protein. In a further embodiment, the cancer associated protein is selected from the group consisting of, but not limited to, ALK, EGFR, Erb 3, GCSF receptors, Kit (c), PDGF receptors, Pan Trk, Raf 1, Ret, TIE, Trk A, Trk B, Trk C, VEGF receptor 1, VEGF receptor 2, VEGF receptor 3, and Xmrk.

In yet another embodiment, the cancer associated protein comprises an EGF protein, selected from the group consisting of, but not limited to, ACK1, EGF, EPS8; Erb 2, Erb 3, Erb 4, TMEFF2, and Xmrk.

In another embodiment, the two or more cancer associated proteins comprise a FGF, PDGF, TGF, THF or VEGF protein, as well known in the art (Cao et al., *J. Mol. Med;* 2008; (7)785-9; Katoh and Katoh, *Clinical Cancer Research*

2007; 14: 4042-5; Jiang and Hui, *Developmental Cell* 2008; 6:801-12; and Antonescu, *Modern Pathology* 2008; 21:suppl. 2:S31-36).

In one embodiment, the cancer associated protein is a signal transducer protein. In a further embodiment, the signal transducer protein is selected from the group consisting of, but not limited to, A RAF, ASPP1, ax1, B Raf, CBLB, CD45R, ELMO, ERAS, FES, JAK1, JAK2, JAK3, JNK1, JNK2, KAT13A, NDRG1, PI3K, PIM, Ras (p21), SRC1, Styk1, and c Abl.

As discussed already, a number of cell signaling proteins associated with cancer require phosphorylation to be fully activated, such as AKT, mTOR, MAPK, and ERK1/2. Therefore, to detect the functional status of a cancer associated protein (i.e., if it is active or inactive) phospho-specific antibodies can be used to detect phosphorylated proteins in a sample (i.e., the detection of pAKT, p-mTOR, p-MAPK, or pERK1/2). Signal intensity from detection of the phosphorylated proteins can be quantified to obtain intensity values for each detected phosphorylated protein. In one embodiment, the cancer associated protein comprises a phosphorylated cancer associated protein. In a particular embodiment, the phosphorylated cancer associated protein is selected from the group consisting of, but not limited to, pAKT, p-mTOR, p-4E-BP1, p-eIF-4E (eukaryotic initiation factor 4E), pERK1/2, pHER2 (human epidermal growth factor receptor), p70S6K1 (phosphorylated ribosomal protein S6 kinase 1), phosphorylated ribosomal protein S6 (S6), p-glycogen synthase kinase 3β, pMAPK, and pEGFR.

In another embodiment, the cancer associated protein comprises a protein associated with the AKT signaling pathway. In a particular embodiment the cancer associate protein associate with the AKT signaling pathway includes, but is not limited to, 4E-BP1, phosphorylated 4e-BP1 (p-4E-BP1), eIF-4E, phosphorylated eIF-4E (p-eIF-4E), AKT, phosphorylated AKT (pAKT), Erk1/2, Hsp27, Hsp 90, Tcl1, Grb10, Ft1, Jip1, Posh, mTOR, phosphorylated mTOR(p-mTOR), periostin and PTEN.

In one embodiment, the phosphorylated cancer associated protein is detected by phosphor-specific antibodies including, but not limited to, pAKT antibodies, p-mTOR antibodies, p-4E-BP1 antibodies, p-eIF-4E antibodies, pERK1/2 antibodies, p-glycogen synthase kinase 3β antibodies, pMAPK antibodies, and pEGFR antibodies.

In one embodiment, the cancer associated protein is a tumor antigen or a tumor associated antigen selected from the group of factors consisting of, but not limited to, EGF, FGF, PDGF, TGF, TNF, and VEGF.

In another embodiment, the cancer associated protein comprises a protein from a cellular apoptosis pathway. In other embodiments, the cancer associated protein is a protein of the p53 pathway. Original FIGS. 6A-6D that were presented in the provisional application from which this filing claims priority (and which are incorporated herein by reference) are schematic drawings of a EGF, AKT, p53 and cellular apoptosis pathway as contemplated by the instant disclosure and identify several cancer associated proteins that can be utilized by the methods disclosed herein.

In a particular embodiment, the cancer associated protein includes a cancer associated protein from the group of proteins consisting of, but not limited to, AKT, p-AKT, PTEN, PI3K, PIP2, PIP3 and Ras.

In another embodiment, the cancer associated protein comprises a tyrosine kinase receptor, such as AKT.

In other embodiments, the cancer associate protein is a protein selected from the signal transduction pathways selected from AKT, HER2, and EGFR.

In a further embodiment, the cancer associated protein is selected from the group consisting of stathmin, total prostate specific antigen (tPSA), human kallikrein 2 (hk2), type 1 insulin-like growth factor receptor, NF-KB, hypoxia inducible factor-1, protein kinase A type I, vascular endothelial growth factor, 5-lipoxygenase, 12-lipoxygenase, angiotensin II receptor type 1, bradykinin receptor type 1, interleukin-6, ras, MDM2, bcl-2/bclxL, vitamin D receptor, estrogen receptor-β and peroxisome proliferator-activated receptors (PPARs).

The cancer associated protein expression profiles may be used to check how a subject is responding to treatment. For example, a decrease or return to normal level of protein expression by the cancer associated protein may indicate that the cancer is responding to therapy (wherein a decrease in the cancer associated protein expression is linked to a decreased incidence of cancer), whereas an increase in protein expression of the cancer associated protein may indicate (wherein an increase in cancer associated protein expression is linked to an increased incidence of cancer) that the subject is not responding to treatment. After treatment has ended, cancer associated proteins may also be used to check for recurrence. If a cancer associated protein is used to determine whether a treatment is working or if there is recurrence, the cancer associated protein levels can be measured over a period of time to see if the levels are steady-state, increasing or decreasing. These "serial measurements" can in some instances be more meaningful than a single measurement. Accordingly, it is contemplated within this disclosure that cancer associated proteins levels may be checked or monitored at the time of diagnosis; before, during, and after therapy; and then periodically to monitor for recurrence.

It is also contemplated by the present disclosure that a number of other cancer associated proteins that are currently unknown might reasonably be incorporated into the above lists of cancer associated proteins without undue experimentation. For example, a suspected cancer associated protein can be tested through the use of various signal modulating agents, in concentrations that can feasibly be achieved and maintained clinically, on human cancer cell lines. The suppression, reversal or inhibition of tested cancer associated proteins, especially those associated with cell signaling pathways, which appear promising, can then be tested in animal models, and ultimately tested in a clinical environment.

In some embodiments, the cancer associated protein is detected in a sample using an antibody specific for the detection of the cancer associated protein and a porous membrane to separate the cancer associated protein from the remainder of the sample. In other embodiments, the cancer associated protein is detected in a sample comprising a formal fixed, paraffin embedded tissue block, fresh frozen tissue biopsy, solidified cells, serum or other biological fluid. Specific examples of the types of samples that can be tested using the methods disclosed herein will be discussed in detail below. Additionally, the types of probes or detector molecules that can be used by the methods disclosed herein to detect or identify two or more cancer associated proteins of the instant application will also be discussed in more detail below.

V. Probes

In a general embodiment of the instant disclosure, the probe to be used in the methods disclosed herein is specific for the detection of a cancer associated protein. In a particular embodiment, the probe is an antibody with an affinity for the cancer associated protein. In a further embodiment, the antibody is specific for the detection of a cancer associated protein from a solid tumor, such as a carcinoma.

In a general embodiment, the probe is an antibody with an affinity for the detection of the cancer associated protein, wherein the cancer associated protein is selected from the group of cancers consisting of, but not limited to, adrenal tumor, bile duct cancer, bladder cancer, bone cancer, brain tumor, breast cancer, cardiac sarcoma, cervical cancer, colorectal cancer, endometrial cancer, esophageal cancer, germ cell cancer, gynecologic cancer, head and neck cancer, hepatoblastoma, renal cancer, laryngeal cancer, leukemia, liver cancer, lung cancer; lymphoma, melanoma, multiple myeloma, neuroblastoma, oral cancer, ovarian cancer, pancreatic cancer, parathyroid cancer, pituitary tumor, prostate cancer, retinoblastoma, rhabdomyosarcoma, skin cancer (non-melanoma), small bowel cancer, stomach (gastric) cancer, testicular cancer, thyroid cancer, uterine cancer, vaginal cancer, vulvar cancer, and Wilms' tumor.

In one embodiment, the probe is specific for the identification of a cancer associated protein associated with a carcinoma, selected from the group consisting of, but not limited to, breast, lung, prostate, colon, stomach (gastric), ovarian, cervical, brain, skin, esophageal, biliary tract, and EHCC. In a further embodiment, the probe is specific for the detection of a cancer associated protein associated with EHCC, lung cancer, or gastric cancer.

In another embodiment, the probe is specific for the identification of a cancer associated protein of a blood-borne cancer. In a further embodiment, the probe is specific for the detection of a cancer associated protein of leukemia, multiple myeloma or lymphoma. In a particular embodiment, the probe is specific for the detection of a leukemia cancer associated protein.

In one embodiment, the probe is specific for the detection of an individual cancer associated protein, wherein the individual cancer associated protein is a tumor antigen selected from the group consisting of, but is not limited to, AKT; p-AKT; Blood Group Tn Antigen, CA150; CA19-9; CA50; CAB39L; CD22; CD24; CD63; CD66a+CD66c+ CD66d+CD66e; CTAG1B; CTAG2; Carcino Embryonic Antigen (CEA); EBAG9; EGFR; FLJ14868; FMNL1; GAGE1; GPA33; Ganglioside OAcGD3; Heparanase 1; HER2; HER3; JAKMIP2; LRIG3; Lung carcinoma Cluster 2; M2A Oncofetal Antigen, MAGE 1; MAGEA10; MAGEA11; MAGEA12; MAGEA2; MAGEA4; MAGEB1; MAGEB2; MAGEB3; MAGEB4; MAGEB6; MAGEC1; MAGEE1; MAGEH1; MAGEL2; MGEA5; MOK protein kinase; MAPK; p-MAPK; mTOR; p-mTOR; MUC16; MUC4; Melanoma Associated Antigen; Mesothelin; Mucin 5AC; Neuroblastoma; OCIAD1; OIP5; Ovarian Carcinoma-associated Antigen; PAGE4; PCNA; PRAME; Plastin L; Prostate Mucin Antigen (PMA); Prostate Specific Antigen (PSA); PTEN; RASD2; ROPN1; SART2; SART3; SBEM; SDCCAG10; SDCCAG8; SPANX; SPANXB1; SSX5; STEAP4; STK31; TAG72; TEM1; XAGE2; Wilms' Tumor Protein, alpha 1 Fetoprotein; and tumor antigens of epithelial origin.

In another embodiment, the probe is specific for the detection of an individual cancer associated protein, wherein the individual cancer associated protein is a tumor associated antigen selected from the group consisting of, but not limited to, 5T4; AKT; p-AKT; ACRBP; Blood Group Tn Antigen; CD164; CD20; CTHRC1; ErbB 2; FATE1; HER2; HER3; GPNMB; Galectin 8; HORMAD1; LYK5; MAGEA6; MAGEA8; MAGEA9; MAGEB18; MAGED2; MAPK; p-MAPK; mTOR; p-mTOR; MUC1; MUC2; MelanA; Melanoma gp100; NYS48; PARP9; PATE; Protein; PTEN; SDCCAG8; SEPT1; SLC45A2; TBC1D2; TRP1; XAGE1; and tumor associated antigens of epithelial origin.

In another embodiment, the probe is specific for the detection of a cancer associated protein, wherein the cancer associated protein is a protein of the PI3K, AKT or ERK1/2 signaling pathway. In one embodiment, the probe is specific for the identification of a cancer associated protein from a cell signaling or growth factor pathway. In a particular embodiment, the probe is specific for the identification of a cancer associated protein from a cell signaling pathway selected from the group consisting of, but not limited to, PI3K, AKT, PTEN, ERK1/2, Wnt, and TGF-β.

The AKT signaling pathway is known to play an important role in the signaling pathways in response to growth factors and serves to regulate several cellular functions including nutrient metabolism, cell growth, apoptosis and survival. AKT is a serine/threonine kinase that belongs to a much larger (AGC) family of super protein kinases. Deregulation of AKT has been frequently associated with human disease including cancer. For all AGC family kinases, phosphorylation of the serine and threonine residue is necessary for full activation of the kinase. In a particular embodiment of the disclosure, the probe is an antibody that is specific for the detection of a cancer associated protein of the AKT signaling pathway. Therefore, identification of a cancer associated protein by the probe can be used as an indicator of activation of the cancer associate protein in the AKT signaling pathway. For example, in a particular embodiment, the probe is specific for the detection of phosphorylated AKT, which in turn is a measure of activated AKT. Because deregulations of the AKT signaling pathway are associated with disease states such as cancer, the detection of an activated AKT cancer associate protein may be an indicator of a cancerous disease state.

In a particular embodiment the probe is specific for the detection and identification of a cancer associated protein selected from the group consisting of, but not limited to, 4E-BP1, phosphorylated 4e-BP1 (p-4E-BP1), eIF-4E, phosphorylated eIF-4E (p-eIF-4E), AKT, phosphorylated AKT (pAKT), Erk1/2, Hsp27, Hsp 90, Tcl1, Grb10, Ft1, Jip1, Posh, mTOR, phosphorylated mTOR(p-mTOR), periostin, and PTEN.

In another embodiment, the probe used to detect the cancer associated protein is a tumor antigen antibody or a tumor associated antigen antibody. In a one embodiment, the probe is a tumor antigen or a tumor associated antigen antibody associated with a carcinoma, including, but not limited to, breast, lung, prostate, colon, stomach (gastric), ovarian, cervical, brain, skin, esophageal, biliary tract and extrahepatic cholangiocarcinomas. In a particular embodiment, the probe is a tumor antigen or tumor associated antigen antibody associated with EHCC. In a specific embodiment, the probe is an antibody specific for the detection of AKT, p-AKT, MAPK, p-MAPK, EGFR, Her2, Her3, mTOR, p-mTOR, or PTEN.

In one embodiment, the probe used to detect the cancer associate protein is a tumor antigen antibody including, but not limited to, AKT antibodies, p-AKT antibodies, CA150 antibodies, CA19-9 antibodies, CA50 antibodies, CAB39L antibodies, CD22 antibodies, CD24 antibodies, CD63 antibodies, CD66 antibodies; CTAG1B antibodies, CTAG2 antibodies, Carcino Embryonic Antigen (CEA) antibodies, EBAG9 antibodies, FLJ14868 antibodies, FMNL1 antibodies, GAGE1 antibodies, GPA33 antibodies, Ganglioside OAcGD3 antibodies, Heparanase 1 antibodies, HER2 antibodies, HER 3 antibodies, JAKMIP2 antibodies, LRIG3 antibodies, Lung carcinoma cluster 2 antibodies, MAGE 1 antibodies, MAGEA10 antibodies, MAGEA11 antibodies, MAGEA12 antibodies, MAGEA2 antibodies, MAGEA4 antibodies, MAGEB1 antibodies, MAGEB2 antibodies, MAGEB3 antibodies, MAGEB4 antibodies, MAGEB6 antibodies, MAGEC1 antibodies, MAGEE1 antibodies, MAGEH1 antibodies, MAGEL2 antibodies, MAPK antibodies, MGEA5 antibodies, MOK protein kinase antibodies, mTOR antibodies, p-mTOR antibodies, MUC16 antibodies, MUC4 antibodies, Melanoma Associated Antigen antibodies, Mesothelin antibodies, Mucin 5AC antibodies, Neuroblastoma antibodies, OCIAD1 antibodies, OIP5 antibodies, Ovarian Carcinoma-associated Antigen antibodies, PAGE4 antibodies, PCNA antibodies, PRAME antibodies, Plastin L antibodies, Prostate Mucin Antigen (PMA) antibodies, Prostate Specific Antigen (PSA) antibodies, RASD2 antibodies, ROPN1 antibodies, SART2 antibodies, SART3 antibodies, SBEM antibodies, SDCCAG10 antibodies, SDCCAG8 antibodies, SPANX antibodies, SPANXB1 antibodies, SSX5 antibodies, STEAP4 antibodies, STK31 antibodies, TAG72 antibodies, TEM1 antibodies, XAGE2 antibodies, alpha 1 Fetoprotein antibodies, antibodies to tumor antigens of epithelial origin, or antibodies to another disease/condition/cancer.

In another embodiment, the cancer associated proteins are tumor associated antigens selected from the group consisting of, but not limited to, 5T4 antibodies, ACRBP antibodies, CD164 antibodies, CD20 antibodies, CTHRC1 antibodies, ErbB 2 antibodies, FATE1 antibodies, GPNMB antibodies, Galectin 8 antibodies, HORMAD1 antibodies, LYK5 antibodies, MAGEA6 antibodies, MAGEA8 antibodies, MAGEA9 antibodies, MAGEB18 antibodies, MAGED2 antibodies, MUC1 antibodies, MUC2 antibodies, MelanA antibodies, Melanoma gp100 antibodies, NYS48 antibodies, PARP9 antibodies, PATE antibodies, Prostein antibodies, SDCCAG8 antibodies, SEPT1 antibodies, SLC45A2 antibodies, TBC1D2 antibodies, TRP1 antibodies, XAGE1 antibodies, antibodies to tumor associated antigens of epithelial origin, and antibodies to any of the other (cancer) antigens referenced herein or recognized in the art.

In a further embodiment, the probe in the methods discloses herein is an antibody with an affinity for the cancer associated protein. In another embodiment, the probe used to detect the cancer associated protein comprises an antibody of a cell signaling pathway. In a further embodiment, the probe comprises an antibody of the AKT cell signaling pathway, including, but not limited to, AKT antibodies, phospho-AKT antibodies (e.g., antibodies specific for Phospho T308-AKT or Phospho-S473-AKT), mTOR antibodies and phospho-mTOR antibodies.

In another embodiment, the probe used is specific for the detection of a cancer associated protein of the PTEN cell signaling pathway, including, but not limited to, PTEN antibodies and TPTE antibodies.

In yet another embodiment, the probe used is an antibody specific for the detection of a cancer associated protein of the Wnt cell signaling pathway, including, but not limited to, APC antibodies, LEF1 antibodies, PTCH antibodies, Sonic Hedgehog antibodies, WISP2 antibodies; WNT2 antibodies; WNT2B antibodies; WNT4 antibodies; Wnt1 antibodies; Wnt10a antibodies; Wnt5a antibodies; Wnt6 antibodies; and Wnt8a antibodies.

In a further embodiment, the probe used is specific for the detection of a cancer associated protein of the p53 pathway. In a further embodiment, the probe is an antibody of the p53 pathway, including, but not limited to, 53BP1 antibodies, ALDH11 antibodies, BRCC45 antibodies, BNIP3L antibodies, CDKN2A antibodies, DRAM antibodies, DBC1 antibodies, DDB2 antibodies, ING1 antibodies, JAB antibodies, MDM2 antibodies, OVCA1 antibodies, PARC antibodies, PBK antibodies, PIG3 antibodies, PRMT4 antibodies, p21 antibodies, p53 antibodies, p63 antibodies, and p73 antibodies.

In a particular embodiment, the antibody used in the methods disclosed herein to detect the cancer associated protein comprises a growth factor or growth factor receptor antibody from a growth factor pathway. In a further embodiment, the antibody is a growth factor receptor antibody including, but not limited to, ALK antibodies, EGFR antibodies, Erb 3 antibodies, GCSF receptor antibodies, Kit (c) antibodies, PDGF receptor antibodies, Pan Trk antibodies, Raf 1 antibodies, Ret antibodies, TIE antibodies, Trk A antibodies, Trk B antibodies, Trk C antibodies, VEGF receptor 1 antibodies, VEGF receptor 2 antibodies, VEGF receptor 3 antibodies, and Xmrk antibodies.

In yet another embodiment, the antibody used to detect the cancer associated protein is an EGF antibody. In a further embodiment, the antibody used to detect the cancer associated protein is a EGF antibody selected from the group, but not limited to, ACK1 antibodies, EGF antibodies, EPS8 antibodies; Erb 2 antibodies, Erb 3 antibodies, Erb 4 antibodies, TMEFF2 antibodies, and Xmrk antibodies.

In a general embodiment, each probe used in the methods disclosed herein to detect a cancer associated protein is specific for the detection of a single cancer associated protein. In one embodiment, each probe is an antibody with a specific affinity for a single cancer associated protein. In another embodiment, the probe used in the methods disclosed herein to detect the cancer associated protein is a signal transducer antibody. In a further embodiment, the signal transducer antibody is selected from the group consisting of, but not limited to, A RAF antibodies, ASPP1 antibodies, ax1 antibodies, B Raf antibodies, CBLB antibodies; CD45R antibodies, ELMO antibodies, ERAS antibodies, FES antibodies, JAK1 antibodies, JAK2 antibodies, JAK3 antibodies, JNK1 antibodies, JNK2 antibodies, KAT13A antibodies, NDRG1 antibodies, PI3K antibodies, PIM antibodies, Ras (p21) antibodies, SRC1 antibodies, Styk1 antibodies, and c Abl antibodies.

As discussed already, a number of cell signaling proteins associated with cancer require phosphorylation to be fully activated, such as AKT, mTOR, MAPK, and ERK1/2. To detect the functional status of a cancer associated protein (i.e., if it is active or inactive), phospho-specific antibodies can be used to detect phosphorylated cancer associated proteins in a sample (i.e., the detection of pAKT, p-mTOR, p-MAPK or pERK1/2). The phospho-specific antibodies are incubated with the sample for a sufficient amount of time to bind with the phosphorylated cancer associated proteins. The sample is washed and then incubated with a secondary antibody comprising a detectable label, as routinely used in the art, resulting in the detection of phosphorylated cancer associated proteins in the sample. Signal intensity from detection of the phosphorylated cancer associated proteins can be quantified to obtain intensity values for each detected phosphorylated cancer associated protein.

In one embodiment the instant disclosure contemplates, a probe specific for the detection of a cancer associated protein, wherein the probe is specific for an activated cancer associated protein. In a further embodiment, the activated cancer associated protein comprises a phosphorylated cancer associated protein. In a particular embodiment, the phosphorylated cancer associated protein detected by the probe includes, but is not limited to, pAKT, p-mTOR, p-4E-BP1, p-eIF-4E (eukaryotic initiation factor 4E), pERK1/2, pHER2 (human epidermal growth factor receptor), p70S6K1 (phosphorylated ribosomal protein S6 kinase 1), phosphorylated ribosomal protein S6 (S6), p-glycogen synthase kinase 3β, pMAPK, and pEGFR.

In one embodiment, a phospho-specific antibody is used to detect the cancer associated protein in the sample. In a particular embodiment, the phosphorylated cancer associated protein is detected by phospho-specific antibodies including, but not limited to, pAKT antibodies, p-mTOR antibodies, p-4E-BP1 antibodies, p-eIF-4E antibodies, pERK1/2 antibodies, p-glycogen synthase kinase 3β antibodies, pMAPK antibodies, and pEGFR antibodies.

In a general embodiment, the probe used to detect the cancer associated protein binds to the cancer associated protein in a manner that allows secondary antibodies comprising a tag or detectable label, such as biotin, to bind to the primary antibody, and thereby elicit a detectable label or tag as commonly known in the art.

VI. Normalization

In one embodiment, a cancer associated protein is detected in a sample using a probe that has specificity for the (cancer) associated protein. In a further embodiment, the probe used to detect the cancer associated protein can be an antibody. In a particular embodiment that detects functional activity of the cancer associated protein, the antibody can be a phospho-specific antibody that has specificity for a phosphorylated (activated) cancer associated protein. Also contemplated are other protein modifications that can be detected using, for instance, antibodies; such modifications include methylation, acetylation and ubiquitination. For instance, the utility of acetylation (with reference to drug response) is recognized (e.g., Chen et al., *Anal Chem.* 80(16):6390-6306, 2008).

In one example, for methods that entail membrane transfer of cancer associated proteins, such as TMA methods, total cellular protein content is measured for each membrane in the TMA, for example, by incubation with biotin. After biotinylation, the membranes are incubated with antibodies against the cancer associated protein to be detected. All primary antibodies are incubated overnight and incubated with secondary antibodies, such as streptavidin-linked Cy5 and FITC conjugated anti-rabbit IgG or anti-mouse IgG. The membranes (or blots) are dried, mounted and scanned. Regions of interest are selected, and the signal intensity quantified. The expression level of each cancer associated protein present on the membrane is normalized against the intensity of total cellular protein content of the same membrane, herein referred to as inter-array normalization. The inter-array normalization step accounts for, and eliminates, background variations between membranes within a set. Thus, allowing the accurate determination of content for each cancer associated protein on each membrane within a set.

In a further optional embodiment, a second normalization step occurs. In the second normalization step, each cancer associated protein detected in each individual sample is normalized to account for variations between individually tested samples. For example, each detected cancer associated protein is normalized against the expression level of known variable in the sample, such as normal epithelium or stroma. In one example, the normal epithelia or stroma intensity data is compiled and awarded a value of 1.00. The cancer associated proteins detected in the same sample are normalized against the value awarded to the normal epithelia resulting in a relative increase or decrease in expression of the cancer associated protein detected in the same sample.

The second normalization process accounts for, and eliminates, variations that occur between testing's of samples, such as differences that arise out of human error for example loading differences or differences that occur when two users are asked to perform the same assay.

In another example, each detected cancer associated protein is normalized against the expression level of known "housekeeping" protein in the sample, such as actin. In one example, the intensity data for actin is compiled and awarded a value of 1.00. The cancer associated proteins detected in the same sample are normalized against the value awarded to actin resulting in a relative increase or decrease in expression of the cancer associated protein detected in the same sample to accommodate for variations in testing between samples or batches.

As discussed above, the signal (or intensity) generated by the cancer associated protein can be normalized for background variation within a sample. For example, in one embodiment, a cancer associated protein signal is normalized against a known "housekeeping" protein in the same sample. In embodiment's were multiple membranes are stacked around a tissue section thereby allowing transfer of cancer associated proteins through multiple membranes, this normalized procedure accounts for any non-linear transfer of proteins from one membrane to the next, and so on.

In another optional embodiment, intra-array normalization can occur. For example, multiple samples representing discreet tissue samples or sources of sample may undergo independent testing to detect a cancer associated protein, e.g. a sample from a normal tissue section, an advanced stage disease tissue section, and an unknown disease state sample are concurrently evaluated. In this example, the three independent samples can be normalized to account for discrepancies obtained within each sample. In one embodiment, the median expression of a "housekeeping" protein known to be present in each sample is used to normalize each sample to the next sample, and so on.

In another embodiment, the median expression of a protein known to be expressed in each sample can be used to normalize each sample to the next sample (e.g. tubulin).

In another embodiment, one sample can be transferred to multiple membranes and the stack of membranes is probed with multiple antibodies, in this case, each antibody preferably possesses an affinity for one cancer associated protein. For example, one antibody can be specific for the detection of PTEN, another antibody can be specific for the detection of phospho-AKT, or for a specific phosphorylated residue of AKT (e.g., Phospho T308-AKT or Phospho-S473-AKT), and a further antibody can possess affinity for the detection of phospho-mTOR. The three cancer associated proteins (or others, such as those described herein) migrate through the stack of membranes based on a variety of properties, including charge or mass, and can migrate to (for instance, be captured by) different membranes in the stack. In this example, all three cancer associated proteins migrate to a different membrane in the stack, wherein each cancer associated protein is detected by an antibody specific for each cancer associated protein. The detection levels observed or detected in each membrane can be normalized to obtain a normalized intensity value for each cancer associated protein detected in each membrane and within the sample. The methodology disclosed herein can therefore accurately quantitate the content, level, or intensity of protein expression for one or more cancer associated proteins in a sample. Using this information, the expression level is normalized against a standard, such as total cellular protein content in the membrane, to account for variations in the background between membranes within one sample, and finally and additional normalization step can be used to account for variations between individual test samples. By accounting for, and accommodating for, the discrepancies involved within the testing methodologies it is possible to accurately identify, and therefore define, a specific biomarker indicator. In general, a biomarker indicator as defined herein is a ratio-based determination of one or more cancer associated proteins in conjunction with an internal standard (such as, a housekeeping protein) or a normalization step (such as direct comparison of the cancer associated protein level against total cellular protein content) that is indicative of cancer.

The biomarker indicator comprises a ratio between at least one or more different cancer associated proteins. In some instances, the biomarker indicator can be used to detect the presence of cancer in a subject. In another example, the biomarker indicator is a predictor of relative rates of survival for a subject with cancer. In a further embodiment, the biomarker indicator can be used to monitor progression of disease. In this instance, an subject diagnosed with early stage cancer can be routinely monitor for the detection of specific cancer associated proteins, for examples levels of pAKT or p-mTOR (or one or more of p-mTOR, p-Akt, p-MAPK, EGFR, Her2 and Her3) can be measured in a subject to define an early stage biomarker indicator. At a later date, the same individual can be tested for the same cancer associated proteins to determine if there has been a change in biomarker indicator (the ratio of the one cancer associated protein as compared to total cellular content in the sample). For example, a significant decrease in biomarker indicator levels after measuring the same pAKT and p-mTOR cancer associated proteins may be interpreted as a development of the cancer (wherein a significant decrease in pAKT or p-mTOR levels are linked to increased risk of cancer), and consequently linked with a decreased rate of survival. In the above example, no change in the biomarker indicator may mean that a patient is not responding well to therapy and that a new treatment regime should be initiated. Similarly, in view of the above example, a significant increase in the biomarker indicator may mean that treatment of the subject appears to be successful and should be continued. Additional specific biomarkers (using additional cancer associated proteins) are described herein.

Accordingly, the biomarker indicator is broadly applicable in various uses because the biomarker indicator provides the user with a starting point from which additional testing can be performed, and the results of the additional testing can be correlated with the first round of result so that a prognosis or adjustment of therapeutic regime can be made. The biomarker indicator because of the inherent normalization steps involved means that the biomarker indicator is not vulnerable to discrepancies that exist between individual membranes, the particular membrane probed, or the type of probe used to obtain the biomarker indicator ratio. It will be apparent to one of ordinary skill in the art that the biomarker indicator can be made more or less stringent by using cancer associated proteins that are more strongly or less strongly correlated to one another. For example, a biomarker indicator formulated using cancer associated proteins from the AKT cell signaling pathway and the selection of two proteins associated with a cancer linked to the AKT cell signaling pathway will be considered a strong biomarker indicator. In another embodiment, the selection of two cancer associated proteins that are not currently known to be directly associated may also be found to be a strong biomarker indicator dependent upon the level of expression observed and the resulting biomarker indicator.

In yet another embodiment, a multitude of equivalent areas, such as circular or rectangular areas (for example, two, three, four, five, or more), from each region of a membrane can be defined and the mean value of fluorescence for each region determined and compared to the total area and thus, protein expression for each membrane. Specific antibody signals can be calculated, as already discussed, and the sample normalized based on expression levels of total cellular protein content in the membrane. Additionally, relative expression intensities of each area within a sample can be normalized to normal epithelium or stroma. Thus, allowing for a relative comparison to be drawn between the cancer associated proteins detected in the sample and background expression.

In another embodiment, analysis of tissue sections from patients with divergent clinical courses can be used to identify novel prognostic cancer associated proteins that better diagnose cancer, the stage of cancer in the subject, and furthermore can be used to correlate the expressed cancer associated protein levels against relative survival rates to predict patient survival, for example, post-surgery.

In one embodiment, survival probability determination is performed by conducting statistical analysis of the one or more cancer associated proteins in conjunction with total cellular protein content of the sample to obtain a biomarker indicator. In another embodiment, survival probability determination is performed by conducting univariate statistical analysis of one or more cancer associated proteins in conjunction with total cellular protein content of the sample to obtain a biomarker indicator. In a further embodiment, survival probability determination is performed by conducting multivariate statistical analysis of one or more cancer associated proteins in conjunction with total cellular protein content of the sample to obtain a biomarker indicator. In some examples, the biomarker indicator is a measure of relative survival rate based on normalized expression of one or more cancer associated proteins in the sample.

In yet another embodiment, statistical analysis of the one or more cancer associated proteins can be performed as a means to monitor progression of a cancer from a normal (disease free) sample or precancerous condition to an advanced stage of disease, wherein the normal or precancerous sample are correlated with a relatively high survival rate and a statistically significant worse patients' survival rate is associated with an advanced stage of disease sample.

In one embodiment, the biomarker indicator can be used to determine prognosis of a subject with a cancer and thereby stratify patient treatment regimes based on responsiveness of the subject with cancer to different forms of treatment. For example, a subject with cancer who is currently undergoing treatment for the disease, and who demonstrates a statistically significant decrease in expression of two or more cancer associated proteins may be concluded (wherein a statistically significant decrease in the two cancer associated proteins correlates with decreased risk) as being responsive to the current form of treatment. Similarly, a subject with cancer who is undergoing treatment and continues to demonstrate a statistically significant increase in the one or more cancer associated proteins (wherein a statistically significant increase in the two cancer associated proteins correlates with increased risk) may be constructed as failing to respond positively to the current cancer treatment regime.

In a representative example, calculating survival analysis information comprises categorizing samples (cases) as high or low expressers of the cancer associated proteins under investigation by statistical analysis. In a specific embodiment, differential expression of p-AKT, p-mTOR and total PTEN in normal epithelia, dysplasia, and extrahepatic cholangiocarcinoma cases can be compared by Annova and Duncan's tests after normalization of expression. In other specific embodiments, expression of p-mTOR, p-Akt, p-MAPK, and/or EGFR are determined. In a further embodiment, associations between categorical variables can be examined using Pearsons $X^2$ and Fisher's exact tests. Furthermore, a recursive partition technique coupled with log-rank statistics can be employed to identify cut off points that discriminate outcome of patients based on the expression of the cancer associated proteins. In yet another embodiment, survival curves can be calculated using the Kaplan-Meier method. Statistical significance can be examined for example, by log-rank test and Cox proportional hazards regression model. In one embodiment, a P value of <0.20 is considered statistically significant. In another embodiment, a P value of <0.10 is considered statistically significant. In a further embodiment, a P value of <0.05 is considered statistically significant.

In a general embodiment, a biomarker indicator for a subject with cancer can be obtained by determining the ratio of one or more cancer associated proteins in conjunction with a determination of total cellular protein content in the sample.

In one embodiment, a biomarker indicator for a subject with cancer can be obtained by determining the ratio of PTEN/p-AKT in a sample. In yet another embodiment, a biomarker indicator for a subject with cancer can be obtained by determining the ratio of PTEN/p-mTOR in a sample.

In another embodiment, the biomarker indicator is directed to a subject with a carcinoma, such as bile duct carcinoma. In a further embodiment, the biomarker indicator is obtained by determining the ratio of one or more cancer associated proteins against total cellular protein content for a subject diagnosed with EHCC. In yet further embodiments, the biomarker indicator is obtained by determining the ratio of cancer associated proteins against total cellular protein content for a subject diagnosed with lung cancer or gastric cancer, or another cancer.

One of the advantages of the disclosed methods is that it allows multiple antigens to be assayed from a single tissue section. This approach permits simultaneously quantifying multiple cancer associated proteins with preservation of the morphologic structure of the tissue. A further benefit of the disclosed methods is incorporation of a normalization step that allows for the accurate assessment and comparison of inter- and intra-array samples. In addition, the methods disclosed herein allows for confirmation of the protein expression profiles observed, by standard immunohistochemistry techniques.

The basic approach described herein functions in immunohistochemistry utilizing the ratio of (usually two) individual biomarkers quantitated by image analysis of DAB stained sections. This system has been expanded to the addition of two ratio-based measures, of the structure:

($BM1/BM2$)+($BM3/BM4$)=prognostic biomarker

In provided embodiments, any ratio-based biomarker offers utility, and the combination of the two offers greater utility for the question addressed. In function, BM2 and BM4 can be thought of as normalizing biomarkers. Optionally, the denominator is downstream from the numerator in the relevant signalling pathway.

Thus, in yet another embodiment, the biomarker indicator for a subject with cancer can be obtained by determining the ratio of p-mTOR/p-Akt and p-MAPK/EGFR in a sample. Optionally, and beneficially, the simple addition of these ratios (thus, [p-mTOR/p-Akt]+[p-MAPK/EGFR]) provides an even more statistically significant biomarker indicator. It is also noted that the two ratios used to generate this additive biomarker indicator (that is, p-mTOR/p-Akt and p-MAPK/EGFR) are themselves statistically significant predictive ratios.

Also provide is the discovery that, for instance in gastric cancer, using a multivariate analysis with hazards ratios (HRs), normalized HER2 expression was a statistically significant negative prognostic factor (HR 1.37) while normalized HER3 expression was a positive prognostic factor (HR 0.94). Different ratio-based metrics have been applied, demonstrating a statistically significant HR of 0.61. In this example, HER2 and HER3 are not up/downstream of each other, but form a functional heterodimer. Thus, the balance of HER2 to HER3 is predictive, where an excess of HER2 (e.g., through overexpression of HER2 or underexpression of HER3) is a poor prognostic marker—for instance, for gastric cancer. Functionally, this is similar to the relationship of denominator analytes being downstream of numerator analytes.

VII. Assay Methods

In one embodiment, the disclosure is directed to a method of making and using a platform to perform the disclosed methods, such as a Tissue MicroArray (TMA) or Multiplex Tissue Immunoblotting (MTI) array to detect the presence of a cancer in a subject. Particular embodiments are especially useful in connection with archival tissue samples that have been fixed and embedded, for instance in paraffin (FFPE).

In a representative example, the method can involve providing a substrate (e.g., a gel, such as an embedding compound) to which a tissue section or tissue block is placed, then freezing and archiving of samples. The block can then be sectioned into a plurality of sections such that the samples are at addressable locations in the sections. Blocks or sections are deparaffinized and treated with predigestion enzymes for a brief time. Slides' comprising a tissue block or tissue section is protease inhibited and transferred to a multi-membrane stack, such as a nitrocellulose membrane. Each membrane is incubated with primary antibodies against a specific protein marker of interest, for example a cancer associated protein. Following immunodetection, total cellular proteins are measured by biotinylation of proteins present in the membrane, followed by incubation of the membranes with a secondary probe, such as streptavidin-Cy5. Following florescent-based detection of the proteins present in the sample, signal intensity is quantified, and a ratio of the specific protein marker of interest/total protein content is obtained. The obtained ratio is a biomarker indicator of survival that is used to predict or determine a subject's survival rate and thereby, can also be correlated with prognosis. Similarly, total protein detected by biotinylation can be used to generate the ratio.

In addition to TMAs, MTI and whole tissue sections, other samples from which biomolecules are to be detected (e.g. gels produced from 1- or 2-D separation of protein or nucleic acids) can be analyzed according to the disclosed methods. In one example, biomolecules on a TMA are transferred to one or more membranes and can be visualized using detector molecules ("probes"), for example antibodies, lectins, or DNA hybridization probes, having specific affinity for the biomolecule(s) of interest.

Specific embodiments provided herein include direct layered expression scanning techniques, which utilize a stack of "blank" membranes that are not specific for any particular target molecule. Instead, all (or a subset, e.g. proteins or nucleic acids) biomolecules in the sample ubiquitously bind to such membranes so as to give the user the flexibility of detecting a wide range of biomolecules in an open format.

In specific examples that utilize solid tissue sections or tissue biopsies it is preferred that the substrate is maintained at or below freezing while the samples are placed in the sample wells and frozen. In some of the provided methods, the samples are bonded to the substrate when the samples are frozen.

Also provided herein are TMAs that are either loaded with sample or "blank" blocks, containing sample wells but no samples or an incomplete sample set) made using the described methods, and individual sections cut from such tissue blocks.

Other embodiments provide methods of parallel analysis of samples, such as biological samples (e.g., a protein, a mixture of proteins, a nucleic acid, a mixture of nucleic acids, a cell, or a biological fluid). Examples of these methods involve obtaining a plurality of (biological) samples, and placing each in an addressable location in a recipient array (for instance, a blank TMA) to produce a loaded array. In specific embodiments, particularly where it is beneficial to preserve the biological structure of function of a constituent of one or more sample on the array, the recipient array is kept at or below freezing while the samples are being placed in the array. Sections can be cut (for instance, using a microtome or other device) from loaded arrays (arrays into which samples have been placed). In some of the provided methods, sections are cut from the arrays in a manner such that each section contains a plurality of portions of the samples placed in the array, which each maintain their assigned location. Sections from the provided TMA can be used to perform one or more biological analyses of samples in the arrays.

In some of the provided methods, the biological samples are placed into recipient array as liquids (for instance, suspensions), and frozen after being placed in the array. Biological samples include all clinical samples useful for detection of cancer in subjects, including, but not limited to, cells, tissues, and bodily fluids, such as: blood; derivatives and fractions of blood, such as serum; biopsied or surgically removed tissue, including tissues that are, for example, unfixed, frozen, fixed in formalin and/or embedded in paraffin; urine; sputum; cerebrospinal fluid; prostate secretions, pus; or bone marrow aspirates. In a particular example, a sample includes a tissue biopsy obtained from a human subject, such as a fixed tissue section. In another particular example, the sample includes cells from a liquid biological sample that are cancerous and that are frozen in an embedding material (such as paraffin) to become a solid sample suitable for manipulation by, for example, TMA. In additional embodiments, the method includes analyzing tissue sections archived and previously obtained from the subject of interest.

As provided herein, a recipient array substrate may include an embedding compound that is solid at 0° C. In some embodiments, recipient array contains a plurality of wells to receive the biological samples. Examples of such wells have a substantially circular cross section having a diameter of less than about 2 mm.

In specific provided examples of methods for parallel analysis of samples, more than one biological analysis (for instance, an immunological binding assay, protein binding assay, activity assay, amplification reaction, or nucleic acid hybridization) is performed on more than one section of a loaded array. The results of such analyses can be compared for the more than one biological analysis in corresponding assigned locations of different sections from the array to determine if there is a correlation between the results of the different biological analyses at different assigned locations.

In various embodiments, the results of the different biological analyses performed on sections of a TMA are used to evaluate a reagent for disease diagnosis or treatment (e.g., evaluating a reagent selected from the group of antibodies, genetic probes, and antisense molecules, or a reagent selected from the group of biological inhibitors, biological enhancers, or other biological modulators); identify a prognostic marker for cancer; identify a prognostic marker for a non-cancerous disease; select targets for anti-cancer drug development; prioritize targets for anti-cancer drug development; assess or select therapy for a subject; and/or find a biochemical target for medical therapy.

In specific examples of such analyses, identifying a prognostic marker for cancer or identifying a prognostic marker for a non-cancerous disease involves selecting a marker associated with a poor clinical outcome.

In still other examples of such analyses, selecting therapy for the subject involves selecting an antineoplastic therapy that is associated with a particular biological analysis outcome.

Also provided are methods of analyzing a TMA, which methods involve providing a plurality of elongated biological samples at addressable locations in a block of embedding substrate, such that when the block is frozen and cut into predetermined array sections, a two dimensional array of portions of the biological samples is presented at a surface of each section, with each portion of the biological samples at an addressable location in the array sections, and wherein each biological sample in the block has a third dimension so that when sequential sections of the block are cut, the biological samples maintain a predetermined relationship in the array sections; and exposing a plurality of the array sections to a probe that interacts with one or more of the biological samples of the array, to identify those biological samples that share or differ in a biological property.

In some examples of these methods, the common biological property is a molecular characteristic, such as a presence or absence, or altered level of expression of a protein or gene, alteration of copy number, structure or function of a protein or gene, genetic locus, chromosomal region or chromosome. In some embodiments, the common biological property is correlated with at least one other characteristic of the samples, for instance clinical information (one or more of clinical course, tumor stage, oncogene status, and age of the subject from whom each sample was taken) about a subject from whom each sample was taken.

In one embodiment, thin membranes in a stacked or layered configuration are applied to the sample, such as a tissue section, or protein or nucleic acid gel, and reagents and reaction conditions are provided so that at least a portion of the biomolecules (such as proteins) are eluted from the sample and transferred onto a plurality of the stacked membranes. This produces multiple substantial replicas of the biomolecular content of the sample. The resultant loaded (treated) membranes (or layers) are then separated. Each membrane may be incubated with one or more different detectors (for example antibodies) specific for a particular biomolecule (such as a protein) of interest. The detectors employed are labeled or otherwise detected using any of a variety of techniques, for instance chemiluminescence.

In an example in which proteins are detected, each membrane has essentially the same pattern of proteins bound to it, but different combinations of proteins are made visible (detectable) on each membrane due to the particular detectors (e.g., antibodies) selected to be applied. For example, one membrane layer may display proteins involved in programmed cell death (apoptosis) while an adjacent layer may display proteins involved in cell division such as tyrosine kinases.

In addition to proteins, nucleic acids may be targeted by using labeled DNA probes as detectors in lieu of antibodies. Moreover, different types of target biomolecules may be detected in different layers. For example, both protein and nucleic acid targets can be detected in parallel by applying protein-specific detectors (e.g., antibodies) and nucleic acid detectors (e.g., hybridization probes) to different layers of the array.

According to certain methods of the present disclosure, a sample from which biological molecules are to be transferred (e.g., a tissue section or gel) is positioned in contact with a face of a stack of membranes and both the sample and stack (an assembled "contact transfer stack") are placed inside a fluid impervious enclosure such as a plastic bag or the like. In certain embodiments, the sample is supported by a substantially fluid impervious support, such as a glass slide; in these embodiments, the stack of membranes is placed on the other side of the sample. In other embodiments, the sample from which biomolecules are to be transferred is not supported by an impervious support, and the sample is placed between members of the membrane stack, such that one or more membranes is placed adjacent to each of two faces of the sample.

Also within the enclosure is a liquid transfer reagent. Heat and/or pressure are applied to the contents of the enclosure (from one or both sides) so as to permit proteins and other molecules to be transferred from the sample to the membrane stack. This produces multiple copies or replicas of the biomolecular content of the tissue sample. The processed membranes (or layers) then may be separated and incubated with one or more different probes (e.g., nucleic acid hybridization probes or antibodies) specific for particular targets of interest. The probes employed are labeled or otherwise detectable using any of a variety of techniques such as chemiluminescence.

While each membrane has essentially the same pattern of biomolecules (including proteins and/or nucleic acids) bound to it, different combinations of such biomolecules are made visible on each membrane due to the particular probes or antibodies selected to be applied. For example, one membrane layer may be used to detect proteins associated with disease, for example breast cancer, while an adjacent layer may be used in detecting proteins associated with normal breast epithelium. In another embodiment, one membrane layer may be used to detect proteins associated with pancreatic cancer, while an adjacent layer may be used in detecting proteins associated with thyroid cancer.

In one embodiment, the disclosed methods may be used for a side-by-side comparison of the protein expression patterns in different archival tissue samples, for instance from patients with different diseases, disease outcomes, or responses to therapies. Thus, for example, where patient response to a particular drug can be correlated to a specific protein expression pattern from the diseased organ this provides a useful tool for predicting whether future patients likely will benefit or be harmed by that drug.

In another embodiment, the disclosed methods may be used for a side-by-side comparison of disease state tissue, such as advanced stage prostate cancer, with a normal prostate tissue section. Thus, for example, the expression profile of normal prostate tissue can be used as a baseline for monitoring progression of prostate disease in a subject by contrasting the expression profile of a normal prostate section with a dysplasia section or with an advanced stage prostate section. In another embodiment, the protein expression profile of a normal tissue can act as a template to detect prostate cancer in a sample by contrasting the protein expression profile or expression of nucleic acid markers of interest in the normal prostate section against an unknown disease state section, wherein observations of new or significantly different protein or nucleic acid expression profiles may be an indicator of advanced disease state.

In a particular embodiment, an advanced disease sample and normal tissue sample can be compared against a sample of unknown disease state. Thus, the expression profile of the unknown disease state sample can be compared against both the diseased and disease free sample to identify where, in the transitional process the unknown sample is.

Advantageously, the provided methods may be used to screen archival tissue, which is usually formalin fixed and paraffin embedded. Provided methods may also be used for examination of proteins that cannot be detected with antibodies in situ but can be detected after the protein has been transferred onto a membrane. Furthermore, provided methods enable the quantitative analysis of targets in tissue, for example, the quantification of cell surface receptor density on malignant cells.

Beneficially, the methods, device, arrays, and kits provided herein can be used with laser capture micro dissected samples, permitting molecular analysis of tissue without protein or nucleic acid purification as a prerequisite. These embodiments retain the two-dimensional relationship of distinct cell populations within the same tissue section so as to preserve the spatial relationships between the dissected cells and permit different cell types to be processed and analyzed in parallel.

Thus, methods are provided for detecting biomolecules in a sample collected by LCM, by eluting the biomolecules away from the microdissected sample and binding them to one or more membranes in a layered or stacked configuration, then visualizing the biomolecules on the membranes.

In examples of such methods, cellular samples embedded in/on an LCM transfer film (or the like) are positioned adjacent to a stack of one or more membranes, and reagents and reaction conditions are provided so that the biomolecules are eluted from the cellular sample and transferred onto the membrane(s). Biomolecules on the membrane then can be detected and visualized using detector molecules (e.g., antibodies or DNA probes) having specific affinity for the biomolecule(s) of interest.

Also provided are methods for identifying and analyzing biomolecules that have been resolved via electrophoretic, chromatographic, or fractionating means. Examples of such methods are sensitive enough to detect proteins in low abundance, yet able to detect large numbers of proteins in a high-throughput manner preferably without requiring expensive and sophisticated laboratory equipment.

Thus, according to one aspect of a method of the present disclosure, biomolecules (e.g., proteins or nucleic acids) that have been electrophoretically separated on a gel are transferred from the gel onto a stack of membranes. In certain examples, these membranes are constructed and/or chemically treated to have a high affinity but low capacity for the biomolecules. This allows the creation multiple replicates of the molecular content of the gel. After transfer, the membranes are separated and each is incubated with a one or a unique mixture (also referred to as a "cocktail") of detectors (e.g., antibodies specific for a particular subset of proteins, nucleic acid probes, etc). Thus, while each membrane has essentially the same pattern of biomolecules bound to it, different combinations are made visible on each membrane due to the particular detector (or set of detectors) selected to correspond to the particular layer. In specific examples, the detector cocktail is an antibody cocktail that has been carefully formulated so that no two antibodies in a cocktail bind overlapping or adjacent protein spots. Thus, protein spots that are too close together to be discriminated on a single membrane are detected on separate membranes according to the inventive method herein.

According to certain disclosed methods, proteins that have been separated (either by in situ synthesis, electrophoretically, chromatographically, etc.) on a gel, tissue or other support are transferred from the gel/support onto the membrane stack to allow the creation of multiple replicates or imprints of the protein content of the gel/support. With regard to gels, the amount of protein loaded into the wells is greater than the amount conventionally loaded so as to permit a more even and uniform distribution of the proteins throughout the stack.

Since antibodies can be used to detect many post-translational protein modification (e.g. phosphorylation), certain examples of disclosed methods can be employed to identify or analyze protein function as well as structure. For example, the use of phospho-specific antibodies can be used in the disclosed methods to detect the presence of phosphorylated proteins in the sample. Conversely, the inability to detect phospho-specific binding in the method may be construed as no appreciable level of phosphorylated proteins being present in the sample. In addition to 2-D gels, described methods can be used for one-dimensional gels such as the identification of transcription factors separated by a gel-shift assay.

In detail, one specific embodiment is a method of analyzing the proteome of a biological sample. Such a method involves separating the protein of interest from another protein present in the sample; transferring a portion of the separated protein to a plurality of membranes (for instance, 2, 10, 20 or more) in a stacked configuration; incubating each of the membranes in the presence of one or more species of predetermined ligand molecules (e.g., 2, 10, 20 or more) under conditions sufficient to permit binding between the separated protein and a ligand capable of binding to such protein; and analyzing the proteome by determining the occurrence of binding between the protein and any of the species of predetermined ligand molecules.

Another embodiment is a method for analyzing the extent of similarity between the proteomes of two or more samples. Such a method involves, for each such sample, separating a protein of such sample from another protein present in the sample; transferring a portion of the separated protein to a plurality of membranes (e.g., 2, 10, 20 or more) in a stacked configuration; incubating two or more of the membranes in the presence of one or more species of predetermined ligand molecules (e.g., 2, 10, 20 or more) under conditions sufficient to permit binding between the separated protein and a ligand capable of binding to such protein; and analyzing the extent of similarity between the proteomes by comparing the separated proteins of each such sample with the separated proteins of another such sample for the occurrence of binding between the separated protein and any of the species of predetermined ligand molecules.

Another embodiment is a method for uniquely visualizing a desired predetermined protein if present in a biological sample. This method involves separating the proteins present in the sample from one another; transferring a portion of the separated proteins of the sample to a plurality of membranes (for instance, 2, 10, 20 or more) in a stacked configuration; incubating two or more of the membranes in the presence of one or more species of predetermined detector/ligand molecules (e.g., 2, 10, 20 or more) under conditions sufficient to permit binding between desired predetermined protein and a ligand capable of binding to such protein; and visualizing any binding between the protein and any of the species of predetermined ligand molecules.

Also provided are embodiments of all such methods wherein the separation of the protein from another protein present in the sample is accomplished by electrophoresis (for instance, 2-dimensional (2-D) gel electrophoresis).

Further embodiments include all such methods wherein the sample is obtained from mammalian cells or tissue, and particularly from human cells or tissue, and the embodiments wherein the mammalian cells or tissue are human cells or tissue and the separated protein is a product of a human gene.

It is contemplated that the detector/ligand species can be any of a variety of molecule types. Thus, also provided are embodiments of all such methods wherein at least one of the species of detector/ligand is an antibody, an antibody fragment, a single chain antibody, a receptor protein, a solubilized receptor derivative, a receptor ligands, a metal ion, a virus, a viral protein, an enzyme substrate, a toxin, a toxin candidate, a pharmacological agent, a pharmacological agent candidate, a hybridization probe, a oligonucleotide, and others as discussed herein.

Other embodiments include all such methods wherein the binding of at least one of the species of detector/ligand is dependent upon the structure of the separated biomolecule (e.g., protein or nucleic acid). It still further provides the embodiments of all such methods wherein the binding of at least one of the species of detector/ligand is dependent upon the function of the separated biomolecule (e.g., a phosphorylated protein versus a non-phosphorylated protein).

The disclosure also provides all such methods wherein at least one of the membranes is incubated with more than one species of ligand or detector molecule. Also provided are embodiments of all such methods wherein at least two membranes are employed, at least 10 membranes are employed, or at least 20 membranes are employed.

Further provided are the embodiments of all such methods wherein at least at least two ligand species or detector molecules are employed, wherein at least 10 are employed, or at least 20 or more are employed.

Additional embodiments are membranes that have a high affinity but a low capacity for proteins and/or other biomolecules so as to allow the creation of multiple replicates or imprints of the proteins eluted from a gel. Examples of these membranes are substantially thinner than those conventionally used for blotting. The membranes are optionally provided with (or within) a frame, so that they may be easily handled and manipulated when separated from that stack. The frame optionally defines a channel to permit release of air and fluid trapped between adjacent membranes. Removable tabs or the like also may be provided on each frame to permit the stack to be held together, for instance when it is applied to the gel.

Loaded membranes may be scanned or otherwise digitally imaged using one of several commercially available scientific imaging instruments (for example, Image Quant). Imaging instrumentation and software, such as those described herein, may be employed to permit viewing, analysis, and/or interpretation of the expression patterns from the sample (e.g., a tissue sample or other two-dimensional source, such as a gel). Software may be provided with template images corresponding to each of the membrane images. This allows the identity of the biomolecule in each defined locus (e.g., a spot on a 2-D gel, a band on a 1-D gel, or a localized molecular deposit in a tissue sample) to be confirmed based on its vertical and horizontal position. The software also can allow the density of each locus to be calculated so as to provide a quantitative read-out. The software may also have links to a database of images generated from other gels to allow comparisons to be made between different diseased and normal samples. In addition to computerized analysis of membranes, the source sample (e.g., actual tissue sections or other substantially two-dimensional source) or a substantially similar sample (e.g., an adjacent tissue slice) may be analyzed with conventional techniques (e.g., histochemical techniques) to confirm or compare the digital analysis.

Also provided in another embodiment is a kit for uniquely visualizing a desired predetermined protein such as, a cancer associated protein, if present in a biological sample. Such a kit includes a plurality of membranes, each having a specific affinity for at least one cancer associated protein, and a plurality of detector/ligand species (e.g., species such as an antibody, an antibody fragment, a single chain antibody, a receptor protein, a solubilized receptor derivative, a receptor ligand, a metal ion, a virus, a viral protein, an enzyme substrate, a pharmacological agent, and a pharmacological agent candidate), each adapted to detect the desired cancer associated protein if bound to the membranes. In particular embodiments, the membranes described above include a porous substrate having a thickness of less than about 30 microns. Particular examples of such a kit include membranes that are polycarbonate membranes, especially polycarbonate membranes coated with a material for increasing the affinity of the membrane to biomolecules, for instance nitrocellulose, poly-L-lysine, or mixtures thereof.

Contemplated herein are multiple methods for transferring cancer associated proteins from a sample that is generally substantially two-dimensional into one or more thin membranes. Several different transfer methods are contemplated including wicking transfer, contact transfer, gel-based transfer, bi-directional transfer, transfer from laser capture microdissection samples and microarray transfer. Some of these modes overlap, in that wicking and or contact transfer can be used to transfer proteins from both tissue or gel-base samples, and so forth. Even though not explicitly enumerated, all variations and combinations of the described method are encompassed herein. In particular, the transfer methods disclosed by U.S. Pat. Nos. 6,969,615 and 6,951,761 are incorporated herein by reference in their entirety.

Additionally, it is not a prerequisite that the transfer of cancer associated proteins from a sample occur via transfer to a membrane for quantification. For example, highly sensitive methods that elute, substantially purify, or isolate cancer associated proteins (or nucleic acids that encode them) of interest as a fraction from a sample, may also be used as techniques to evaluate and quantify cancer associated proteins (or the corresponding nucleic acid expression profiles). For example, it is anticipated by the instant disclosure that one of ordinary skill in the art can use HPLC coupled with mass spectrometry to detect, isolate, and substantially purify cancer associated proteins from a sample and that the identified/detected cancer associated proteins can be used to obtain a biomarker indicator indicative of the presence of cancer or a particular disease state (e.g., early or advanced stage).

VIII. Types of Samples

Any two-dimensional sample material that contains releasable biomolecules can be used as a source of biomolecules in the provided transfer processes. By "two-dimensional" it is meant that the material is, or can be formulated so that it is, substantially flat and relatively thin. Representative examples of substantially two-dimensional samples include tissue samples such as thin section slices (e.g., archival or frozen tissue samples), tissue arrays, cDNA or other nucleic acid microarrays, protein microarrays, 1-D protein gels, 1-D nucleic acid gels, 2-D protein gels, and so forth.

It is further contemplated that the described transfer methods, arrays, and devices can be used in forensic procedures to detect and study biological material such as bodily fluids; and so forth. In order to provide the sample in a substantially flat and thin format, substances may be suspended in a liquid or gas, then run through and optionally affixed to a filter such as a sheet of filter paper, with the filter then used as the transfer sample. Generally these samples can be referred to as structurally transformed samples, because their format is altered to render them substantially two dimensional prior to transfer onto a membrane stack. There are also art recognized methods for modified single/fluid based cell samples (e.g., leukemic cell samples) to present like tissue for a TMA or other approaches. See, for instance, Hewitt, *Methods Mol Biol.* 264:61-72, 2004.

Embodiments provided herein may be used to identify biomolecules (e.g., proteins or nucleic acids) in any biological sample including bodily fluids (e.g. blood, plasma, serum, urine, bile, cerebrospinal fluid, aqueous or vitreous humor, or any bodily secretion), a transudate, an exudate (e.g. fluid obtained from an abscess or any other site of infection or inflammation), fluid obtained from a joint, and so forth. Additionally, a biological sample can be obtained from any organ or tissue (including or autopsy specimen) or may comprise cells.

IX. Membranes

With respect to two-dimensional transfer of biomolecules (such as proteins) to a membrane (or set of membranes) for detection and/or quantification, multiple types of membranes are contemplated for use with the described methods.

In particular embodiments, the membranes comprise a material that non-specifically increases the affinity of the membrane to the biological molecules, or class of biomolecules (such as proteins or nucleic acids), that are moved through the membranes. For example, the membranes may be dipped in, coated with, or impregnated with nitrocellulose, poly-L-lysine, or mixtures thereof.

In one embodiment, the membranes are sufficiently thin to allow the biomolecules to move through the plurality of membranes (for example 10, 50 100 or more) in the stack. The membranes may be made of a material that does not substantially impede movement of the biomolecules through the membranes, such as polycarbonate, cellulose acetate or mixtures thereof.

The material of the membranes may maintain a relative relationship of biomolecules as they traverse through the membranes, so that the same biomolecules move through the plurality of membranes at corresponding positions. In such examples, the relative relationship allows the different membranes to be substantial "copies" of one another.

In some embodiments, the membranes will be present as a stack of membranes that will include at least 2, at least 5, at least 10, at least 20, at least 50, or even more individual membranes. Representative membranes for use in methods that utilize a membrane to detect and/or quantify biomolecules of interest, include having a high affinity for protein and/or other biomolecules, but that have a low capacity for retaining such molecules. This binding profile permits biomolecules to pass through the membrane stack with only a limited number being trapped on each successive layer, thereby allowing multiple "copies" of the biomolecules in the sample to be generated. In other words, the low capacity allows the creation of multiple replicates as only a limited quantity of biomolecules is trapped on each layer.

To maintain the binding capacity of the membrane sufficiently low to avoid trapping of too much sample, the thickness of the substrate is for example, less than about 30 microns, and in particular embodiments is between 4-20 microns, for example between about 8-10 microns. The pore size of the substrate is, for example between 0.1 to 5.0 microns, such as about 0.4-0.6 microns, and more specifically 4.0 microns. Another advantage of using a thin membrane is that it lessens the phenomenon of lateral diffusion. The thicker the overall stack, the wider the lateral diffusion of biomolecules through the stack.

It will be appreciated that because the size of the membranes in the stack/array can be varied, the user has the option of analyzing a large number of different samples in parallel, thereby permitting direct comparisons between different patient samples (e.g., different patient samples, or patient samples and a reference standard, or samples of different tissues, etc.). For example, different samples from the same patient at different stages of diseases can be compared in a side-by-side arrangement, as can samples from different patients with the same disease, e.g., lung or another cancer.

In another embodiment, each of the membranes comprises a ligand coating (e.g., a unique ligand coating, in that it is different from the other ligands in the membrane stack) that selectively binds to proteins in the biological sample based on a particular characteristic of the protein chemistry (e.g., hydrophobicity, carbohydrate content, etc). Additionally, the unique ligand coating may bind to proteins in the biological sample based on a particular functionality of the protein (e.g., phosphorylated, methylated).

Contemplated herein are multiple types of membranes that are applicable for use with the methods described herein, for example, with a two-dimensional transfer assay of biomolecules. Several different types of membranes are contemplated. Some of these membrane types overlap, in that a first membrane comprising a protein chemistry based ligand coating and a second membrane comprising a protein functionality based ligand coating can be used simultaneously in a membrane stack to transfer biomolecules from a sample. Even though not explicitly enumerated, all variations and combinations of the described methods are encompassed herein. In particular, types of membranes and analysis of membranes disclosed in U.S. Pat. Nos. 6,969,615 and 6,951,761 are incorporated herein by reference in their entirety.

After material transfer from the sample to the membrane or set of membranes, the processed membranes (or layers) can be separated and each incubated with one or more different detector molecules (such as nucleic acid hybridization probes, lectins, or antibodies) specific for particular targets of interest. In certain embodiments, the detectors/probes employed are labeled or otherwise detectable using any of a variety of techniques such as chemiluminescence. Thus, in some instances, where each membrane has essentially the same pattern of biomolecules bound to it, different combinations of biomolecules can be made observable on each membrane by selecting particular probes to be applied and detected.

By way of example, one membrane layer may display proteins involved in a disease state, such as cancer, while an adjacent layer may display proteins involved in normal tissue such as a "housekeeping" protein.

In addition to proteins, nucleic acids may be targeted and detected by using labeled DNA hybridization probes rather than antibodies. Moreover, both protein and nucleic acid targets can be detected in parallel by applying both antibodies and nucleic acid probes to different layers of the membrane stack. Digital images of membranes may be created using a variety of instruments including the Image Station® CCD instrument available from Kodak Scientific Imaging (New Haven, Conn.). Alternatively, images may be captured on film (such as X-ray film) and digitalized by flat bed scanners. Software is preferably provided to align the images and perform densitometry functions. In examples using densitometry, the user can select the region of interest for analysis and the signal intensities are recorded and normalized. The numerical intensity values are then compared.

For analysis of transferred proteins, after the transfer by any of the herein-described membrane based protein-transfer techniques, the membranes are separated from the stack and each is incubated in a separate solution of primary antibody specific for a desired protein. Only the area of the membrane containing the desired protein binds the antibody, forming a layer of antibody molecules. After incubation for about 1-8 hours, the membranes are usually washed in buffer to remove unbound antibody.

For detection of the proteins on the membranes (in the form of bands, spots, or "in situ" from tissue sections), the loaded membranes are incubated with a secondary antibody that binds to the primary antibody. The secondary antibody may be covalently linked to an enzyme such as horseradish peroxidase (HRP) or alkaline phosphatase (AP) that catalyzes substrate and the protein/antibody complex can be visualized using a number of techniques such as ECL, direct fluorescence, or colorimetric reactions. Commercially available flatbed scanners may be employed in conjunction with film. Alternatively, specialized imaging instrumentation for ECL, such as the Kodak IMAGE STATION available from NEN may be utilized and digital imaging software can be employed to display the images according to the preference of the user.

In lieu of antibodies, other ligands may be employed as detectors. Ligands can be antibody fragments, receptors, receptor ligands, enzymes, viruses or viral particles, enzyme substrates or other small molecules that bind to specific proteins. Moreover, in addition to identifying cancer associated proteins of interest, kits can also be employed to identify the functional state of the cancer associated proteins. One way to do so is to use phospho-specific antibodies to determine the phosphorylative state of a protein of interest. Another approach to identify protein function is to first renature the proteins on the membranes by any of a number of techniques known in the art such as incubating the membrane in Triton-X® (octylphenol polymerized with ethylene oxide). Once renatured, proteins will regain their enzymatic activity and one of several substrate degradation assays known in the art can be used. With this approach the activity of kinases, phosphates and metalloproteinases can be determined.

Panels of proteins of interest for scientific research may be grouped by the proteins being involved in a particular cellular phenomenon such as apoptosis, cell cycle, signal transduction, etc. Panels of proteins for clinical diagnostics may be grouped by proteins associated with a particular disease such as prostate cancer or breast cancer, etc.

In many embodiments, the detectors/ligands employed are labeled or otherwise made detectable using any of several techniques, such as enhanced chemiluminescence (ECL), fluorescence, counter-ligand staining, radioactivity, paramagnetism, enzymatic activity, differential staining, protein assays involving nucleic acid amplification, etc. The membrane blots are preferably scanned, and more preferably, digitally imaged, to permit their storage, transmission, and reference. Such scanning and/or digitalization may be accomplished using any of several commercially available scientific imaging instruments (see, e.g., Patton et al., *Electrophoresis* 14:650-658, 1993; Tietz et al., *Electrophoresis* 12:46-54, 1991; Spragg et al., *Anal Biochem.* 129:255-268, 1983; Garrison et al., *J Biol. Chem.* 257:13144-13149, 1982; all herein incorporated by reference).

Examples of probes (such as antibodies) or detector cocktails that are useful in the analysis, detection and/or quantification of a cancer are described in Section V herein.

X. Example Detection Chemistries with Detector Cocktails

In certain embodiments, after proteins have been transferred through the membrane stack, individual membranes layers are separated and each is incubated in a separate antibody (or other detector molecule) cocktail. A key advantage of creating multiple replicate blots is that many more detector molecules (e.g., antibodies) can be usefully employed than if all of the detectors had to be crowded onto a single blot.

An exemplary process for designing the ligand cocktails—and for determining which proteins will be identified on each membrane layer—is provided below. First a panel of cancer associated proteins of interest is selected, such as PTEN, p-AKT, p-mTOR, p-MAPK, EGFR, HER2, and HER3 (or some subset thereof). These can be randomly selected proteins and/or proteins that are not directly related to one another, or may be groups of known proteins previously implicated to play a role in one or more particular cellular phenomena (e.g. apoptosis or growth factor pathways) or a particular disease (e.g. prostate cancer specific antigen, PSA). In some instances, these will be cancer associated proteins that have been characterized by sequence or coordinates on 2-D gels or for which ligands have been or could be generated. Databases of annotated 2-D gels include the Quest Protein Database Center (on-line at //siva.cshl.org), the Swiss 2-D PAGE database (on-line at //expasy.cbr.nrc.ca/ch2d), Appel et al. *Electrophoresis.* 14(11):1232-1238, 1993; the Danish Centre for Human Genome Research (on-line at //biobase.dk/cgi-bin/celis), Celis et al., *FEBS Lett.* 398(2-3):129-134, 1996, etc. Antibodies may be obtained from a variety of sources such as BD Transduction Laboratories (Lexington, Ky.) or Santa Cruz Biotechnology (Santa Cruz, Calif.).

Although, as discussed above, any of a broad class of ligands may be employed, for simplicity the embodiment is illustrated with reference to the use of antibody ligands. Immunological identification of the cancer associated proteins on the membranes thus preferably involves the selection of antibodies having a high affinity and specificity for their protein targets. However, antibodies (monoclonal or polyclonal) frequently recognize more than one protein in Western blotting detection. This cross-reactivity phenomenon becomes increasingly apparent as the concentration of antibody increases relative to that of the sample proteins. Hence, the first step in the antibody selection process preferably involves choosing antibodies (and their working concentrations) that consistently visualize preferably one but no more than five proteins on the same membrane. When the detector antibody binds to more than one spot, the undesired proteins ("false spots") can be eliminated based on their X-Y positions on the membranes. Since the molecular weight and charge (pI) of a given protein is generally constant, it should appear at about the same coordinates on the gel each time it is run.

If two or more proteins in a sample are of similar size and charge—and therefore migrate to the same general vicinity on the gel—they would likely create overlapping spots if detected on the same membrane. Therefore, in a preferred embodiment, examples of the methods disclosed herein avoid this problem by designing an antibody cocktail to detect adjacent or overlapping cancer associated proteins on different membranes.

Once assembled, the antibody cocktails will be additionally tested for their specificity by control tests. For example, in a first test, membranes made from the transfer of a single gel (or from several gels that contain the same sample and were prepared in the same manner) will be probed with cocktails that differ in only one antibody component (each cocktail will lack one of the antibodies). As a result of this procedure, immunoblotted membranes should differ from each other in only one spot.

Each cocktail can also include one or more antibodies against "housekeeping" proteins (i.e., abundant structural proteins found in all eukaryotic cells such as actin, tubulin, etc.). Thus, for example, the antibodies employed will contain an antibody to actin, which will result in the production of a spot. These antibodies serve as internal landmarks to normalize samples for loading differences and to compensate for any distortion caused by the gel running process. Once the cocktails are designed, they can be reused in any kit that seeks to identify the same panel of proteins that were identified in creating the cocktails, regardless of the origin of the sample.

It will be appreciated that the present disclosure allows not only the simultaneous characterization of a large number of different cancer associated proteins but also permits the characterization of a large number of characteristics of a single protein based on the number of different characteristics. For example, the protein p70 S6 kinase, required for cell growth and cell cycle progression, is activated by phosphate group attachments (phosphorylation) to threonine on position 229 and/or 389 of the protein. Identification of this kinase would provide not only a determination of its presence or absence but also a demonstration of its activity. By way of example, with a kit containing at least a four-membrane stack, four copies can be made of a 2-D gel. The first membrane would be incubated in antibody specific for the whole protein to determine if this protein is present in the sample or not. The second membrane can be used in a kinase assay to determine if the protein is active or not. The third membrane can be probed with phospho-p70 S6 kinase (Thr229) antibody to determine if activity of the enzyme is due to activation of this site. The fourth membrane can be probed with phospho-p70 S6 Kinase (Thr389) antibody to determine if the activity of the enzyme is due to activation of this site. And since all of these tests are done on the single sample (rather than different batches of the same sample) the information obtained is more reliable.

Antibody cocktails are preferably stored in vials, preferably made of plastic or glass, and are optionally combined in a kit to create a "panel" of protein targets of interests. Panels for scientific research may be grouped by the proteins involved in a particular cellular phenomenon such as apoptosis, cell cycle, signal transduction, etc. Panels for clinical diagnostics may be grouped by proteins associated with a particular disease such as prostate cancer or breast cancer, etc.

XI. Representative Cancer Applications (a) Breast Cancer

Breast cancer is the most common form of cancer in women and is the second leading cause of cancer-related deaths in women living in the United States, with more than 40,000 women dying from the disease each year. Identification of breast cancer specific molecular targets has enormous potential to enhance detection, treatment, and prognosis of breast cancer disease. In addition, understanding the role of breast cancer specific molecular targets in the process of transformation could reveal additional opportunities to therapeutically target other breast cancer specific targets, such as cancer associated proteins in the same or related cell signaling or growth factor pathways. Consequently, the instant disclosure contemplates methods for detecting breast cancer specific cancer associated proteins in a sample comprising a TMA that incorporates a probe that is specific for the detection of the breast cancer specific cancer associated protein; identifying the breast cancer specific cancer associated protein in the sample; and thereby correlating the presence of the breast cancer specific cancer associated protein with the presence of, or increased risk of, developing breast cancer. The methods disclosed herein identify a simplified molecular signature for the identification of tumors and for the determination of relative survival rates of such tumors. For example, an advanced disease breast cancer sample can be probed using antibodies raised specifically against proteins known to be expressed in a disease state tissue. In one example, an antibody cocktail comprising epidermal growth factor receptor (EGFR), HER2/neu, as well as the downstream activation factors, extracellular signal-regulated kinase 1/2 (ERK1/2), AKT, initiation factor 4E-binding protein 1 (4E-BP1), phosphorylated ribosomal protein S6 kinase 1 (p70S6K1), and ribosomal protein S6 (S6), all elements of the signaling pathway in breast cancer, can be applied to the one or more membranes of a TMA. Subsequent immunodetection and secondary fluorescent antibodies can be applied to the membrane(s) of the TMA and signal intensities of the cancer associated proteins can be quantified by molecular scanning densitometry software. In a further embodiment, the intensities of the cancer associated proteins can be compared to the total cellular content of the sample to obtain a biomarker indicator. In a further embodiment, the biomarker indicator can be correlated with relative cancer rates of survival. In one embodiment, the sample is studied by immunohistochemistry using phosphorylation-specific antibodies for the detection of activated (phosphorylated) breast cancer specific cancer associated proteins. Identification of breast cancer specific cancer associated proteins in the sample may correlate with the presence of breast cancer, an increased risk of developing breast cancer, or a decrease in overall survival rate for a subject with breast cancer.

In another example, expression of breast cancer specific cancer associated proteins measured in a breast tumor sample can be correlated with pathologic grade, patient survival, and tumor recurrence to determine which, if any, of the cancer associated proteins can be used as a molecular signature for breast cancer. For example, if a protein such as 4E-BP1, is activated in a high percentage of breast tumors, and is associated with higher malignant grade, tumor size, and local recurrence, the protein 4E-BP1, can be proposed as a molecular signature in the cell signaling of breast cancers and therefore applied as a breast cancer specific cancer associated protein.

Activation of the Src pathway is thought to cause resistance to standard medical treatment in some patients with breast cancer. Thus, in another example, inhibiting the Src signaling pathway while providing standard of care treatment might overcome some aspects of drug resistance in affected patients. Understanding which parts and proteins of the Src pathway to measure in human tumors is therefore important when developing a molecular diagnostic tool that will allow oncologist's to select an appropriate signal transduction inhibitor in the clinic.

Again, with respect to breast cancer, C35 is a protein abundantly expressed in breast cancer cells (C17orf37). Anti-C35 antibodies can be utilized by routine immunohistochemistry techniques to confirm expression of the gene product of C35 in human tumors and normal tissues. For example, C35 is found to be highly expressed in breast carcinoma compared with normal breast epithelium and other normal tissues. Accordingly, C35 may be used in the disclosed methods as a potential molecular target for the therapeutic treatment of breast cancers or alternatively, as a molecular signature for the positive identification and detection of breast cancer in a sample.

(b) Prostate Cancer

One of the major dilemmas in managing patients with prostate cancer is that only a fraction of cases would lead to cancer-related death if left untreated but because of the extremely high prevalence rate of prostate cancer its mortality rate in men is second only to lung cancer. Consequently, there is a great public health need to accurately assess the risk of disease progression in patients with prostate cancer so that appropriate treatment options can be considered. If a reliable method for monitoring disease progression was identified, many prostate patients would be able to benefit from "watchful-waiting" protocols rather than undergoing radical prostatectomy. Using the method disclosed herein, candidate cancer associated proteins specific for prostate cancer include, but are not limited to hepsin, pim-1 kinase, AMACR, AIPC, e-cadherin (ECAD), α-methyl;acyl-coenzyme A racemase and EZH2 can be evaluated for use in a method to detect or monitor progression of prostate cancer.

For example, moderate or strong expression of EZH2 coupled with moderate expression of ECAD as detected using the methods disclosed herein may be found to be most strongly associated with the recurrence of prostate cancer, and thus, useful in defining a cohort of high-risk patients that can be offered adjuvant therapy. In another embodiment, it is contemplated that EZH2-ECAD status is highly statistically significant with disease recurrence after radical prostatectomy, suggesting that EZH2-ECAD positive tumors require more aggressive treatment. Accordingly, EZH2-ECAD negative tumors may be considered a valuable selection tool for the development of watchful-waiting protocols aiding in the definition of low-risk disease for prostate cancer.

In one embodiment, there is disclosed the identification of cancer associated proteins that are indicative of prostate cancer. The present disclosure further provides cancer associated proteins that are useful for the diagnosis, detection, characterization and prognosis of prostate cancer. The present disclosure also provides methods for characterizing prostate tissue in a subject comprising, providing a prostate tissue sample, detecting protein expression levels of at least two cancer associated proteins, comparing the protein expression levels of the at least two cancer associated proteins to a non-cancerous control sample, wherein a change in the protein expression level of the two cancer associated proteins as compared to the non-cancerous sample is associated with an increased risk for developing prostate cancer.

In one embodiment, the two or more cancer associated proteins are selected from the group consisting of HEPSIN, FKBP5, FASN, FOLH1, TNFSF10, PCM1, S100A11, IGFBP3, SLUG, GSTM3, IL1R2, ITGB4, CCND2, EDNRB, APP, THROMBOSPONDIN 1, ANNEXIN A1, EPHA1, NCK1, MAPK6, SGK, HEVIN, MEIS2, MYLK, FZD7, CAVEOLIN 2, TACC1, ARHB, PSG9, GSTM1, KERATIN 5, TIMP2, GELSOLIN, ITM2C, GSTM5, VINCULIN, FHL1, GSTP1, MEIS1, ETS2, PPP2CB, CATHEPSIN B, COL1A2, RIG, VIMENTIN, MOESIN, MCAM, FIBRONECTIN 1, NBL1, ANNEXIN A4, ANEXIN A11, IL1R1, IGFBP5, CYSTATIN C, COL15A1, ADAMTS1, SKI, EGR1, FOSB, CFLAR, JUN, YWHAB, NRAS, C7, SCYA2, ITGA1, LUMICAN, C1S, C4BPA, COL3A1, FAT, MMECD10, CLUSTERIN, and PLA2G2A.

In one embodiment, the disclosure additionally provides a method for detecting prostate cancer in a subject, comprising: providing a sample from a subject, calculating the protein expression level of at least two cancer associated proteins relative to the protein expression levels of a non-cancerous prostate tissue sample, wherein the two or more cancer associated proteins are selected from the group consisting of IGFBP5, MADH4, NBL1, SEPP1, RAB2, FAT, PP1CB, MPDZ, PRKCL2, ATF2, RAB5A, and Cathepsin H, wherein decreased expression of the cancer associated proteins in comparison to a normal non-cancerous sample is diagnostic of metastatic prostate cancer.

In another embodiment, the method further provides a method for characterizing prostate cancer in a subject, comprising providing a tumor sample from a subject diagnosed with prostate cancer, detecting increased expression of at least two cancer associated proteins relative to a non-cancerous prostate tissue of two or more cancer associated proteins selected from the group consisting of CTBP1, MAP3K10, TBXA2R, MTA1, RAP2, TRAP1, TFCP2, E2-EPF, UBCH10, TASTIN, EZH2, FLS353, MYBL2, LIMK1, TRAF4, wherein increased expression of the two or more cancer associated proteins is diagnostic of metastatic prostate cancer.

(c) Lung Cancer

Surgery is typically the first line of therapy for primary lung cancer, which is then followed up by radiation and/or chemotherapy. After removal of the primary tumor, a significant proportion of patients undergoing resection manifest evidence of non-detectable metastatic disease and show low survival rates. Using the methods disclosed herein it is contemplated that a user can evaluate capabilities for discovering cancer associated proteins of metastatic lung cancer directly from a sample, for example, a formalin-fixed archival lung cancer tissue section. Of particular interest are protein expression profiles for lung cancer specific cancer associated proteins such as carcinoembryonic antigen (CEA), CYFRA21-1, plasma kallikrein B1 (KLKB1), Annexin A3, CKs, Prx I, II, III, fatty acid binding protein, and Neuron-Specific Enolase (NSE).

Consequently, the instant disclosure contemplates methods for detecting lung cancer specific cancer associated proteins in a sample comprising a TMA that incorporates a probe that is specific for the detection of the lung cancer specific cancer associated protein by identifying the lung cancer specific cancer associated protein in the sample; and thereby correlating the presence of the lung cancer specific cancer associated protein with the presence of, or increased risk of, developing lung cancer. The methods disclosed herein identify a simplified molecular signature for the identification of lung cancers and for the determination of relative survival rates of such tumors. For example, an advanced disease lung cancer sample can be probed using antibodies raised specifically against proteins known to be expressed in a disease state tissue. In one example, an antibody cocktail comprising CEA, CYFRA21-1, KLKB1, or NSE, all proteins previously identified in lung cancer samples, can be applied to the one or more membranes of a TMA. Subsequent immunodetection and secondary fluorescent antibodies can be applied to the membrane(s) of the TMA and signal intensities of the lung cancer specific cancer associated proteins can be quantified by molecular scanning densitometry software. In a further embodiment, the intensities of the lung cancer associated proteins can be compared to the total cellular content of the sample to obtain a biomarker indicator. In a further embodiment, the biomarker indicator can be correlated with relative cancer survival rates.

Within lung cancers, the subset, small cell lung cancer (SCLC) is a particularly aggressive form. SCLC is highly sensitive to systemic chemotherapy, but due to its aggressive nature may have disseminated before a diagnosis is made. Thus, a sensitive, reliable and rapid method for the diagnosis of SCLC in order to initiate proper treatment at an early stage is highly warranted. Potential SCLC specific cancer associated proteins that can be evaluated using the methods disclosed herein include, among others, ProGRP, NSE and CEA. In particular, the reference values for these proteins in human serum in healthy subjects vary from pg/mL (ProGRP) to ng/mL (NSE and CEA) levels and thus the detection of these SCLS specific cancer associated proteins can be evaluated through the analysis of a patients' serum using the methods disclosed herein, and is not therefore limited to an analysis by tissue biopsy or tissue block section. For example, to determine the concentrations of the SCLC specific cancer associated proteins an ELISA and RIA can be used. The intensity profiles of the SCLC specific proteins can be normalized using the methods disclosed herein to obtain a biomarker indicator for SCLC. The biomarker indicator can then be used to obtain relative cancer survival rates using the methods discussed herein.

(d) Pancreatic Cancer

In a further embodiment of the disclosure, it is contemplated that a panel of cancer associated proteins can be developed for the use in identification, detection and/or quantification of pancreatic cancer associated proteins in a sample. For example, a panel of five pancreatic cancer associated proteins comprising LCN2, REG1A, REG3, TIMP1, and IGFBP4 may be used to identify precancerous growths (pancreatic intraepithelial neoplasia), that are not observed in cancer patients or healthy control subjects. In one embodiment, the five-cancer associated protein panel is screened against blood samples from subjects to detect the presence of any, or all five proteins. Positive detection of all five proteins in the protein panel is indicative or precancerous lesions in the subject, while detection of one or two proteins from the protein panel at low concentrations may be construed as a subject with currently a low-risk for pancreatic cancer. Accordingly, the five protein panel is potentially useful for the detection of pancreatic cancer, and may also be useful in identifying a cohort of subjects that are at an advanced stage of disease. Moreover, the development of specific cancer or multi-type cancer associated protein panels, such as the exemplary five protein panel discussed above in reference to pancreatic cancer, can be used to monitor, for example, the progression of disease in a subject from precancerous lesions to an advance stage of disease. It will be apparent to one of ordinary skill in the art that the development of a protein panel comprising cancer associated proteins associated with a specific type of cancer (e.g., breast, lung, pancreatic, ovarian) is an objective of the instant disclosure and is hereby contemplated by the instant application. Additionally, it will be readily apparent to one of ordinary skill in the art that the development of a protein panel comprising cancer associated proteins associated with multiple types of cancer (e.g. at least one cancer associated protein from multiple types of cancer, such as breast, lung, pancreatic or ovarian cancer) is an objective of the instant disclosure and is hereby contemplated by the instant application.

(e) Ovarian Cancer

The American Cancer Society estimates that 15,000 women die from ovarian cancer each year. Most patients present with advanced stage disease that has spread beyond the primary tumor site. Overexpression of tissue type transglutaminase (TG2) in ovarian cancer has been associated with increased tumor cell growth, resistance to chemotherapy and lower overall survival rate (Hwang et al., *Cancer Res.* 15:5849-5858, 2008). Accordingly, the methods disclosed herein contemplate a method to detect the presence of ovarian cancer in a sample by calculating the content of at least one ovarian cancer specific cancer associated protein (e.g., TG2) in the sample, normalizing the content of the at least one ovarian cancer specific cancer associated protein, comparing the normalized value of the at least one cancer associated protein against normalized values for a normal non-cancerous sample, and correlating the change in normalized value of the cancer associated protein in the sample versus a non-cancerous sample to detect the presence of ovarian cancer in the sample. Thus, TG2 as defined herein is a cancer associated protein with potential to detect or identify ovarian cancer in a sample using the methods disclosed herein. TG2 is also a potential therapeutic target for the treatment of ovarian cancer and in particular, can be used to monitor the progression of disease or responsiveness of a subject to therapy, especially, chemotherapy-resistant tumors using the methods disclosed herein.

(f) Bile Duct Carcinoma

Extrahepatic cholangiocarcinoma (EHCC) is a malignant neoplasm of biliary tract epithelia arising from hepatic hilum to distal bile duct, and constitutes approximately 80-90% of all cholangiocarcinomas (Malhi and Gores, *J. Hepatol* 2006; 45:856-67). Although EHCC is a relatively uncommon neoplasm in the United States, it is more prevalent in Asia, including Korea (Hong et al., *Cancer* 2005; 104:802-10). Currently, surgical resection is the mainstay of treatment; however it is curative only in a limited number of patients, primarily those without advanced stage disease (Seyama and Makuuchi, *World J. Gastroenterol* 2007; 13:1505-15). For patients who undergo surgical resection, the 5-year survival rate is approximately 20% (Nathan et al., *J. Gastrointest Surg.* 2007; 11:1488-96). Several neoadjuvant therapies, including chemotherapy, radiation therapy, and photodynamic therapy have been studied, but none have shown a significant survival benefit (Thomas, *Crit. Rev. Oncol. Hematol.* 2007; 61:44-51). Therefore, identification of new targets for early detection of EHCC and/or development of new therapeutic regimens for EHCC based on a better understanding of the biological mechanisms are critical for reducing the mortality of EHCC patients.

As already discussed herein, the phosphatidyl inositol 3 kinase (PI3K)/AKT signaling pathway is known to play an important role in regulating tumor cellular survival, apoptosis, and protein translation. PI3K is activated by receptor tyrosine kinases (RTKs), and activation of RTKs leads to allosteric joining to the cellular membrane and subsequent tyrosine phosphorylation of the regulatory subunit of PI3K. PI3K converts phosphatidyl inositol 2 phosphate (PIP2) to phosphatidyl inositol 3 phosphate (PIP3) (Cromwell et al., *Mol. Cancer. Ther.*, 2007; 6:2139-48). AKT is activated by phosphorylation at Thr308 by PIP3 and at Ser473 by the mammalian target of rapamycin (mTOR), as a part of the mTOR complex (mTORC) (Cromwell et al., *Mol. Cancer. Ther.*, 2007; 6:2139-48). The phosphatase and tensin homolog deleted on chromosome 10 (PTEN) is a well-described negative regulator of the PI3K/AKT signaling pathway, which functions as a tumor suppressor gene by induction of G1 phase cell cycle arrest through decreasing the levels of cyclin D1 (Radu et al., *Mol Cell Biol.* 2003 September; 23(17):6139-49). Rapamycin was initially considered as a promising modality for blocking mTOR phosphorylation in several cancer types; however cancer patients with high AKT activity are reported to minimally respond to mTORC1 inhibitors (O'Reilly et al., *Cancer Res.* 2006; 66: 1500-1508). Patients with high expression of activated (phosphorylated) AKT were also reported resistant to radiation therapy (Gupta et al., *Clin Cancer Res.* 2002; 8:855-92). Therefore, what is needed is a new method for the detection of EHCC. In addition what is needed is an accurate and reliable method for determining survival probability for subjects with EHCC.

In one embodiment, the present disclosure relates to compositions and methods for cancer diagnostics, including but not limited to cancer associated proteins. In particular, the present disclosure identifies cancer associated proteins strongly associated with EHCC. The present disclosure further provides novel biomarker indicators, in the form of a ratio-based determination of cancer associated proteins in conjunction with a normalization step, useful for the diagnosis, characterization, prognosis and treatment of EHCC.

In a particular embodiment, the present disclosure provides a method for characterizing EHCC tissue in a subject by providing an EHCC tissue sample from a subject; and detecting the level of protein expression of p-AKT, p-mTOR or PTEN in the sample as compared to the level of protein expression in a non-cancerous sample, thereby characterizing the expression profile of cancer associated proteins in the EHCC tissue sample.

In some embodiments, the subject comprises a human subject. In other embodiments, the subject comprises a non-human mammal. In some embodiments, the sample comprises a tumor biopsy. In some embodiments, the sample is a post-surgical tumor tissue sample and the method further comprises the step of identifying EHCC based on detecting changes in protein expression of p-AKT, p-mTOR or PTEN as compared to a normal tissue sample. In some embodiments, characterizing EHCC tissue comprises identifying a stage of EHCC cancer in the tissue. In some embodiments, the stage includes but is not limited to dysplasia, EHCC and metastatic EHCC. In some embodiments, the method further comprises the step of providing a prognosis to the subject.

In other embodiments, the prognosis comprises an indicator ratio that determines the relative risk for developing EHCC.

In other embodiments, the present disclosure provides a kit for characterizing EHCC cancer in a subject, comprising: a reagent capable of specifically detecting the presence of absence of expression of pAKT, p-mTOR or PTEN; and instructions for using the kit for characterizing EHCC cancer in the subject. In some embodiments, the reagent comprises an antibody that specifically binds to a pAKT, p-mTOR or PTEN polypeptide.

In yet other embodiments, the present disclosure provides a method for characterizing an inconclusive biopsy tissue in a subject, comprising providing an inconclusive biopsy tissue sample from a subject; and detecting the presence of expression of a cancer associated protein in the sample, thereby characterizing the inconclusive biopsy tissue sample. In embodiments specific for the detection of EHCC, the detection step comprises detecting the presence of a p-AKT polypeptide (e.g., by exposing the p-AKT polypeptide to an antibody specific to the p-AKT polypeptide and detecting the binding of the antibody to the p-AKT polypeptide). In some embodiments, the subject comprises a human subject. In some embodiments, the presence of p-AKT expression in the inconclusive biopsy tissue is indicative of EHCC cancer in the subject. In certain embodiments, the method further comprises the step of detecting expression of an additional cancer associated protein, such as p-mTOR or PTEN; and the presence of p-mTOR or PTEN expression (in addition to the presence of p-AKT expression) are indicative of prostate cancer in the subject.

The present disclosure further provides a method of detecting p-AKT, p-mTOR or PTEN expression in a bodily fluid, comprising providing a bodily fluid from a subject; and a reagent for detecting p-AKT, p-mTOR or PTEN expression in the biological fluid; and contacting the bodily fluid with the reagent under conditions such that the reagent detects p-AKT, p-mTOR or PTEN expression in the bodily fluid. In some embodiments, the bodily fluid is selected from the group consisting of serum, urine, whole blood, lymph fluid, and mucus. In certain embodiments, the presence of p-AKT, p-mTOR or PTEN in the bodily fluid is indicative of cancer (e.g., EHCC). In other embodiments, the presence and/or levels of p-mTOR and p-AKT, or p-MAPK and EGFR, or all four (p-mTOR, p-AKT, p-MAPK and EGFR) in a bodily/biological fluid are indicative of cancer, particularly lung cancer.

A more detailed description of aspects of the present invention is provided below. While the described embodiment(s) are representative embodiment(s) of the present invention, it is to be understood that modifications will occur to those skilled in the art without departing from the spirit of the invention. The scope of the invention is therefore to be determined solely by the appended claims.

EXAMPLES

Example 1

Patient Selection and Tumor Sample Collection 221 patients with EHCC who were surgically resected at Asan Medical Center, University of Ulsan College of Medicine in Seoul, South Korea were studied. Carcinomas with the epicenter in the extrahepatic bile duct were included, while carcinomas of the ampulla of Vater or pancreas, and those with obvious precancerous epithelial changes in the ampulla of Vater or pancreas were excluded. Carcinomas arising in the gallbladder, or intrahepatic bile duct with extension to the extrahepatic bile duct were also excluded in this study. Medical records were reviewed to obtain data including age and gender of patients, surgical procedure, survival time, and survival status. Data with tumor location, size, and growth pattern were obtained from reviewing pathology reports. Information on post-operative radiation and/or chemotherapy, and performance status of patients was not available for analysis. Material was obtained with appropriate human protection approvals from the Institutional Review Board of the Asan Medical Center and Office of Human Subjects Research at the NIH.

Tissue Microarray Construction

Tissue Microarrays (TMA) were constructed from archival formalin fixed, paraffin embedded tissue blocks from each of the above EHCC subjects. For each tumor, a representative tumor area was carefully selected from a hematoxylin and eosin stained section of the donor tissue block, using methods known in the art (see, for example, Hidalago et al., *J. Clin. Pathol.* 56:144-146, 2003 and Hong et al., *Mod. Pathol.* 20:562-569, 2007). 20 normal biliary epithelial, 67 biliary dysplasia, and 221 EHCC cases were studied. Each subject was represented with two cores of 1.5 mm diameter from each donor tissue block.

Statistical Analysis

Statistical analyses were performed using SAS (version 9.13) and R (available on the World Wide Web at .rproject.org). Differential expression of p-AKT, p-mTOR, and total PTEN between and among normal biliary epithelia, dysplasia, and EHCC cases was compared by ANOVA and Duncan's tests after normalization of expression. Associations between categorical variables were examined using the Pearson's chi-square and Fisher's exact tests. A recursive partitioning technique coupled with log-rank statistics was employed to identify cutoff points that discriminate outcome of patients based on protein expression (see Example 8). Survival curves were calculated by the Kaplan-Meier method and statistical significance was examined by the log-rank test and the Cox proportional hazards regression model. A p-value of less than 0.05 was considered statistically significant.

Example 2

Proteomic Expression Profiling by Multiplex Tissue Immunoblotting

Multiplex tissue immunoblotting (MTI) was performed as known in the art (for example, Chung et al., *Proteomics.* 6:676-74, 2006 and Chung et al., *Cancer Epidemiol. Biomarkers. Prev.* 15:1403-08, 2006). In brief, TMA slides were deparaffinized and treated with an enzyme cocktail solution [0.001% trypsin plus 0.002% proteinase-K, 10% glycerol, 50 mM $NH_4HCO_3$ pH 8.2 (Fisher Scientific, Hampton, N.H.)] for 30 minutes at 37° C. Slides were subsequently incubated with Probuffer complete protease inhibitor solution [0.5 ml phosphatase inhibitor I (Sigma, St. Louis, Mo.), 0.5 ml phosphatase inhibitor II (Sigma), 1 protease inhibitor tablet (Roche Diagnostics, Indianapolis, Ind.) in 50 ml PBS (pH 7.2)] for 20 minutes at room temperature (RT). The proteins of treated slides were transferred to a 5-membrane stack (set) of P-FILM (20/20 GeneSystems, Rockville, Md.) using Tris-glycine transfer buffer (50 mM Tris, 380 mM Glycine) under serial conditions for 1 hour at 55° C., for 0.5 hours at 65° C., and for 2 hours at 80° C. After protein transfer, the membranes were washed with TBST with Tween 20.

Each membrane was incubated with anti-p-AKT, anti-p-mTOR and total PTEN (1:100 dilution each; Cell Signaling, Danvers, Mass.) overnight and subsequently with FITC conjugated anti-rabbit IgG (1:1000; Molecular Probes, Carlsbad, Calif.) and streptavidin linked Cy5 (1:1000; Amersham Biosciences, Uppsala, Sweden) for 30 minutes. Following immunodetection, total cellular protein content was measured by biotinylation of proteins followed by incubation of the membranes with streptavidin-Cy5. Following fluorescence-based detection (Microarray Scanner, PerkinElmer, Wellesley, Mass.), signal intensity was quantified after inter-array normalization (correcting for background variations within each membrane), followed by determining the ratio of specific protein/total cellular protein content. Inter-array normalization was performed by determining the ratio of specific protein content per membrane versus total cellular protein content for the same membrane.

An optional, second normalization process (intra-array normalization) was performed to compensate for variations between sets of membranes under investigation. Intra-array normalization was performed by adjusting the median expression level of normal biliary epithelia.

Example 3

Immunohistochemistry

Tissue sections were deparaffinized and hydrated in xylene and serial alcohol solutions, respectively. Endogenous peroxidase was blocked by incubation in 3% $H_2O_2$ for 10 minutes. Antigen retrieval was performed in a steam pressure cooker with prewarmed antigen retrieval buffer pH 10 (Dako, Glostrup, Denmark) at 95° C., for 10 minutes. To minimize non-specific staining, sections were incubated with protein block (Dako) for 15 minutes. Primary antibodies were incubated overnight at 4° C. Antigen-antibody reactions were detected with DAKO LSAB+ peroxidase kit and DAB. Anti-p-AKT, anti-p-mTOR, and PTEN antibodies (Cell Signaling) were used at a dilution of 1:200. Immunostained sections were lightly counterstained with hematoxylin, dehydrated in ethanol, and cleared in xylene.

Example 4 p-AKT and p-mTOR Expression

The expression patterns of p-AKT and p-mTOR proteins detected by the multiplex tissue immunoblotting (MTI) assay performed as described in Example 2 were analyzed from 221 patients with EHCC. Representative expression signals of p-AKT, p-mTOR, and total PTEN for 16 cases are shown in FIG. 1A. The signal intensity of FIG. 1A from maximum to minimum is shown as white to grey to black in order. Cases with higher intensity to p-AKT and p-mTOR showed lower intensity to total PTEN.

The expression pattern was confirmed by immunohistochemistry which was performed as described in Example 3. FIG. 1B shows immunohistochemical staining of p-AKT, p-mTOR, and PTEN protein in dysplasia and EHCC. As found in other studies, a strong correlation between MTI and immunohistochemistry was observed (Chung et al., *Proteomics.* 2006; 6:767-74 and Traicoff et al., *J. Biomed Sci.* 2007; 14:395-405).

Figure 2A:
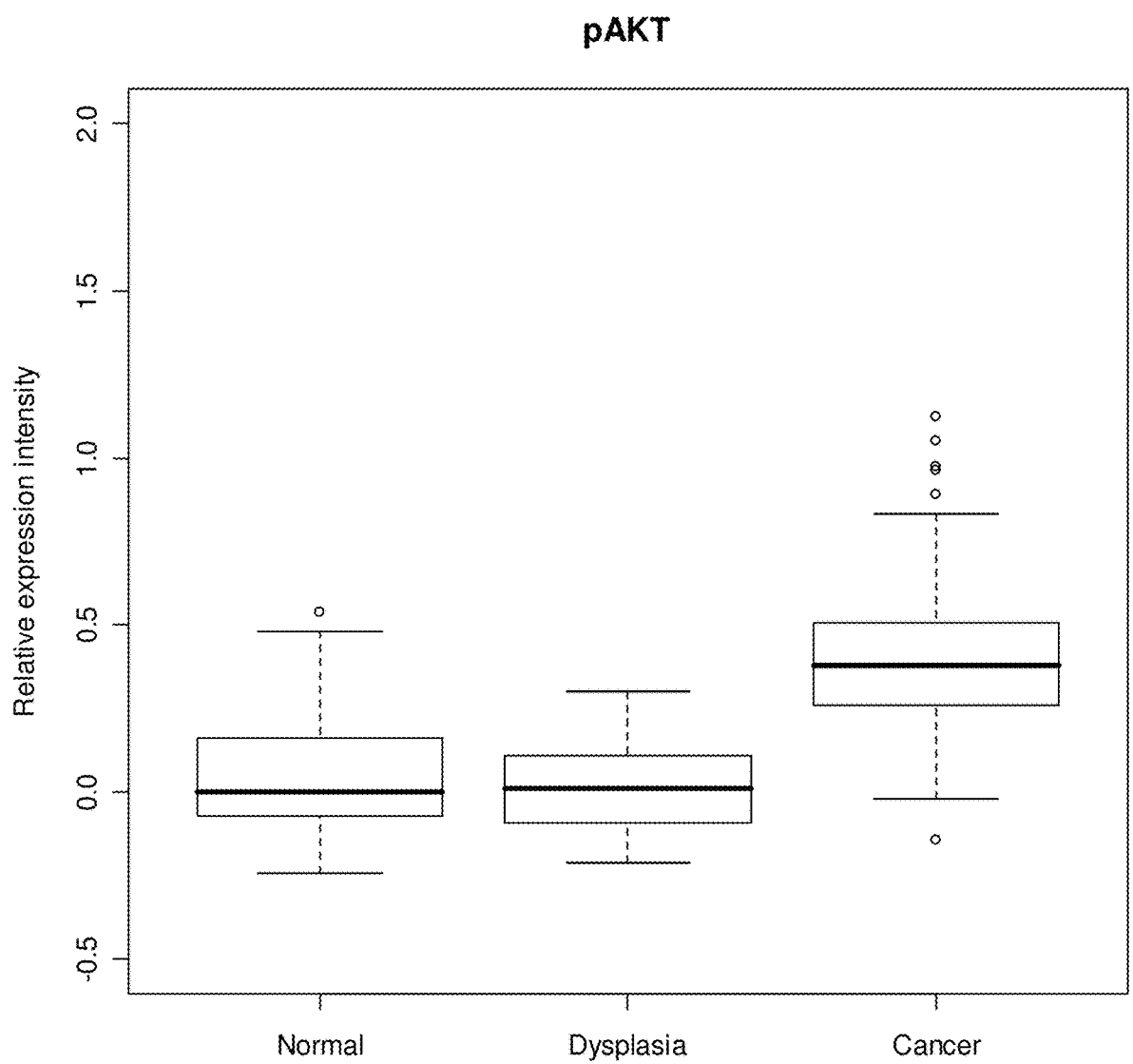
FIG. 2A is a Box plot of relative expression rate of p-AKT protein among normal biliary epithelia, dysplasia, and cancer cases.
Figure 2B:
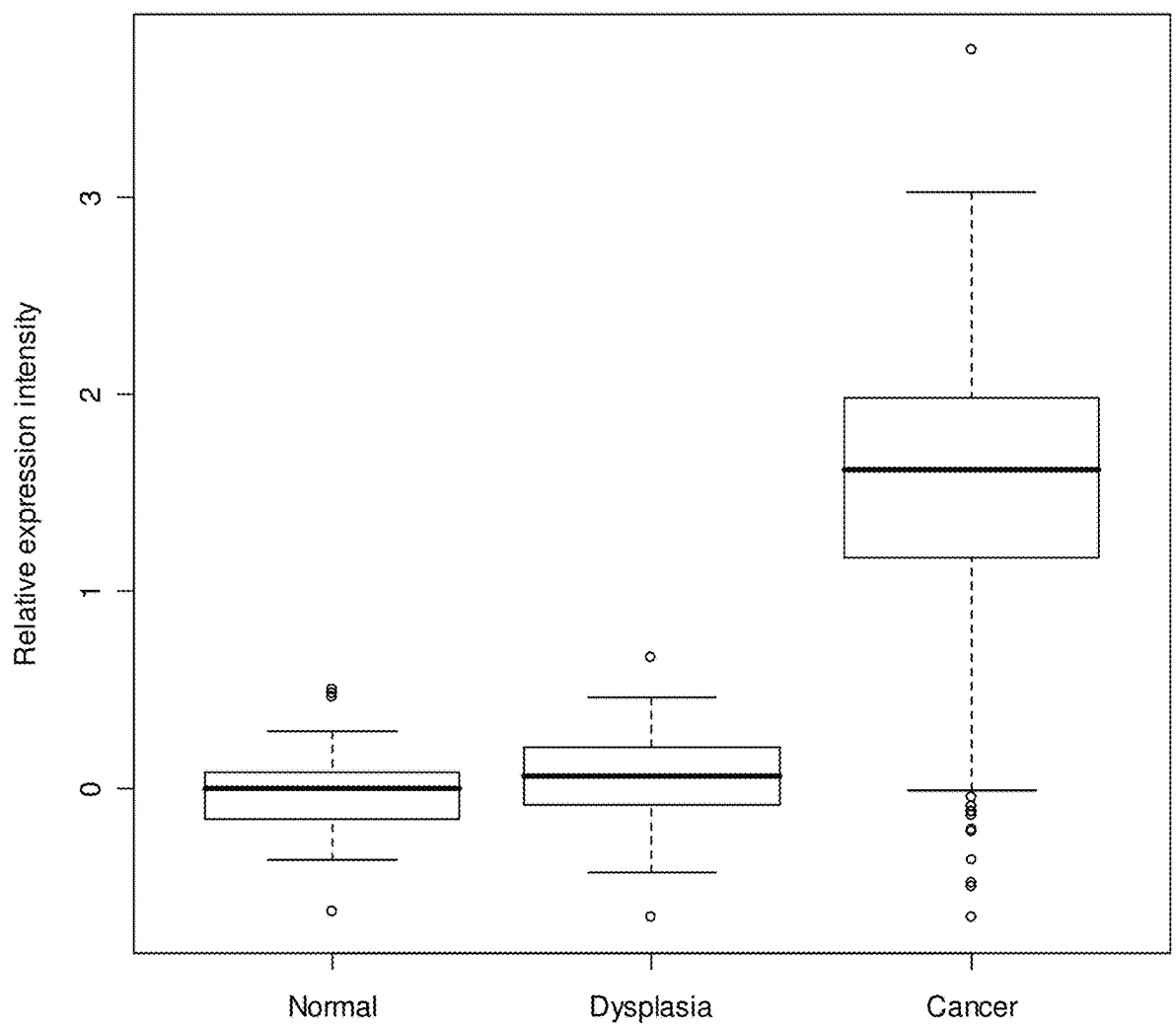
FIG. 2B is a Box plot of relative expression rate of p-mTOR protein among normal biliary epithelia, dysplasia and cancer cases.

Moreover, because of the normalization procedure of the instant disclosure that incorporates both a normalization procedure for total protein content and/or an intra-array normalization step, a strong correlation between MTI and immunohistochemistry data was also observed. After normalization, the relative expression of p-AKT and p-mTOR among normal biliary epithelia, dysplasia, and cancer cases was calculated (FIG. 2). No significant difference of p-AKT and p-mTOR expression was observed between normal bile duct epithelium and dysplastic epithelium. However, samples with EHCC showed statistically significantly higher p-AKT ($p<0.05$, post hoc Duncan test) and p-mTOR ($p<0.05$, post hoc Duncan test) expression than those with normal and dysplastic biliary epithelia (FIGS. 2A and 2B). Overall, p-AKT expression was elevated in 26.3% (15/57 cases) of dysplasia and 84.2% (186/221 cases) of EHCC after normalization (FIG. 2A). Expression of p-mTOR was similar to that of p-AKT, with increased p-mTOR expression detected in 28.1% (16/57 cases) of dysplasia and 83.7% (185/221 cases) of EHCC, respectively (FIG. 2B).

Figure 2C:
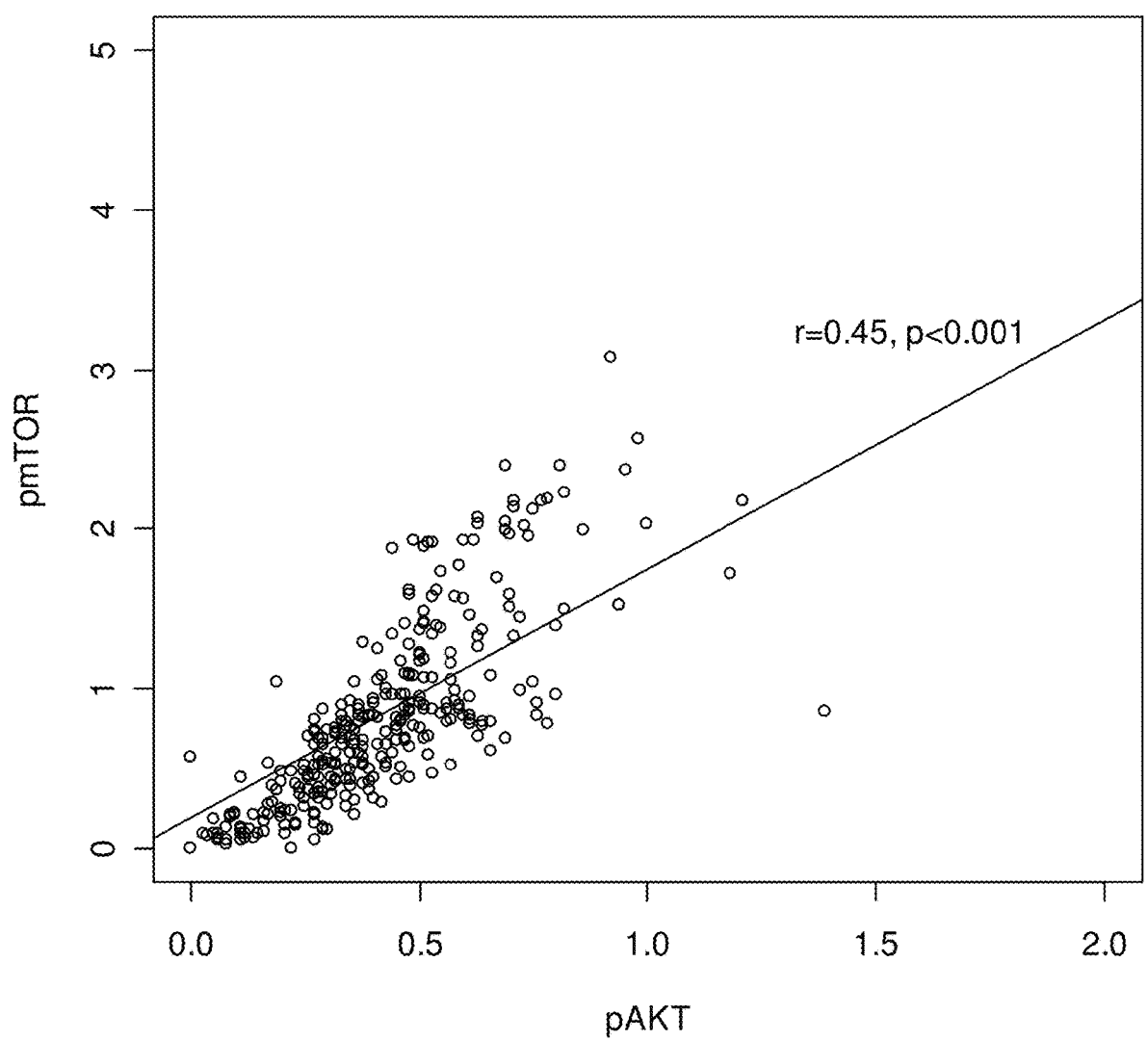
FIG. 2C is a linear-based correlation between p-AKT and p-mTOR protein expression.

A statistically significant positive correlation between p-AKT and p-mTOR ($r=0.45$, $P<0.001$; FIG. 2C) was also observed, supporting the rationale that the two proteins are involved in same signaling pathway as previously reported in cancers from other organs (Faried et al., *Mol. Carcinog.* 2008; 47:446-57).

Example 5

PTEN Expression

Figure 3A:
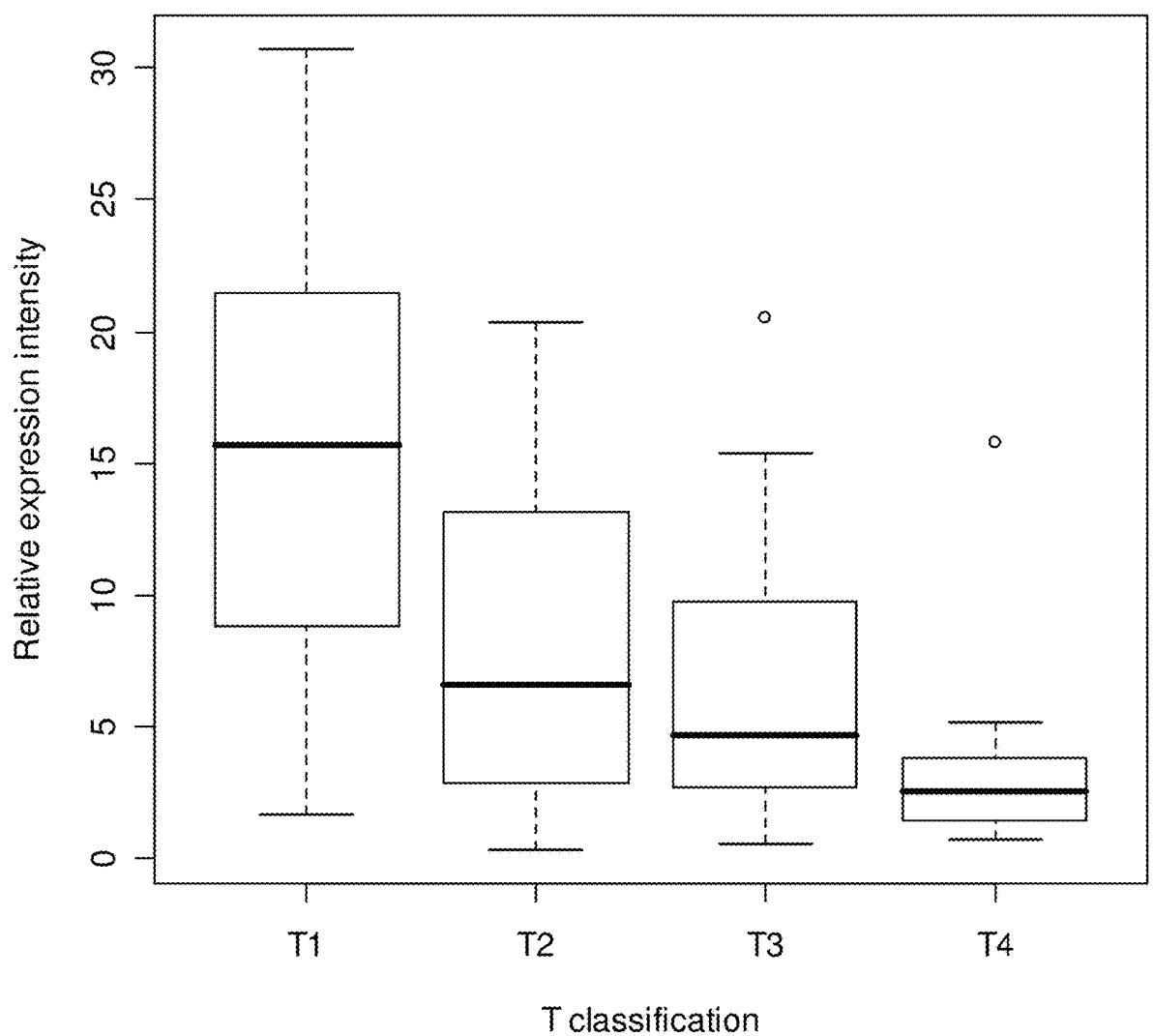
FIG. 3A-3D is a series of Box plots of relative expression rate of PTEN and its association with other clinicopathologic factors.
Figure 3B:
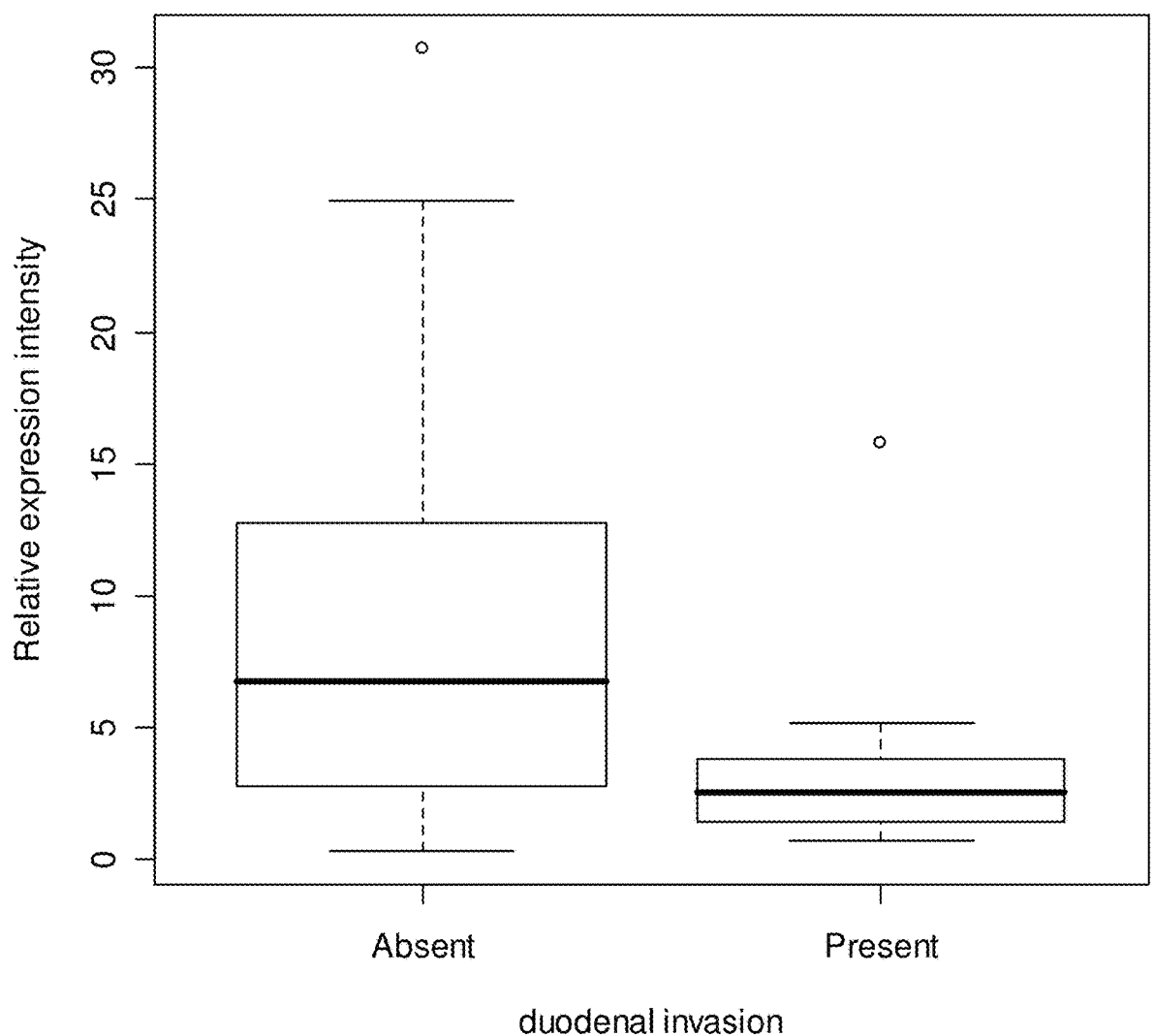
Figure 3C:
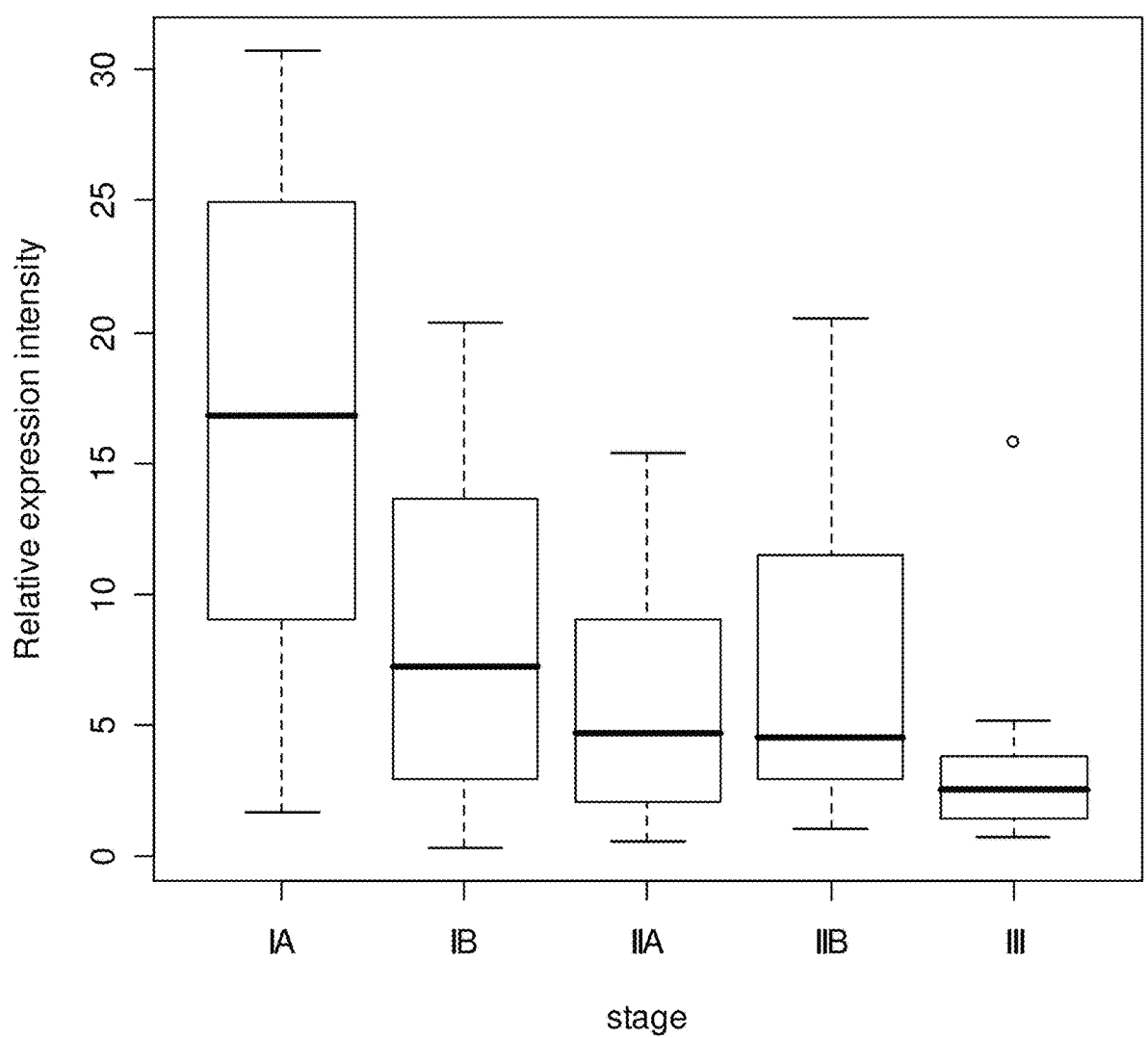
Figure 3D:
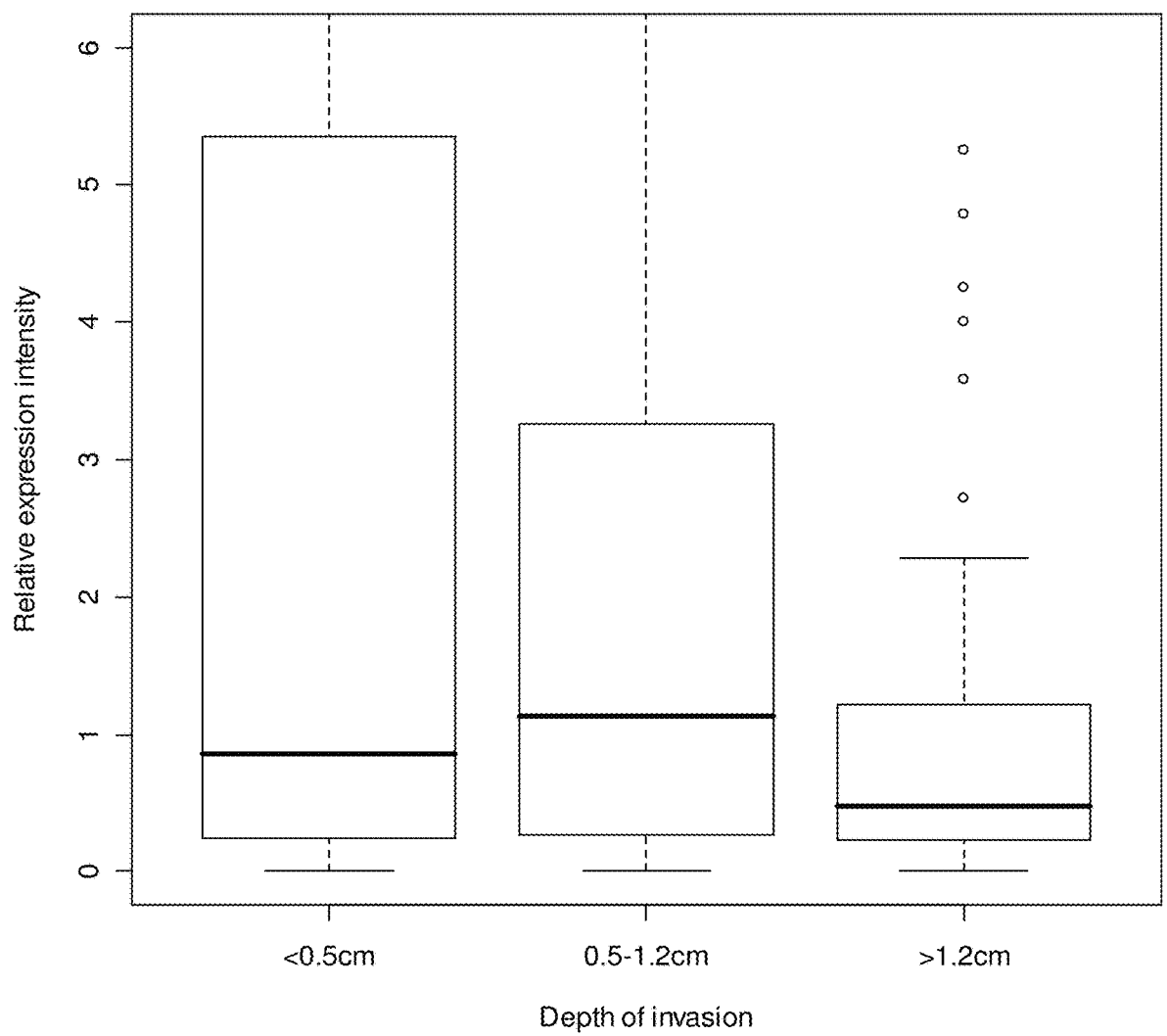

Cases with T1 TNM stage were found to have a significantly higher relative PTEN expression (mean, 16.08; relative expression intensity) than those with other classifications (T2, 8.92; T3, 7.18; T4, 3.98; $p<0.05$, post hoc Duncan test, FIG. 3A). Patients with invasion of the pancreas were observed to have significantly less PTEN expression (mean, 5.94) than those without pancreas invasion (mean, 9.95; $p<0.05$, post hoc Duncan test). Cases with duodenal invasion had statistically less PTEN expression (mean, 3.98) than those without duodenal invasion (mean, 9.04; $p<0.05$, post hoc Duncan test, FIG. 3B). Patients with higher stage grouping of disease (IIB and III) had significantly less PTEN expression (6.45 and 3.98 respectively) than those with lower stages, IA and IIA (17.23 and 8.14 respectively; $p<0.05$, post hoc Duncan test, FIG. 3C). In view of recent findings regarding patient survival indicators (Hong et al., *Mod. Pathol.* 20:562-569, 2007), measurement of the depth of tumor invasion from the basement of membrane to the portion of deepest tumor as an indicator of patient survival was also evaluated (FIG. 3D). Patients with less tumor cell invasion (<0.5 cm of depth of invasion) were observed to have a statistically greater PTEN expression (mean PTEN, 3.41) than cases with deeper tumor cell invasion (>1.2 cm invasion, mean PTEN 1.61; ($p<0.05$, post hoc Duncan test)). Intermediate tumor cell invasion (0.5-1.2 cm invasion) was observed to have a mean PTEN of 2.94, which did not reach statistical significance.

Example 6

Survival Analysis

For survival analysis, patients were categorized as either "high" or "low" expressers of p-AKT, PTEN or p-mTOR based on the median expression of the marker of interest. Although patients with high p-AKT expression had shorter 1, 3, and 5 year survival rates (79.7%, 46.1%, and 36.3%, respectively) than those with low p-AKT expression (83.3%, 83.3%, and 83.3%), the difference was not statistically significant ($p=0.06$).

Figure 4:
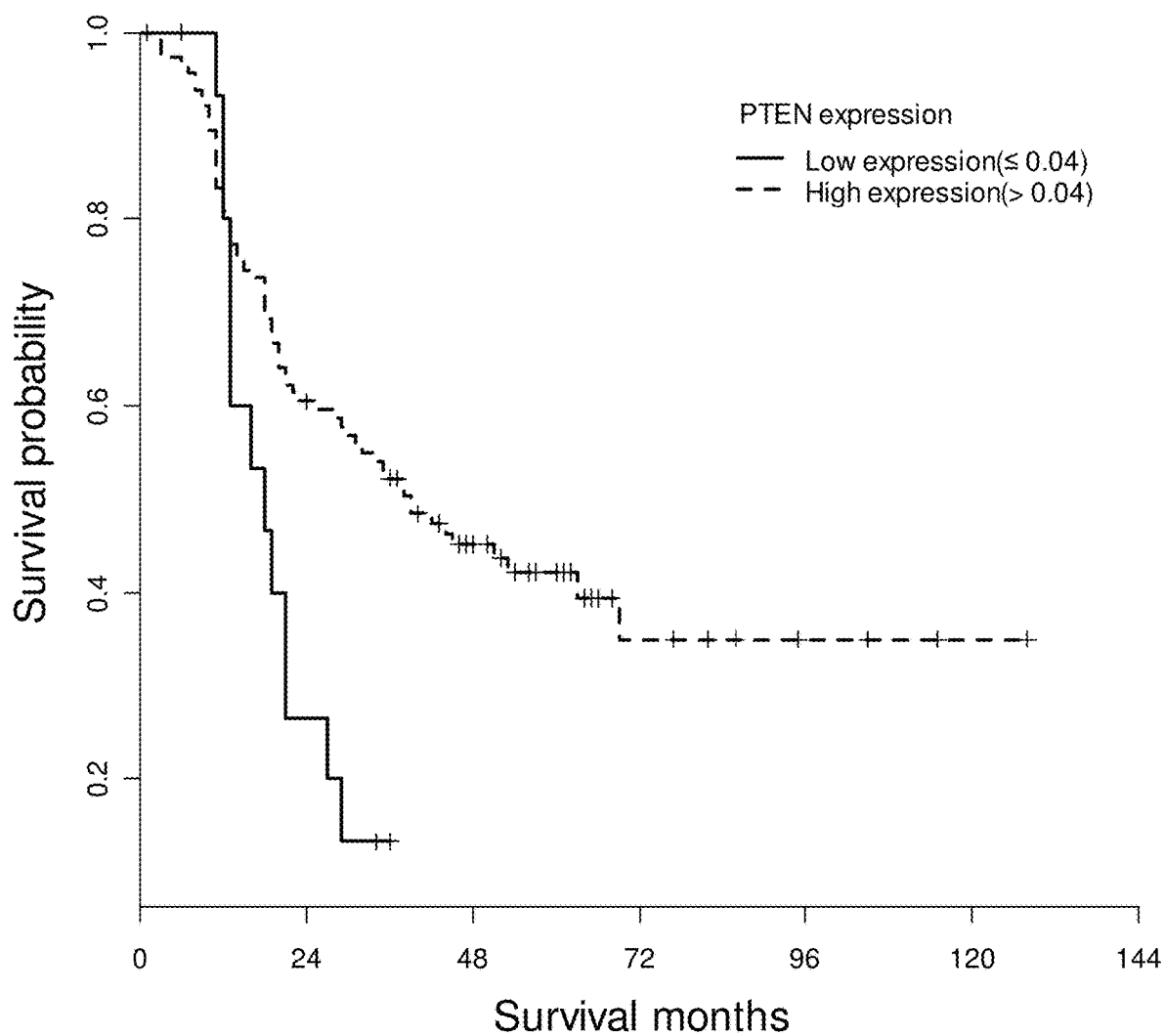
FIG. 4 is a Kaplan-Meier survival analysis of EHCC according to PTEN expression.

The instant investigation also demonstrated that cases with high p-mTOR expression showed shorter 1, 3, and 5 year survival rates (70.6%, 22.1%, and 22.1%, respectively) than those with lower p-mTOR expression (82.2%, 51.5%, and 41.0%); however, there was no statistical significant difference between the two groups ($p=0.06$). FIG. 4 shows a Kaplan-Meier survival analysis of EHCC according to PTEN expression. Patients with low PTEN expression (median survival 18 months; n=17) had a significantly worse patients' survival time than those patients with high PTEN expression (median survival 39 months; n=117; log-rank test, P=0.004). The 1, 3, and 5 year survival rate for patients with low PTEN expression were 80.0%, 13.3%, and 13.3%, respectively, while 1, 3, and 5 year survival rate for those with high PTEN expression were 80.7%, 52.3%, and 42.2%, respectively.

Example 7

Survival Analysis by Expression Profile of PTEN/p-AKT or PTEN/p-mTOR Ratio

To determine if the combination of PTEN and p-AKT expression or of PTEN and p-mTOR expression together have a better predictive potential for determining the survival probability of patients with EHCC, the ratio of PTEN/p-AKT or PTEN/p-mTOR expression was evaluated. By recursive partitioning coupled with log-rank test, the best cutoff point to discriminate patients' survival based on PTEN/p-AKT ratio was observed to be 0.77. FIG. 5A shows Kaplan-Meier survival analysis of EHCC according to PTEN/p-AKT expression. Patients with low PTEN/p-AKT expression (less than or equal to 0.77 of PTEN/p-AKT ratio; median survival 18 months; n=42) had a significantly worse patients' survival time than those with high PTEN/p-AKT expression (greater than 0.77; median survival 45 months; n=91; log-rank test, P=0.003). The 1, 3, and 5 year survival rate for patients with low PTEN/p-AKT expression was 72.6%, 30.0%, and 23.4%, respectively, while 1, 3, and 5 year survival rate for those with high PTEN/p-AKT expression was 84.1%, 56.4%, and 46.2%, respectively (FIG. 5A).

The best cutoff point to discriminate patients' survival based on PTEN/p-mTOR ratio using the same recursive partitioning technique was observed to be 0.33 (using the same technique as was used to calculate the PTEN/p-AKT ratio). FIG. 5B shows Kaplan-Meier survival analysis of EHCC according to PTEN/p-mTOR expression. Patients with low PTEN/p-mTOR expression (less than or equal to 0.33 of PTEN/p-mTOR; median survival 18 months; n=21) had a significantly worse patients' survival time than those patients with high PTEN/p-mTOR expression (greater than 0.33; median survival 39 months; n=112; log-rank test, P=0.009). The 1, 3, and 5 year survival rate for patients with low PTEN/p-mTOR group was 76.2%, 22.9%, and 11.4%, respectively, while 1, 3, and 5 year survival rate for those with high PTEN/p-mTOR expression was observed to be 81.3%, 52.9%, and 43.3%, respectively (FIG. 5B).

Simple inspection and determination of a "rational" cut point—for instance above 0, below 0, above or below 1, or similar numbers—has also been found to be true for other biomarkers developed based on this approach. There is a myriad of methods to determine the cut point.

Example 8

Clinicopathologic Characteristics of Patients

Clinicopathologic characteristics of the examined cases are summarized in Table 1. The ages of the patients ranged from 30 to 84 years (mean, 61 years). One hundred thirty-four patients were men and 87 were women. The tumor sizes ranged from 0.4 to 6 cm (mean 2.6 cm).

Thirty-four cases were T1 tumors, eighty cases were T2 tumors, eighty-four cases were T3 tumors, and twenty-three cases were T4 tumors. The length of the patients' follow-up time ranged from 1 to 128 months, and median survival at last follow up was 34 months.

TABLE 1

Clinicopathologic characteristics of patients with EHCC examined.

| Variables | Variable Subset | No. of patients |
|---|---|---|
| Mean age | 61 years | 221 |
| Gender | Male | 134 |
| | Female | 87 |
| Mean tumor size | 2.6 cm | 221 |
| Histologic subtype | Adenocarcinoma, NOS | 188 |
| | Papillary carcinoma | 15 |
| | Intestinal type adenocarcinoma | 5 |
| | Mucinous carcinoma | 4 |
| | Adenosquamous carcinoma | 5 |
| | Clear cell carcinoma | 1 |
| | Signet ring cell carcinoma | 1 |
| | Sarcomatoid carcinoma | 2 |
| pT classification | pT1 | 34 |
| | pT2 | 80 |
| | pT3 | 84 |
| | pT4 | 23 |
| Lymph node metastasis | Present | 74 |
| | Absent | 147 |
| Hepatic invasion | Present | 7 |
| | Absent | 214 |
| Pancreatic invasion | Present | 100 |
| | Absent | 121 |
| Duodenal invasion | Present | 23 |
| | Absent | 198 |
| Perineural invasion | Present | 150 |
| | Absent | 171 |
| Vascular invasion | Present | 64 |
| | Absent | 157 |
| Type of surgery | Pylorus preserving pancreaticoduodenectomy | 93 |
| | Whipple's operation | 59 |
| | Bile duct resection | 46 |
| | Hepatic lobectomy with bile duct resection | 18 |
| | Pancreaticoduodenectomy with extended hepatic lobectomy | 3 |
| | Pylorus preserving pancreaticoduodenectomy with bile duct resection | 1 |
| | Whipple's operation with bile duct resection | 1 |

Association Between Survival Analysis and Other Clinicopathologic Factors

Other clinicopathologic variables were analyzed for an association with survival, of which T classification (P=0.0002), lymph node metastasis (P=0.0001), differentiation (P<0.0001), pancreatic invasion (P=0.01), duodenal invasion (P=0.003), liver invasion (P=0.005), and vascular invasion (P=0.04), were all significantly associated with survival. In contrast, survival was not associated with perineural invasion and resection marginal status.

Example 9

Multivariate Analysis of Clinicopathologic Factors.

The independent prognostic significance of the PTEN/p-AKT ratio, as well as other clinicopathologic parameters, was determined using the Cox proportional hazards model. Using this multivariate analysis, only lymph node metastasis (P=0.008) and differentiation (P=0.0002) remained significant (Table 2). PTEN/p-AKT did not obtain statistical significance in this analysis (P=0.09). Similar results were obtained from multivariate analysis of PTEN/pm-TOR (not shown).

TABLE 2

Multivariate analysis for the prognosis

| Variable | P-value | Relative risk | 95% confidence interval |
|---|---|---|---|
| PTEN/p-AKT | 0.09 | 1.05 | 0.99-1.11 |
| pT classification | 0.10 | 1.95 | 0.88-4.36 |
| Lymph node metastasis | 0.008* | 1.96 | 1.19-3.21 |
| Duodenal invasion | 0.96 | 0.97 | 0.29-3.20 |
| Liver invasion | 0.66 | 1.39 | 0.32-6.13 |
| Pancreatic invasion | 0.31 | 0.55 | 0.18-1.74 |
| Vascular invasion | 0.08 | 1.59 | 0.95-2.65 |
| Differentiation | 0.0002* | 1.96 | 1.38-2.78 |

*Significant at the level of P < 0.05

Overall, the instant method was utilized to profile proteomic expression profiles of cancer associated proteins, for example by transferring proteins from a paraffin-embedded tissue section to a stack of membranes to which conventional immunoblotting techniques were applied. One of the advantages of the current method is that it allows multiple antigens to be assayed from a single tissue section. This approach permits simultaneously quantifying multiple cancer associated proteins with preservation of the morphologic structure of the tissue. A further benefit of the current method is incorporation of a normalization step that allows for the accurate assessment and comparison of inter- and intra-array samples. In addition, the method disclosed herein allows for confirmation of the protein expression profiles observed, by standard immunohistochemistry techniques. Utilizing the current method, quantitative analysis of protein expression profiles, such as PTEN, mTOR and AKT were obtained and provided survival probability information, as well as the capacity to stratify patients.

Example 10

The Combination of Phospho-AKT, Phospho-mTOR, Phospho-MAPK and EGFR Predicts Survival in Non-Small Cell Lung Cancer Activation of numerous pathways has been documented in non-small cell lung cancer (NSCLC). This may have prognostic significance as well as targets of therapeutic intervention. There is significant cross-talk between these pathways. Epidermal growth factor receptor (EGFR) has emerged as a key target in NSCLC. Two major components of the mitogen-activated protein kinase (MAPK) and AKT signaling pathways are downstream of EGFR and deregulated via genetic and epigenetic mechanisms in many human cancers including lung. We sought to clear the relation between the upstream and downstream of the MAPK and AKT/mTOR pathways in non-small-cell lung cancer.

As described in this example, two hundred thirty-one cases of non-small cell lung cancer patients were arrayed into tissue microarray. Phosphorylated AKT (p-AKT), phosphorylated MAPK (p-MAPK) and phosphorylated mTOR (p-mTOR), and EGFR were immunohistochemically studied and scored by image analyzing system. Survival analysis shows no significant difference in the level of each antibody (which indicates the level of each corresponding antigen) independently, but significant correlations were found for the ratio of p-mTOR to p-AKT (p-mTOR/p-AKT, p=0.043) and the ratio of p-MAPK to EGFR (p-MAPK/EGFR, p=0.031). The sum of these ratios demonstrates a more significant correlation with survival (p=0.007). In multivariate analysis, this sum of ratios of four individual biomarkers remained statistically significant after adjustment with gender, age, cancer type and stage (p=0.038).

Thus, this example demonstrates that the sum of p-mTOR/p-AKT and p-MAPK/EGFR is a predictive marker of survival in patients with NSCLC. Quantitative image analysis of immunohistochemistry with algebraic-like equations offers novel biomarkers of survival and provides clues in identification of patients for targeted therapy.

Introduction

Lung cancer is the most common cause of cancer deaths in both men and women worldwide. Despite advances in treatment, such as combination chemotherapy and chemo-radiation, survival has improved very little over the past few decades (Schiller, *Oncology* 61 Suppl 1:3-13, 2001).

Recently, many targeted agents emerged (LoPiccolo et al., *Drug Resist Updat* 11:32-50, 2008). Gefitinib (Iressa®), the epidermal growth factor receptor (EGFR) tyrosine kinase inhibitor, was approved in Japan for the treatment of non-small cell lung cancer (NSCLC) in 2002. It appears to be more efficacious in specific populations. Tumor characteristics such as the presence of EGFR mutations and/or amplification also appeared to correlate with greater response rates. Mutant EGFRs induce oncogenic effects by activating signaling and anti-apoptotic pathways, notably those mediated by phosphatidylinositol 3-kinase (PI3K)-AKT. But over-expression of EGFR does not successfully predict for treatment advantage with targeted therapeutics and prognosis in NSCLC (Sasaki et al., *J Surg Res* 148:260-3, 2008; Vergis et al., *Lancet Oncol* 9:342-51, 2008; Howard et al., *Lung Cancer* 46:313-23, 2004). Two major signaling pathways downstream of EGFR have been identified: the mitogen-activated protein kinase (MAPK) pathway and the PI3K/AKT/mammalian target of rapamycin (mTOR) pathway (Jorissen et al., *Exp Cell Res* 284:31-53, 2003). AKT activated by extracellular stimuli in a PI3K-dependent manner, pivotal role in oncogenesis (Franke et al., *Cell* 88:435-7, 1997). Induction of these pathways is mediated by phosphorylation of the proteins involved. Numerous studies have independently examined the prognostic significance of members of these pathways (Al-Bazz et al., *Eur J Cancer*, 2009; Galleges et al., *Br J Cancer* 100:145-52, 2009; Guo et al., *Pathol Int* 58:749-56, 2008; Hager et al., *J Cell Mol Med*, 10.1111/j.1582-4934.2008.00488.x , 2008; Herberger et al., *Clin Cancer Res* 13:4795-9, 2007; Pelloski et al., *Clin Cancer Res* 12:3935-41, 2006; Schmitz et al., *Virchows Arch* 450:151-9, 2007; Schmitz et al., *J Hepatol* 48:83-90, 2008; Tsurutani et al., *Lung Cancer* 55:115-21, 2007), but none have taken assayed these pathways as a group.

In this study we focus on MAPK and AKT/mTOR pathway using lung cancer tissue microarray (TMA) and the phosphorylation status of MAPK, AKT, mTOR in combination with EGFR expression. Previously we have demonstrated that ratio-based biomarkers can provide enhanced discrimination of patient survival over assessment of the biomarkers individually (Chung et al., *Clin Cancer Res* 15:660-7, 2009). This approach requires quantitative assessment of the biomarkers. Based on the ratio of biomarkers, where the downstream protein is the numerator to the upstream protein (denominator) for pathways of activation, we demonstrate that the ratio of phosphorylated mTOR (p-mTOR) to phosphorylated AKT (p-AKT) (p-mTOR/p-AKT) and the ratio of phosphorylated mTOR to EGFR (p-MAPK/EGFR) are predictive of survival.

Materials and Methods

Clinical Samples

A total of 231 lung cancer cases were selected from the pathology case archive of Toyama University Hospital based on the diagnosis and the quality of the available tissue on the paraffin blocks. These patients did not receive neoadjuvant treatment. The tumors were staged according to the International Union against Cancer's TNM classification and histologically divided and graded according to 2004 WHO guidelines (Fukuoka et al., Clin Cancer Res 10:4314-24, 2004).

TMA Construction, Immunohistochemistry and Scoring

TMAs were constructed using a TMA arrayer (Pathology Devices, Westminster, Md.) as previously described (Kononen et al., Nat Med 4:844-7, 1998). For each case, areas with the most representative histology were selected from review of hematoxylin-eosin (H&E) stained slides. The cylindrical tissue samples (0.6 mm) were cored from the above described areas in the donor block and extruded into the recipient array. Multiple 5 μm thick sections were cut with a microtome and H&E staining of TMA slides were examined every 50th sections for the presence of tumor cells.

EGFR (M3563) antibody was purchased from DAKO (Carpinteria, Calif.), and p-AKT (T308), p-MAPK and p-mTOR antibodies were purchased from Cell Signaling (Beverly, Mass). The tissue sections were deparaffinized in xylene and rehydrated through a graded alcohol series to distilled water as described herein. Antigen retrieval for EGFR was performed using Proteinase K (DAKO), for p-mTOR using Pressure Chamber (Pascal, DAKO) with pH 6 Target Retrieval Solution (DAKO), and for other antibodies using it with pH10 Target Retrieval Solution (DAKO). These slides were blocked with hydrogen peroxide/methanol. After rinsing, these slides incubated with the primary antibodies over night. The dilutions for each antibody were 1:1000 for EGFR, 1:100 for p-mTOR, 1:500 for p-MAPK, and 1:100 for p-AKT. Target signals were detected with LSAB peroxidase kit and DAB in autostainer. The stained slides were lightly counterstained with hematoxylin and then scanned using the Aperio ScanScope CS Slide Scanner (Aperio Technologies, Vista, Calif.) system. A positive pixel count algorithm in conjunction with the Spectrum Plus Database (Aperio Technologies) was used to develop a qualitative scoring model for both membranous and cytoplasmic expression, and classified pixels into four groups; strong positive, positive, weak positive and negative.

Statistical Analysis.

Statistical analysis was performed using JMP Statistical Discovery Software, Version 7.0.1 (SAS Institute, Cary, N.C.).

Weight Score (WS) was defined as WS=[(the number of strong positive pixels)×1000+(the number of positive pixels)×100+(the number of weak positive pixels)×10+(the number of strong negative pixels)×1]/(the total number of pixels).

Hierarchical clustering was performed on the basis of WS. WS above 10% of the highest score was considered high score group to evaluate each antibody. Using the chi-square test, the antibodies were evaluated in association with each other within each category.

Overall survival was analyzed according to the Kaplan-Meier product-limit method, and the survival curves were compared with the log-rank test. P-mTOR/p-AKT and p-MAPK/EGFR were divided by each of the highest ratio value for normalization and dichotomized positive or negative based on a cut-off value of above or below 0.01. The sum of ratios was defined as "algebraic biomarker". The cutoff value for dichotomization was 0.015. We used a Cox model stratified by trial and adjusted for the following clinical prognostic variables: age at diagnosis (<60 y; ≥60 y), gender, cancer type and stage. P values were considered significant when they are less than 0.05. Chi-square tests were used to compare the positive and negative score groups of algebraic biomarker.

Results

Patient Characteristics and Image Analysis

The number of cases eventually extracted for final analysis is listed in Table 3 along with their clinical data. Survival time and outcome was limited to 204 of 231 cases. The TMA was stained for p-AKT, p-mTOR, EGFR and p-MAPK. Slides were manually reviewed for quality of staining (FIG. 6), and imaged with an Aperio Scanscope CS (Vista, Calif.) with a 20× objective. The TMAs were subsequently de-arrayed in Spectrum Plus, and tumor features were annotated by hand for each TMA core for image analysis. Cores with inadequate tumor were excluded. After tuning of the positive pixel and membrane image analysis algorithms, image analysis was performed on the TMA. A value-weighted score was calculated for each tumor.

TABLE 3

Clinicopathologic characteristics of patients with non-small cell lung cancer

|  | Case No. |
|---|---|
| Gender | |
| Male | 160 |
| Female | 71 |
| Age | |
| Mean ± SD | 66 ± 9.5 |
| Stage | |
| I | 133 |
| II | 46 |
| III | 49 |
| IV | 3 |
| T Status | |
| pT1 | 96 |
| pT2-4 | 135 |
| Lymph node metastasis | |
| negative | 147 |
| positive | 84 |
| Tumor type | |
| Adenocarcinoma | 142 |
| Squamous cell carcinoma | 78 |
| Large cell carcinoma | 11 |
| Differentiation | |
| Well | 91 |
| Moderate | 84 |
| Poor | 43 |
| Other | 13 |

The Ratio of p-mTOR to p-AKT and p-MAPK to EGFR

The current analysis focused on p-mTOR and p-AKT on the downstream AKT/mTOR pathway, and p-MAPK and EGFR on the downstream MAPK pathway. Individual analysis failed to predict survival (FIG. 8A). In contrast, significant correlations were found when ratios of the biomarkers within the pathways were tested—for p-mTOR/p-AKT (p=0.043, log-rank test) and p-MAPK/EGFR (p=0.031) (FIG. 8B).

Algebraic Biomarker (p-mTOR/p-AKT) Plus (p-MAPK/EGFR)

Individually the two ratio-based biomarkers provided statistically significant survival discrimination, which was not provide by analysis of the markers alone. To improve discrimination, as well as in an effort to represent already described cross-talk, a combined biomarker accounting for both ratio-metric approaches was developed. Addition of the two ratios was demonstrated to be a superior approach. This "double ratio" biomarker was more statistically significant, and demonstrates a greater spread between those patients who are biomarker positive and negative than observed with either of the individual ratio based biomarkers. Analysis of the two simple ratio biomarkers, into three groups—both positive, discordant or both negative—resulted in median five-year survival rates that were 78%, 70%, and 46% respectively (p=0.016) (FIG. 8C). In an effort to further refine this, the two ratios were added, and using a new cut-point for classification of positive and negative classes, the double ratio provides a more significant difference. The five-year survival rate was 74% for the algebraic biomarker positive patients and 48% for negative patients (FIG. 8D). When the results of the "double ratio" biomarker were compared to the conventional method of combining biomarkers in Kaplan-Meier analysis, the "double ratio" was clearly superior, eliminating the discordant intermediate groups interpreted as +/− or −/+ (groups denoted as (+/−) in FIG. 8C, without negative impact on the discriminator function of the "double ratio" biomarker. In FIG. 8C, the middle line is patients that cannot correctly be assigned based on traditional approaches, however with the "double ratio" marker developed herein, everyone can be assigned, while the resultant curves remain clearly separate—compared to (+/+) and (−/−) in the two panels of FIG. 8C. Functionally, FIG. 8C proves that the described "biomarker algebra" is modeling the behavior of multiple biomarkers in a fashion that is superior. The log rank test of the Kaplan Meier analysis was strengthened (p=0.007). The algebraic biomarker was associated with gender (p<0.01), T status (p<0.01), cancer type (p<0.01) and differentiation (p<0.01), but not associated with stage (p=0.94) and lymph node metastasis (p=0.35). Algebraic Biomarker positivity was observed in 85% of female compared to 64% of male subjects, 82% of pT1 compared to 61% of pT2-4, 82% of adenocarcinoma compared to 52% of non-adenocarcinoma, and 80% of well differentiated carcinoma compared to 61% of moderate or poor differentiated carcinoma. After adjustment with gender, age, cancer type, and stage, by Cox proportional hazards regression model, the algebraic biomarker remained significant (p=0.038) (Table 4).

TABLE 4

Multivariate analysis with Cox proportional hazards

|  | Hazard ratio (95% CI) | p value |
|---|---|---|
| Double Ratio value |  | 0.038 |
| low | 1 |  |
| high | 0.72 (0.55-0.98) |  |
| Age |  | 0.52 |
| <60 y | 1 |  |
| ≥60 y | 1.01 (0.98-1.04) |  |
| Sex |  | 0.34 |
| Female | 1 |  |
| Male | 1.19 (0.83-1.71) |  |
| Stage |  |  |
| I | 1 |  |
| II | 2.26 (1.05-4.71) | 0.038 |
| III-IV | 4.81 (2.55-9.15) | <0.001 |
| Cancer Type |  | 0.69 |
| Adenocarcinoma | 1 |  |
| Non-adenocarcinoma | 1.07 (0.78-1.48) |  |
| p-MAPK/EGFR |  | 0.032 |
| low | 1 |  |
| high | 0.71 (0.51-0.97) |  |
| p-mTOR/p-AKT |  | 0.17 |
| low | 1 |  |
| high | 0.82 (0.63-1.09) |  |

CI: confidence interval

Hierarchical Clustering and Correlations Between Biomarkers

Figure 7:
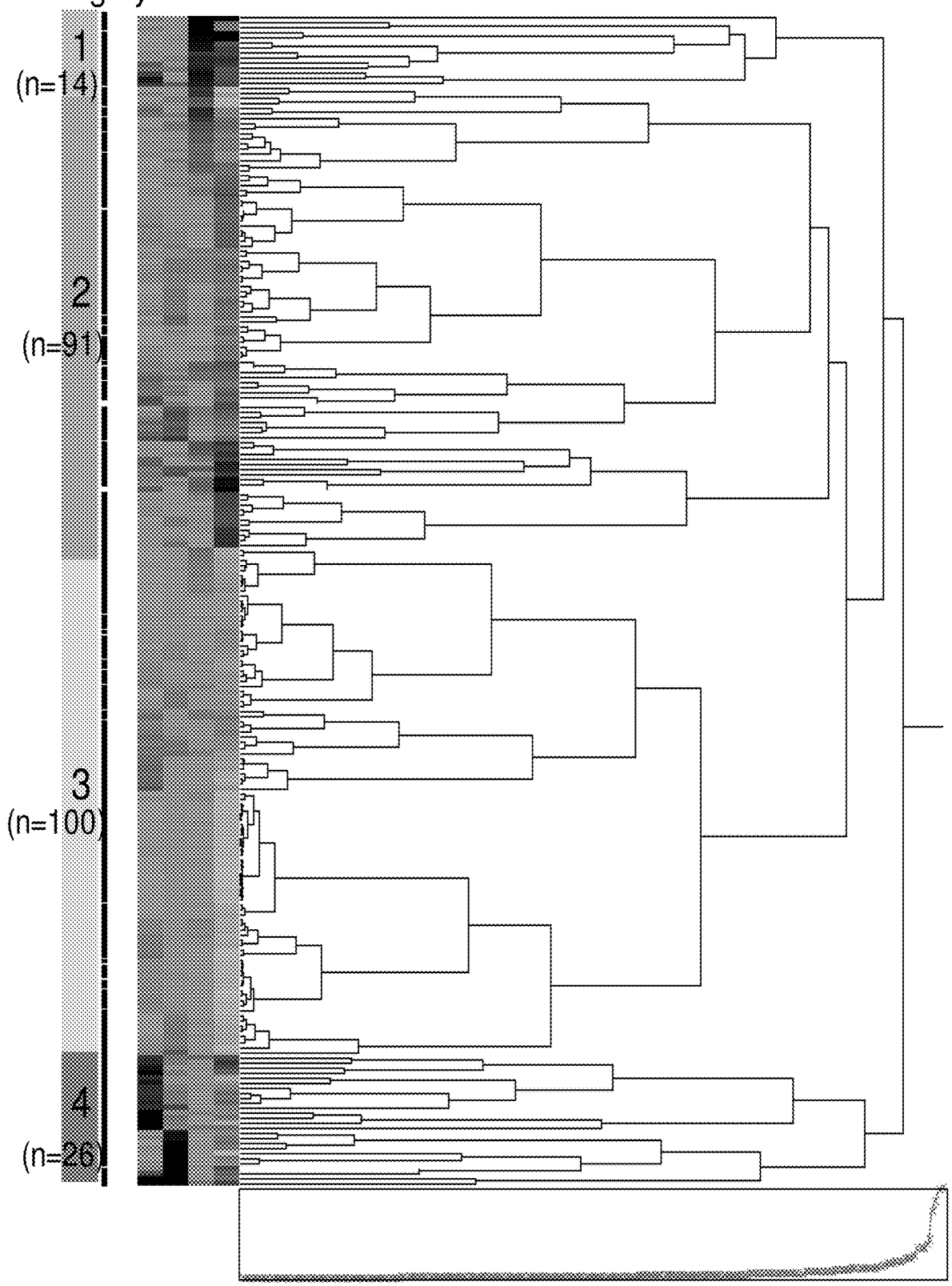
FIG. 7 illustrates hierarchical clustering of correlation coefficients of immunohistochemical expression of p-AKT, p-MAPK, p-mTOR and EGFR, which was performed with Weight Score. Four groups (Category 1 to 4) were defined. This figure demonstrates that hierarchical cluster analysis does not identify ratio based biomarkers.

A total of 231 lung cancer was analyzed by hierarchical clustering based on WS. Based on this clustering, four groups were defined (FIG. 7). All cases of category 1 were positive for p-MAPK, and the WS of most cases were low in category 3 and 4 and of p-AKT was associated with p-mTOR in category 3 (p=0.02, Chi-square tests). In category 2, p-AKT was associated with EGFR (p=0.0015), and p-mTOR was associated with p-MAPK (p=0.0069). All ratios are high in category 1, whereas all ratios are low in category 4 (Table 5). Although the p-MAPK/EGFR ratio of category 2 is same as category 3, the p-mTOR/p-AKT ratio of category 2 is higher than that of category 3. The five-year survival rate of category 2 is 74% and of category 4 is 45%, although stage and lymph node metastasis rate is almost same.

TABLE 5

Association between double ratio, p-mTOR/p-AKT and p-MAPK/EGFR, and four groups (Category 1 to 4) defined with cluster analysis.

|  | Category | | | | p value |
|---|---|---|---|---|---|
|  | 1 | 2 | 3 | 4 |  |
| Double Ratio high/low | 13/1 (93%) | 80/11 (88%) | 60/40 (60%) | 9/17 (35%) | <0.001 |
| p-MAPK/EGFR high/low | 11/3 (79%) | 26/65 (29%) | 31/69 (31%) | 2/24 (8%) | <0.001 |
| p-mTOR/p-AKT high/low | 11/3 (79%) | 83/8 (91%) | 55/45 (55%) | 7/19 (27%) | <0.001 |
| Stage I/II-IV | 13/1 (93%) | 51/40 (56%) | 56/44 (56%) | 13/13 (50%) | 0.021 |
| Lymph node metastasis −/+ | 13/1 (7%) | 57/34 (37%) | 61/39 (39%) | 16/10 (38%) | 0.071 |
| 5-year survival rate | 91% | 74% | 64% | 45% | 0.38 |

Discussion

In the present study, we have found that the combination of p-AKT, EGFR, p-mTOR and p-MAPK is a candidate prognosis marker and it is important to combine multiple antibodies of the parallel signaling pathways. MAPK and AKT/mTOR pathway are pivotal roles in oncogenesis and these antibodies are popular, but application of traditional immunohistochemical assays has not be reproducible by manual scoring approaches which are qualitative and of limited dynamic range. Quantitative analysis was usually determined by using a scale for assessment of distribution and/or a scale for assessment of intensity (Vergis et al., *Lancet Oncol* 9:342-51, 2008; Howard et al., *Lung Cancer* 46:313-23, 2004; Yano et al., *Cancer Res* 68:9479-87, 2008).

This approach of biomarker algebra depends on quantitative measurement of individual biomarkers to generate ratios that reflect pathway activation. In developing this approach, we noted that for pathways of activation, the downstream proteins are numerators, and the upstream proteins are denominators. Conversely, in pathways of repression, the upstream (repressing) protein is the numerator, and the repressed target (or other downstream proteins) is the dominator. Although a number of means can be utilized to determine the optimal cut-offs for assessment of the combined biomarker as positive or negative, these in some fashion reflect the assay conditions (including image analysis) as well as the affinities of the individual antibodies. We believe these ratios reflect a measure of activity through a pathway, as well as dysregulation of this pathway, and maybe useful in identification of patients for targeted therapies. The capacity to add two ratio-based biomarkers into a complex, four-antibody combined biomarker is a reflection of the cross-talk between signaling pathways and may other biologically relevant features of the tumors.

Previous studies have implicated the AKT/mTOR pathway in a diverse range of lung cancer and many cellular processes are regulated by AKT including proliferation, mobility, neovascularisation and survival (Lim et al., *Oncol Rep* 17:853-7, 2007; Tang et al., *Lung Cancer* 51:181-91, 2006; Samuels & Ericson, *Curr Opin Oncol* 18:77-82, 2006). MAPK can be phosphorylated by the EGFR. In the some parts of breast cancer patients, MAPK became a prognostic factor (Derin et al., *Cancer Invest* 26:671-9, 2008; Eralp et al., *Ann Oncol* 19:669-74, 2008). But no previous study compared multiple antibodies with immunohistochemistry. The results discussed in this example indicate that survival differences in p-mTOR/p-AKT and p-MAPK/EGFR were present, even though no significance was observed in single protein expression status. The combination of protein expressions is therefore demonstrated to be more informative than a single protein expression when analyzing pathways and signaling.

Immunohistochemical studies with manual scoring are not a quantitative methods but a qualitative, although immunohistochemistry is popular for evaluation of protein expression (Taylor, *Arch Pathol Lab Med* 124:945-51, 2000). Image analysis yielded quantitative information and enabled comparison of multi-protein expression status. A ratio was a useful way to compare between proximal and distal (in a pathway) protein expressions. Herein, p-mTOR/p-AKT and p-MAPK/EGFR indicated that lower (level) status of downstream than upstream proteins means poor prognosis.

In this study, it is also demonstrated that a combination of ratios may be more informative than a single ratio (FIG. 8C, 8D). The algebraic biomarker described herein was associated with decreased risk of death, differentiation and T status, but not associated with stage or lymph node metastasis. Such algebraic biomarkers can be seen as new tools for prediction.

Immunohistochemistry was a weak tool for quantitative comparison of multiple antibodies. Quantitative image analysis of immunohistochemistry with algebraic-like equations offers novel biomarkers of survival. As illustrated in this example, the sum of p-mTOR/p-AKT and p-MAPK/EGFR is a predictive marker of survival in patients with NSCLC.

Example 11

Identification of Predictive Markers for Gastric Cancer

Taking the above-described approach further, gastric (stomach) cancers have been examined in a very large cohort of 946 patients for whom detailed clinico-pathologic data is available. Numerous markers have been interrogated, including mucin genes, p53, e-cadherin, beta-catenin and others. Her2 and Her3 have been examined using "manual" interpretation by a pathologist, resulting in non-continuous data—qualitative data, but with a range of values rather than binary. In a multivariate analysis with hazards ratios, HER2 expression was a negative prognostic factor (HR 1.37) and HER3 was a positive prognostic factor (HR 0.94). Ratio-based metrics have been applied, demonstrating an HR of 0.61. All of the HRs are statistically significant, however the greater deviation from 1.0, the greater the significance.

The same stains will be subjected to automated image analysis, which is expected to strengthen the noted relationships. Using the methods described herein, there is generally a significant strengthening comparing qualitative data to continuous data.

Unlike the above examples, HER2 and HER3 are not up/downstream of each other in a signaling pathway, but instead they form a functional heterodimer. The proposed model is that it is the balance of HER2 to HER3 expression that is predictive, where an excess of HER2 (for instance, through overexpression of HER2 or underexpression of HER3) is a poor prognostic marker. Functionally, this model is similar to the relationship of the denominator factor(s) being downstream of numerator factor(s), and further supports the concept that the herein-described types of ratiometric biomarkers are functional when there is a connection between the two markers at the biologic level. This also further supports the conclusion that the relationships reported herein are not random observational events.

In view of the many possible embodiments to which the principles of our invention may be applied, it should be recognized that illustrated embodiments are only examples and should not be considered a limitation on the scope of the invention. Rather, the scope is defined by the following claims. We therefore claim all that comes within the scope and spirit of these claims.

The invention claimed is:

1. A method of determining cancer prognosis for a subject with lung cancer, comprising:
   i) identifying at least two cancer associated proteins in a lung tumor sample from the subject;
   ii) quantifying the at least two cancer associated proteins in the sample, comprising:
      a) transferring proteins from the lung tumor sample to a stack of membranes;
      b) probing the stack of membranes with primary antibodies for detection of the at least two cancer associated proteins on the membranes;

c) detecting with fluorescent secondary antibodies the primary antibodies bound to the at least two cancer associated proteins on the membranes;
d) quantifying the signal intensity of the secondary antibodies to determine the quantity of the at least two cancer associated proteins;
e) biotinylating total cellular proteins present in the membranes;
f) incubating the membranes with a fluorescent secondary probe;
g) detecting fluorescence of the secondary probe; and
h) quantifying signal intensity of the fluorescence, thereby quantifying the total cellular proteins;

iii) normalizing the at least two cancer associated proteins in the sample against the total cellular proteins to obtain a normalized value for each cancer associated protein in the sample;

iv) comparing the normalized value of the first cancer associated protein with the normalized value of the second cancer associated protein to obtain a biomarker indicator wherein the biomarker indicator comprises a ratio of the normalized value of the first cancer associated protein to the normalized value of the second cancer associated protein; and v) correlating the biomarker indicator with prognosis of the subject with lung cancer;

wherein the at least two cancer associated proteins comprise p-mTOR and p-AKT, and wherein the first cancer associated protein is p-mTOR and the second cancer associated protein is p-AKT, wherein the prognosis of the subject with lung cancer is improved when the biomarker indicator is higher than a subject with a lower level of the biomarker indicator.

2. The method of claim 1, wherein the subject is a human.

3. The method of claim 1, wherein the subject is a non-human mammal.

4. The method of claim 1, wherein the lung cancer is a carcinoma.

5. The method of claim 1, wherein the at least two cancer associated proteins further comprise a tumor antigen selected from the group consisting of AKT; Blood Group Tn Antigen, CA150; CA19-9; CA50; CAB39L; CD22; CD24; CD63; CD66a +CD66c +CD66d +CD66e; CTAG1B; CTAG2; Carcino Embryonic Antigen (CEA); EBAG9; EGFR; FLJ14868;
FMNL1; GAGE1;GPA33; Ganglioside OAcGD3; Heparanase 1; HER2; HER3; JAKMIP2;
LRIG3; Lung carcinoma Cluster 2; M2A Oncofetal Antigen, MAGE 1; MAGEA10; MAGEA11;
MAGEA12;MAGEA2; MAGEA4; MAGEB1; MAGEB2; MAGEB3; MAGEB4; MAGEB6;
MAGEC1; MAGEE1; MAGEH1; MAGEL2; MGEA5; MOK protein kinase; p-MAPK; MAPK;
mTOR; MUC16; MUC4; Melanoma Associated Antigen; Mesothelin; Mucin 5AC;
Neuroblastoma; OCIAD1; O1P5; Ovarian Carcinoma-associated Antigen; PAGE4; PCNA;
PRAME; Plastin L; Prostate Mucin Antigen (PMA); Prostate Specific Antigen (PSA); PTEN;
RASD2; ROPN1; SART2; SART3; SBEM; SDCCAG10; SDCCAG8; SPANX; SPANXB1;
SSX5; STEAP4; STK31; TAG72; TEM1; XAGE2; Wilms' Tumor Protein, alpha 1 Fetoprotein;
and tumor antigens of epithelial origin.

6. The method of claim 1, wherein the at least two cancer associated proteins further comprise a tumor associated antigen selected from the group consisting of 5T4; AKT;
ACRBP; Blood Group Tn Antigen; CD164; CD20; CTHRC1; ErbB 2; FATE1; HER2; HER3;
GPNMB; Galectin 8; HORMAD1; LYK5; MAGEA6; MAGEA8; MAGEA9; MAGEB18;
MAGED2; MAPK; mTOR; MUC1; MUC2; MelanA; Melanoma gp100; NYS48; PARP9;
PATE; Prostein; PTEN; SDCCAG8; SEPT1; SLC45A2; TBC1D2; TRP1; XAGE1; and tumor associated antigens of epithelial origin.

7. The method of claim 1, wherein the lung tumor sample is selected from the group consisting of an archival tissue sample, a cryo-preserved tissue sample, a fresh tissue sample, an LCM tissue sample, or a tissue microarray.

8. The method of claim 1, further comprising determining the ratio of p-MAPK to EGFR in the sample.

9. The method of claim 8, further comprising performing the addition of the [p-mTOR/p-AKT] and [p-MAPK/EGFR] ratios to provide an additive biomarker.

10. The method of claim 1, wherein the lung cancer is non-small cell lung cancer.

11. The method of claim 1, wherein the secondary probe is fluorescently labeled streptavidin.

12. The method of claim 11, wherein the fluorescently labeled streptavidin is streptavidin-Cy5.

* * * * *